US012606809B2

(12) United States Patent
Qureshi et al.

(10) Patent No.: US 12,606,809 B2
(45) Date of Patent: Apr. 21, 2026

(54) AMYLASE ENZYMES

(71) Applicant: BASF SE, Ludwigshafen (DE)

(72) Inventors: Asfia Qureshi, San Diego, CA (US); Zachary David Miles, San Diego, CA (US); Xuqiu Tan, San Diego, CA (US); Tong Li, San Diego, CA (US); Jared Dennis, San Diego, CA (US); Stefan Jenewein, Ludwigshafen (DE); Priya Anand, Ludwishafen (DE); Jesper Nielsen, San Diego, CA (US)

(73) Assignee: BASF SE, Ludwigshafen (DE)

(*) Notice: Subject to any disclaimer, the term of this patent is extended or adjusted under 35 U.S.C. 154(b) by 1139 days.

(21) Appl. No.: 17/442,675

(22) PCT Filed: Mar. 24, 2020

(86) PCT No.: PCT/EP2020/058129
§ 371 (c)(1),
(2) Date: Sep. 24, 2021

(87) PCT Pub. No.: WO2020/193534
PCT Pub. Date: Oct. 1, 2020

(65) Prior Publication Data
US 2022/0170001 A1      Jun. 2, 2022

Related U.S. Application Data

(60) Provisional application No. 62/890,325, filed on Aug. 22, 2019, provisional application No. 62/823,538, filed on Mar. 25, 2019.

(51) Int. Cl.
| | |
|---|---|
| *C12N 9/26* | (2006.01) |
| *A21D 8/04* | (2006.01) |
| *C12N 1/20* | (2006.01) |
| *C12N 15/75* | (2006.01) |

(52) U.S. Cl.
CPC ........... *C12N 9/2414* (2013.01); *A21D 8/042* (2013.01); *C12N 1/20* (2013.01); *C12N 15/75* (2013.01)

(58) Field of Classification Search
CPC ........ C12N 9/2414; C12N 1/20; C12N 15/75; A21D 8/042
See application file for complete search history.

(56) References Cited

U.S. PATENT DOCUMENTS

| | | | | |
|---|---|---|---|---|
| 7,618,795 | B2 * | 11/2009 | Vikso-Nielsen | ........ C12P 19/16 435/320.1 |
| 8,080,401 | B2 * | 12/2011 | Bessler | ................ C12N 9/2417 435/263 |
| 8,153,412 | B2 * | 4/2012 | Chang | .................. C12N 9/2417 435/254.11 |
| 9,670,436 | B2 | 6/2017 | Jackson et al. | |
| 10,030,239 | B2 * | 7/2018 | Gjermansen | ............. C12N 9/54 |
| 10,167,458 | B2 | 1/2019 | Kaasgaard et al. | |
| 10,519,405 | B2 * | 12/2019 | Andersen | ........... C11D 3/38681 |
| 2012/0021485 | A1 | 1/2012 | Power et al. | |
| 2016/0177238 | A1 | 6/2016 | Jackson et al. | |
| 2016/0326506 | A1 | 11/2016 | Kaasgaard et al. | |
| 2017/0166876 | A1 | 6/2017 | Svendsen et al. | |

FOREIGN PATENT DOCUMENTS

| | | |
|---|---|---|
| EP | 1781790 A2 | 5/2007 |
| WO | WO-94/02597 A1 | 2/1994 |
| WO | WO-94/18314 A1 | 8/1994 |
| WO | WO-95/10603 A1 | 4/1995 |
| WO | WO-96/23872 A1 | 8/1996 |
| WO | WO-97/43424 A1 | 11/1997 |
| WO | WO-99/19467 A1 | 4/1999 |
| WO | WO-00/22103 A1 | 4/2000 |
| WO | WO-00/60060 A2 | 10/2000 |
| WO | WO-02/10355 A2 | 2/2002 |
| WO | WO-02/068589 A2 | 9/2002 |
| WO | WO-02/068597 A2 | 9/2002 |
| WO | WO-03/83054 A2 | 10/2003 |
| WO | WO-2004/091544 A2 | 10/2004 |
| WO | WO-2005/001064 A2 | 1/2005 |
| WO | WO-2006/002643 A2 | 1/2006 |
| WO | WO-2006/066594 A2 | 6/2006 |
| WO | WO-2008/080093 A2 | 7/2008 |
| WO | WO-2009/061380 A2 | 5/2009 |

(Continued)

OTHER PUBLICATIONS

"GenBank AAA63900.1 ABSS Sequence Alignment Alpha Amalyase vs SEQ ID No. 9." downloaded Jun. 27, 2024 <https://abss.uspto.gov/abss4examiners/>. (Year: 1999).*
GenBank AAA63900.1 *Bacillus* sp. TS-23 alpha-amylase, deposited Oct. 26, 1999. Retrieved from <https://www.ncbi.nlm.nih.gov/protein/AAA63900.1 > on Jul. 2, 2024 (Year: 1999).*
Lin et al., "A gene encoding for an alpha-amylase from thermophilic *Bacillus* sp. strain TS-23 and its expression in *E. coli*," Journal of Applied Microbiology, 82: 325-334. (Year: 1997).*
EBI Accession No. GSP:BBX20349, *Bacillus* sp. nutritive polypeptide, SEQ ID 28761 (May 21, 2015).

(Continued)

*Primary Examiner* — Suzanne M Noakes
*Assistant Examiner* — Ciara A McKnight
(74) *Attorney, Agent, or Firm* — MARSHALL, GERSTEIN & BORUN LLP

(57) ABSTRACT

Genetically engineered enzymes having amylase enzyme activity, compositions comprising the enzymes, and methods of making and using the enzymes. Fragments of parent amylase enzymes activity and methods of using the fragments for making genetically engineered enzymes having amylase activity. The genetically engineered amylase enzymes are useful in many different applications such as laundry detergents, dish washing detergents, and cleaning products for homes, industry, vehicle care, baking, animal feed, pulp and paper processing, starch processing, brewing, and ethanol production.

12 Claims, No Drawings
Specification includes a Sequence Listing.

(56) References Cited

FOREIGN PATENT DOCUMENTS

| | | |
|---|---|---|
| WO | WO-2009/100102 A2 | 8/2009 |
| WO | WO-2009/149130 A2 | 12/2009 |
| WO | WO-2010/104675 A1 | 9/2010 |
| WO | WO-2011/098531 A1 | 8/2011 |
| WO | WO-2013/001078 A1 | 1/2013 |
| WO | WO-2013/001087 A2 | 1/2013 |
| WO | WO-2013/184577 A1 | 12/2013 |
| WO | WO-2014/183921 A1 | 11/2014 |

OTHER PUBLICATIONS

EBI Accession No. GSP:BBX20889, Bacillus thuringiensis nutritive polypeptide, SEQ ID 29301, May 21, 2015.

Machius, et al., "Crystal Structure of Calcium-depletedBacillus licheniformis?-amylase at 2.2 Å Resolution", Journal of Molecular Biology, vol. 246, Issue 4, Mar. 3, 1995, pp. 545-559.

"Sequence 12 from U.S. Pat. No. 10,167,458", Database USPTO Proteins [Online], retrieved from EBI Database accession No. USPOP:QBD06052, XP002800786, Feb. 15, 2019, 1 page.

"Sequence 12 from U.S. Pat. No. 9,670,436", Database USPTO Proteins [Online], retrieved from EBI Database accession No. USPOP:AUE83821, XP002800787, Dec. 13, 2017, 01 page.

International Application No. PCT/EP2020/058129, International Search Report and Written Opinion, mailed Oct. 21, 2020.

EBI Accession No. GSP:AXQ16884, Bacillus sp. alpha-amylase mature mutant protein N272E (Oct. 1, 2009).

EBI Accession No. GSP: AQX15862, "Bacillus sp. alpha amylase AmyTS23 mutant protein N272E", (Oct. 1, 2019).

EBI Accession No. UNIPROT:A0A1V3FF02, SubName: Full= Alpha-amylase {ECO:0000313; EMBL:00E00238.1} (Jun. 7, 2017).

International Application No. PCT/EP2020/058130, International Search Report and Written Opinion, Oct. 21, 2020.

International Application No. PCT/EP2020/073514, International Search Report and Written Opinion, mailed Nov. 4, 2020.

* cited by examiner

SEQUENCE LISTING

<160> NUMBER OF SEQ ID NOS: 171

<210> SEQ ID NO 1
<211> LENGTH: 482
<212> TYPE: PRT
<213> ORGANISM: Artificial Sequence
<220> FEATURE:
<223> OTHER INFORMATION: Synthetically generated

<400> SEQUENCE: 1

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
    130                 135                 140

-continued

```
Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Lys Asn Asp Leu Gly Ala Leu
                260                 265                 270

Glu Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
                340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
            405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys
```

<210> SEQ ID NO 2
<211> LENGTH: 1449
<212> TYPE: DNA
<213> ORGANISM: Artificial Sequence
<220> FEATURE:
<223> OTHER INFORMATION: Synthetically generated

<400> SEQUENCE: 2

```
aatactgcac ctattaacga aacaatgatg caatattttg aatgggattt accgaacgat        60
ggaacccttt ggaatagact ccataataat gcgcaaaacc ttaagaatgc aggtattaca       120
```

```
gcgttatggc ttcctccagc gtataaagga acaagtcaaa gcgatgtcgg atacggcgtg      180
tacgatttat atgaccttgg ggaatttaat caaaaaggaa cgattcgaac aaaatacgga      240
acaaaaacac aactggaacg cgcaattaga tccttaaaag ctaacggaat ccaagtatat      300
gcagatgttg tctttaatca taaggcggga gctgacggca cagaatttgt cgatgcggtt      360
gaggtagacc cttctaatcg aaatcaagaa gtgagcggaa cgtatcaaat tgaagcatgg      420
acaaaatttg attttcccgg tcgggggaac acatactcga gttttaaatg gcgttggtat      480
cattttgacg gtaccgattg ggatgaaagc cgaaaattaa atcggattta caaattccgc      540
ggaaaagcat gggactggga agtcgataca gaaaacggaa actatgatta tttaatgttc      600
gctgatttag atatggatca ccctgaggtt gtgacagaat aaaaaaactg gggaacgtgg      660
tacgtcaata ctacaaatat cgatggattc cgcttagatg ccgtaaaaca tattaaattt      720
agttttatgc gggactggct aacatatgta cgtaatcaaa caggaaaaaa tttatttgcc      780 gttgggggaat tttggaaaaa tgatttgggc gcgctcgaga attacattac aaaaaacaaat      840 ggatcgatgt cattatttga tgcacctttg cataacaact tttataccgc ttccaaatcg      900
agtggatatt ttgacatgcg taatttgctg aacggaacgc ttgtccaacg acacccttct      960
cacgctgtga cacttgtcga taaccacgac acgcaaccag ggcaatcttt acagtcatgg     1020
gtcgaacctt ggtttaaacc acttgcttac gcctttattt taacgagaca agagggatat     1080
ccttgcgtat tttacggtga ctattatgga atcccgaaat acaatattcc aggattaaaa     1140
agcaaaatcg acccgctttt aattgctcgt cgggactatg cctatggaac acaacgtgat     1200
tacattgacc atcaagacat tattggatgg acacgcgaag gcattgatac aaaaccaaac     1260
tctggactgg cggctttaat taccgacggc cctggcggaa gcaaatggat gtatgtcggt     1320
aaaaaacatg ctggaaaagt attttatgat ttaaccggaa accgaagtga cacagtaacg     1380
attaatgcgg atggttgggg agaatttaaa gtaaacggag gctccgtttc gatttgggtg     1440
gctaaataa                                                            1449
```

<210> SEQ ID NO 3
<211> LENGTH: 482
<212> TYPE: PRT
<213> ORGANISM: Artificial Sequence
<220> FEATURE:
<223> OTHER INFORMATION: Synthetically generated

<400> SEQUENCE: 3

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125
```

```
Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
                195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Gly His Val Arg Gly Gln Thr Gly Lys
                245                 250                 255

Asn Leu Phe Ala Val Gly Glu Phe Trp Lys Asn Asp Leu Gly Ala Leu
                260                 265                 270

Glu Asn Tyr Ile Thr Lys Thr Asn Gly Ser Met Ser Leu Phe Asp Ala
                275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
                340                 345                 350

Ile Leu Thr Arg Gln Glu Gly Tyr Pro Cys Val Phe Tyr Gly Asp Tyr
                355                 360                 365

Tyr Gly Ile Pro Ser Asp Gly Val Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
                435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys
```

<210> SEQ ID NO 4
<211> LENGTH: 1449
<212> TYPE: DNA
<213> ORGANISM: Artificial Sequence
<220> FEATURE:
<223> OTHER INFORMATION: Synthetically generated

<400> SEQUENCE: 4

-continued

```
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat aaaaaaactg gggaacgtgg     660
tacgtcaata ctacaaatat cgatggattc cgcttagatg ccgtaaaaca tattaaattt     720
agttttatgc gggactggct aggccacgtt cgaggtcaaa caggtaaaaa ccttttttgcc     780 gttgggggaat tttggaaaaa tgatttgggc gcgctcgaga attacattac aaaaaacaaat     840 ggatcgatgt cattatttga tgcacctttg cataacaact tttataccgc ttccaaatcg     900
agtggatatt ttgacatgcg taatttgctg aacggaacgc ttgtccaacg acacccttct     960
cacgctgtga cacttgtcga taaccacgac acgcaaccag ggcaatcttt acagtcatgg    1020
gtcgaacctt ggtttaaacc acttgcttac gcctttattt taacgagaca agagggatat    1080
ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                            1449
```

```
<210> SEQ ID NO 5
<211> LENGTH: 482
<212> TYPE: PRT
<213> ORGANISM: Artificial Sequence
<220> FEATURE:
<223> OTHER INFORMATION: Synthetically generated

<400> SEQUENCE: 5

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
```

```
              100                105                110
Gly Thr Glu Phe Val Asp Ala Val Glu Val Asp Pro Ser Asn Arg Asn
         115                120                125

Gln Glu Val Ser Gly Thr Tyr Gln Ile Glu Ala Trp Thr Lys Phe Asp
         130                135                140

Phe Pro Gly Arg Gly Asn Thr Tyr Ser Ser Phe Lys Trp Arg Trp Tyr
145                150                155                160

His Phe Asp Gly Thr Asp Trp Asp Glu Ser Arg Lys Leu Asn Arg Ile
              165                170                175

Tyr Lys Phe Arg Gly Lys Ala Trp Asp Trp Glu Val Asp Thr Glu Asn
              180                185                190

Gly Asn Tyr Asp Tyr Leu Met Phe Ala Asp Leu Asp Met Asp His Pro
              195                200                205

Glu Val Val Thr Glu Leu Lys Asn Trp Gly Thr Trp Tyr Val Asn Thr
         210                215                220

Thr Asn Ile Asp Gly Phe Arg Leu Asp Ala Val Lys His Ile Lys Phe
225                230                235                240

Ser Phe Met Arg Asp Trp Leu Thr Tyr Val Arg Asn Gln Thr Gly Lys
              245                250                255

Asn Leu Phe Ala Val Gly Glu Phe Trp Lys Asn Asp Leu Gly Ala Leu
              260                265                270

Glu Asn Tyr Ile Thr Lys Thr Asn Gly Ser Met Ser Leu Phe Asp Ala
              275                280                285

Pro Leu His Asn Asn Phe Tyr Thr Ala Ser Lys Ser Ser Gly Tyr Phe
         290                295                300

Asp Met Arg Asn Leu Leu Asn Gly Thr Leu Val Gln Arg His Pro Ser
305                310                315                320

His Ala Val Thr Leu Val Asp Asn His Asp Thr Gln Pro Gly Glu Ala
              325                330                335

Leu Glu Ser Phe Val Gln Gly Trp Phe Lys Pro Leu Ala Tyr Ala Phe
              340                345                350

Ile Leu Thr Arg Gln Glu Gly Tyr Pro Cys Val Phe Tyr Gly Asp Tyr
              355                360                365

Tyr Gly Ile Pro Lys Tyr Asn Ile Pro Gly Leu Lys Ser Lys Ile Asp
         370                375                380

Pro Leu Leu Ile Ala Arg Arg Asp Tyr Ala Tyr Gly Thr Gln Arg Asp
385                390                395                400

Tyr Ile Asp His Gln Asp Ile Ile Gly Trp Thr Arg Glu Gly Ile Asp
              405                410                415

Thr Lys Pro Asn Ser Gly Leu Ala Ala Leu Ile Thr Asp Gly Pro Gly
              420                425                430

Gly Ser Lys Trp Met Tyr Val Gly Lys Lys His Ala Gly Lys Val Phe
              435                440                445

Tyr Asp Leu Thr Gly Asn Arg Ser Asp Thr Val Thr Ile Asn Ala Asp
         450                455                460

Gly Trp Gly Glu Phe Lys Val Asn Gly Gly Ser Val Ser Ile Trp Val
465                470                475                480

Ala Lys
```

<210> SEQ ID NO 6
<211> LENGTH: 1449
<212> TYPE: DNA
<213> ORGANISM: Artificial Sequence
<220> FEATURE:

-continued

<223> OTHER INFORMATION: Synthetically generated

<400> SEQUENCE: 6

```
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780 gttgggggaat tttggaaaaa tgatttgggc gcgctcgaga attacattac aaaaacaaat     840
ggatcgatgt cattatttga tgcacctttg cataacaact tttataccgc ttccaaatcg     900
agtggatatt ttgacatgcg taatttgctg aacggaacgc ttgtccaacg acacccttct     960
cacgctgtga cacttgtcga taaccacgac acacaaccgg gagaagcgct ggaatcattt    1020
gttcaaggat ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac aacgtgat    1200 tacattgacc atcaagacat tattggatgg acacgcgaag cattgatac aaaaccaaac    1260 tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                            1449
```

<210> SEQ ID NO 7
<211> LENGTH: 482
<212> TYPE: PRT
<213> ORGANISM: Artificial Sequence
<220> FEATURE:
<223> OTHER INFORMATION: Synthetically generated

<400> SEQUENCE: 7

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80
```

```
Thr Lys Thr Gln Tyr Ile Gln Ala Ile Gln Ala Ala Lys Ala Ala Gly
              85                  90                  95

Met Gln Val Tyr Ala Asp Val Val Phe Asn His Lys Ala Gly Ala Asp
              100                 105                 110

Gln Thr Glu Phe Val Asp Ala Val Glu Val Asp Pro Ser Asn Arg Asn
              115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                  165                 170                 175

Tyr Lys Phe Arg Gly Lys Ala Trp Asp Trp Glu Val Asp Thr Glu Asn
              180                 185                 190

Gly Asn Tyr Asp Tyr Leu Met Phe Ala Asp Leu Asp Met Asp His Pro
              195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                  245                 250                 255

Asn Leu Phe Ala Val Gly Glu Phe Trp Lys Asn Asp Leu Gly Ala Leu
              260                 265                 270

Glu Asn Tyr Ile Thr Lys Thr Asn Gly Ser Met Ser Leu Phe Asp Ala
              275                 280                 285

Pro Leu His Asn Asn Phe Tyr Thr Ala Ser Lys Ser Ser Gly Tyr Phe
        290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                  325                 330                 335

Leu Gln Ser Trp Val Glu Pro Trp Phe Lys Pro Leu Ala Tyr Ala Phe
              340                 345                 350

Ile Leu Thr Arg Gln Glu Gly Tyr Pro Cys Val Phe Tyr Gly Asp Tyr
              355                 360                 365

Tyr Gly Ile Pro Ser Asp Gly Val Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                  405                 410                 415

Thr Lys Pro Asn Ser Gly Leu Ala Ala Leu Ile Thr Asp Gly Pro Gly
              420                 425                 430

Gly Ser Lys Trp Met Tyr Val Gly Lys Lys His Ala Gly Lys Val Phe
              435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys
```

<210> SEQ ID NO 8

-continued

```
<211> LENGTH: 1449
<212> TYPE: DNA
<213> ORGANISM: Artificial Sequence
<220> FEATURE:
<223> OTHER INFORMATION: Synthetically generated

<400> SEQUENCE: 8
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggaaaaa tgatttgggc gcgctcgaga attacattac aaaaacaaat     840
ggatcgatgt cattatttga tgcacctttg cataacaact tttataccgc ttccaaatcg     900
agtggatatt ttgacatgcg taatttgctg aacggaacgc ttgtccaacg acacccttct     960
cacgctgtga cacttgtcga taaccacgac acgcaaccag gcaatctttt acagtcatgg    1020
gtcgaacctt ggtttaaacc acttgcttac gcctttattt taacgagaca gagggatat     1080 ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                            1449

<210> SEQ ID NO 9
<211> LENGTH: 482
<212> TYPE: PRT
<213> ORGANISM: Artificial Sequence
<220> FEATURE:
<223> OTHER INFORMATION: Synthetically generated

<400> SEQUENCE: 9

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60
```

-continued

```
Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Glu Ala
                325                 330                 335

Leu Glu Ser Phe Val Gln Gly Trp Phe Lys Pro Leu Ala Tyr Ala Phe
            340                 345                 350

Ile Leu Thr Arg Gln Glu Gly Tyr Pro Cys Val Phe Tyr Gly Asp Tyr
        355                 360                 365

Tyr Gly Ile Pro Ser Asp Gly Val Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480
```

Ala Lys

<210> SEQ ID NO 10
<211> LENGTH: 1449
<212> TYPE: DNA
<213> ORGANISM: Artificial Sequence
<220> FEATURE:
<223> OTHER INFORMATION: Synthetically generated

<400> SEQUENCE: 10
aatactgcac ctattaacga acaatgatg caatattttg aatgggattt accgaacgat        60
ggaacccttt ggacaaaggt gaaaaatgaa gccgcaaatc tttcttcgct cggtattaca       120
gcgttatggc ttcctccagc gtataaagga acaagtcaaa gcgatgtcgg atacggcgtg       180
tacgatttat atgaccttgg ggaatttaat caaaaaggaa cgattcgaac aaaatacgga       240
acaaaaacac aactggaacg cgcaattaga tccttaaaag ctaacggaat ccaagtatat       300
gcagatgttg tctttaatca taaggcagga gcggaccaaa cagaatttgt cgatgcggtt       360
gaggtagacc cttctaatcg aaatcaagaa acatctggaa catatcaaat tcaagcatgg       420
acaaaatttg attttcccgg tcgggggaac acatactcga gttttaaatg gcgttggtat       480
cattttgacg gtaccgattg ggatgaaagc cgaaaattaa atcggattta caaattccgc       540
ggaaaagcat gggactggga agtcgataca gaaaacggaa actatgatta tttaatgttc       600
gctgatttag atatggatca ccctgaggtt gtgacagaat taaaaaactg gggaacgtgg       660
tacgtcaata ctacaaatat cgatggattc cgcttagatg ccgtaaaaca tattaaattt       720
agttttatgc gggactggct aacatatgta cgtaatcaaa caggaaaaaa tttatttgcc       780
gttggggaat tttggagcta tgacgtcaat aagctgcata attacattac aaaaacaaat       840
ggatcgatgt cattatttga tgcacctttg cataacaact tttataccgc ttccaaatcg       900
agtggatatt ttgacatgcg taatttgctg aacggaacgc ttgtccaacg acacccttct       960
cacgctgtga cacttgtcga taaccacgac acacaaccgg gagaagcgct ggaatcattt      1020
gttcaaggat ggtttaaacc acttgcttac gcctttattt taacgagaca agagggatat      1080
ccttgcgtat tttacggtga ctattatgga atcccgagcg atggcgtccc aggattaaaa      1140
agcaaaatcg acccgctttt aattgctcgt cgggactatg cctatggaac acaacgtgat      1200
tacattgacc atcaagacat tattggatgg acacgcgaag gcattgatac aaaaccaaac      1260
tctggactgg cggctttaat taccgacggc cctggcggaa gcaaatggat gtatgtcggt      1320
aaaaaacatg ctggaaaagt attttatgat ttaaccggaa accgaagtga cacagtaacg      1380
attaatgcgg atggttgggg agaatttaaa gtaaacggag gctccgtttc gatttgggtg      1440
gctaaataa                                                             1449

<210> SEQ ID NO 11
<211> LENGTH: 482
<212> TYPE: PRT
<213> ORGANISM: Artificial Sequence
<220> FEATURE:
<223> OTHER INFORMATION: Synthetically generated

<400> SEQUENCE: 11

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr

-continued

```
          35                    40                    45
Lys Gly Thr Ser Gln Ser Asp Val Gly Tyr Gly Val Tyr Asp Leu Tyr
    50                    55                    60

Asp Leu Gly Glu Phe Asn Gln Lys Gly Thr Ile Arg Thr Lys Tyr Gly
65                    70                    75                    80

Thr Lys Thr Gln Leu Glu Arg Ala Ile Arg Ser Leu Lys Ala Asn Gly
                  85                    90                    95

Ile Gln Val Tyr Ala Asp Val Val Phe Asn His Lys Ala Gly Ala Asp
                  100                   105                   110

Gln Thr Glu Phe Val Asp Ala Val Glu Val Asp Pro Ser Asn Arg Asn
                  115                   120                   125

Gln Glu Val Ser Gly Thr Tyr Gln Ile Glu Ala Trp Thr Lys Phe Asp
    130                   135                   140

Phe Pro Gly Arg Gly Asn Thr Tyr Ser Ser Phe Lys Trp Arg Trp Tyr
145                   150                   155                   160

His Phe Asp Gly Thr Asp Trp Asp Glu Ser Arg Lys Leu Asn Arg Ile
                  165                   170                   175

Tyr Lys Phe Arg Gly Lys Ala Trp Asp Trp Glu Val Asp Thr Glu Asn
                  180                   185                   190

Gly Asn Tyr Asp Tyr Leu Met Phe Ala Asp Leu Asp Met Asp His Pro
                  195                   200                   205

Glu Val Val Thr Glu Leu Lys Asn Trp Gly Thr Trp Tyr Val Asn Thr
    210                   215                   220

Thr Asn Ile Asp Gly Phe Arg Leu Asp Ala Val Lys His Ile Lys Phe
225                   230                   235                   240

Ser Phe Met Arg Asp Trp Leu Thr Tyr Val Arg Asn Gln Thr Gly Lys
                  245                   250                   255

Asn Leu Phe Ala Val Gly Glu Phe Trp Ser Tyr Asp Val Asn Lys Leu
                  260                   265                   270

His Asn Tyr Ile Thr Lys Thr Asn Gly Ser Met Ser Leu Phe Asp Ala
                  275                   280                   285

Pro Leu His Asn Asn Phe Tyr Thr Ala Ser Lys Ser Ser Gly Tyr Phe
    290                   295                   300

Asp Met Arg Asn Leu Leu Asn Gly Thr Leu Val Gln Arg His Pro Ser
305                   310                   315                   320

His Ala Val Thr Leu Val Asp Asn His Asp Thr Gln Pro Gly Glu Ala
                  325                   330                   335

Leu Glu Ser Phe Val Gln Gly Trp Phe Lys Pro Leu Ala Tyr Ala Phe
                  340                   345                   350

Ile Leu Thr Arg Gln Glu Gly Tyr Pro Cys Val Phe Tyr Gly Asp Tyr
                  355                   360                   365

Tyr Gly Ile Pro Lys Tyr Asn Ile Pro Gly Leu Lys Ser Lys Ile Asp
    370                   375                   380

Pro Leu Leu Ile Ala Arg Arg Asp Tyr Ala Tyr Gly Thr Gln Arg Asp
385                   390                   395                   400

Tyr Ile Asp His Gln Asp Ile Ile Gly Trp Thr Arg Glu Gly Ile Asp
                  405                   410                   415

Thr Lys Pro Asn Ser Gly Leu Ala Ala Leu Ile Thr Asp Gly Pro Gly
                  420                   425                   430

Gly Ser Lys Trp Met Tyr Val Gly Lys Lys His Ala Gly Lys Val Phe
                  435                   440                   445

Tyr Asp Leu Thr Gly Asn Arg Ser Asp Thr Val Thr Ile Asn Ala Asp
    450                   455                   460
```

Gly Trp Gly Glu Phe Lys Val Asn Gly Gly Ser Val Ser Ile Trp Val
465                 470                 475                 480

Ala Lys

<210> SEQ ID NO 12
<211> LENGTH: 1449
<212> TYPE: DNA
<213> ORGANISM: Artificial Sequence
<220> FEATURE:
<223> OTHER INFORMATION: Synthetically generated

<400> SEQUENCE: 12
aatactgcac ctattaacga aacaatgatg caatattttg aatgggattt accgaacgat        60
ggaacccttt ggacaaaggt gaaaaatgaa gccgcaaatc tttcttcgct cggtattaca       120
gcgttatggc ttcctccagc gtataaagga acaagtcaaa gcgatgtcgg atacggcgtg       180
tacgatttat atgaccttgg ggaatttaat caaaaaggaa cgattcgaac aaaatacgga       240
acaaaaacac aactggaacg cgcaattaga tccttaaaag ctaacggaat ccaagtatat       300
gcagatgttg tctttaatca taaggcagga gcggaccaaa cagaatttgt cgatgcggtt       360
gaggtagacc cttctaatcg aaatcaagaa gtgagcggaa cgtatcaaat tgaagcatgg       420
acaaaatttg attttcccgg tcgggggaac acatactcga gttttaaatg gcgttggtat       480
cattttgacg gtaccgattg ggatgaaagc cgaaaattaa atcggattta caaattccgc       540
ggaaaagcat gggactggga agtcgataca gaaaacggaa actatgatta tttaatgttc       600
gctgatttag atatggatca ccctgaggtt gtgacagaat taaaaaactg gggaacgtgg       660
tacgtcaata ctacaaatat cgatggattc cgcttagatg ccgtaaaaca tattaaattt       720
agttttatgc gggactggct aacatatgta cgtaatcaaa caggaaaaaa tttatttgcc       780
gttggggaat tttggagcta tgacgtcaat aagctgcata attacattac aaaaacaaat       840
ggatcgatgt cattatttga tgcacctttg cataacaact tttataccgc ttccaaatcg       900
agtggatatt ttgacatgcg taatttgctg aacggaacgc ttgtccaacg acacccttct       960
cacgctgtga cacttgtcga taaccacgac acacaaccgg gagaagcgct ggaatcattt      1020
gttcaaggat ggtttaaacc acttgcttac gcctttattt taacgagaca agagggatat      1080
ccttgcgtat tttacggtga ctattatgga atcccgaaat acaatattcc aggattaaaa      1140
agcaaaatcg acccgctttt aattgctcgt cgggactatg cctatggaac acaacgtgat      1200
tacattgacc atcaagacat tattggatgg acacgcgaag gcattgatac aaaaccaaac      1260
tctggactgg cggctttaat taccgacggc cctggcggaa gcaaatggat gtatgtcggt      1320
aaaaaacatg ctggaaaagt attttatgat ttaaccggaa accgaagtga cacagtaacg      1380
attaatgcgg atggttgggg agaatttaaa gtaaacggag gctccgtttc gatttgggtg      1440
gctaaataa                                                             1449

<210> SEQ ID NO 13
<211> LENGTH: 482
<212> TYPE: PRT
<213> ORGANISM: Artificial Sequence
<220> FEATURE:
<223> OTHER INFORMATION: Synthetically generated

<400> SEQUENCE: 13

Asn Thr Ala Pro Ile Asn Glu Thr Met Met Gln Tyr Phe Glu Trp Asp
1                 5                  10                  15

```
Leu Pro Asn Asp Gly Thr Leu Trp Asn Arg Leu His Asn Asn Ala Gln
        20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Ser Asp Gly Val Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
```

-continued

```
                435                    440                    445
        Tyr Asp Leu Thr Gly Asn Arg Ser Asp Thr Val Thr Ile Asn Ala Asp
            450                    455                    460

Gly Trp Gly Glu Phe Lys Val Asn Gly Gly Ser Val Ser Ile Trp Val
        465                    470                    475                    480

Ala Lys

<210> SEQ ID NO 14
<211> LENGTH: 1449
<212> TYPE: DNA
<213> ORGANISM: Artificial Sequence
<220> FEATURE:
<223> OTHER INFORMATION: Synthetically generated

<400> SEQUENCE: 14
aatactgcac ctattaacga aacaatgatg caatattttg aatgggattt accgaacgat          60
ggaacccttt ggaatagact ccataataat gcgcaaaacc ttaagaatgc aggtattaca         120
gcgttatggc ttcctccagc gtataaagga acaagtcaaa gcgatgtcgg atacggcgtg         180
tacgatttat atgaccttgg ggaatttaat caaaaaggaa cgattcgaac aaaatacgga         240
acaaaaacac aactggaacg cgcaattaga tccttaaaag ctaacggaat ccaagtatat         300
gcagatgttg tctttaatca taaggcagga gcggaccaaa cagaatttgt cgatgcggtt         360
gaggtagacc cttctaatcg aaatcaagaa gtgagcggaa cgtatcaaat tgaagcatgg         420
acaaaatttg attttcccgg tcgggggaac acatactcga gttttaaatg gcgttggtat         480
cattttgacg gtaccgattg ggatgaaagc cgaaaattaa atcggattta caaattccgc         540
ggaaaagcat gggactggga agtcgataca gaaaacggaa actatgatta tttaatgttc         600
gctgatttag atatggatca ccctgaggtt gtgacagaat taaaaaactg gggaacgtgg         660
tacgtcaata ctacaaatat cgatggattc cgcttagatg ccgtaaaaca tattaaattt         720
agttttatgc gggactggct aacatatgta cgtaatcaaa caggaaaaaa tttatttgcc         780
gttggggaat tttggagcta tgacgtcaat aagctgcata attacattac aaaaacaaat         840
ggatcgatgt cattatttga tgcacctttg cataacaact tttataccgc ttccaaatcg         900
agtggatatt ttgacatgcg ttatttattg aataatacat taatgaaaga tcaaccttca         960
ctcgctgtga cacttgtcga taaccacgac acgcaaccag ggcaatcttt acagtcatgg        1020
gtcgaacctt ggtttaaacc acttgcttac gcctttattt taacgagaca agagggatat        1080
ccttgcgtat tttacggtga ctattatgga atcccgagcg atggcgtccc aggattaaaa        1140
agcaaaatcg acccgctttt aattgctcgt cgggactatg cctatggaac acaacgtgat        1200
tacattgacc atcaagacat tattggatgg acacgcgaag cattgatac aaaaccaaac        1260 tctggactgg cggctttaat taccgacggc cctggcggaa gcaaatggat gtatgtcggt        1320
aaaaaacatg ctggaaaagt attttatgat ttaaccggaa accgaagtga cacagtaacg        1380
attaatgcgg atggttgggg agaatttaaa gtaaacggag gctccgtttc gatttgggtg        1440
gctaaataa                                                                 1449

<210> SEQ ID NO 15
<211> LENGTH: 482
<212> TYPE: PRT
<213> ORGANISM: Artificial Sequence
<220> FEATURE:
<223> OTHER INFORMATION: Synthetically generated

<400> SEQUENCE: 15
```

-continued

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
            165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Ser Asp Gly Val Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415
```

```
Thr Lys Pro Asn Ser Gly Leu Ala Ala Leu Ile Thr Asp Gly Pro Gly
            420                 425             430

Gly Ser Lys Trp Met Tyr Val Gly Lys Lys His Ala Gly Lys Val Phe
            435                 440             445

Tyr Asp Leu Thr Gly Asn Arg Ser Asp Thr Val Thr Ile Asn Ala Asp
        450                 455             460

Gly Trp Gly Glu Phe Lys Val Asn Gly Gly Ser Val Ser Ile Trp Val
465                 470             475             480

Ala Lys
```

<210> SEQ ID NO 16
<211> LENGTH: 1449
<212> TYPE: DNA
<213> ORGANISM: Artificial Sequence
<220> FEATURE:
<223> OTHER INFORMATION: Synthetically generated

<400> SEQUENCE: 16

```
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat aaaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780 gttgggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg taatttgctg aacggaacgc ttgtccaacg acacccttct     960
cacgctgtga cacttgtcga taaccacgac acgcaaccag ggcaatcttt acagtcatgg    1020
gtcgaacctt ggtttaaacc acttgcttac gcctttattt taacgagaca agagggatat    1080
ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag cattgatac aaaaccaaac     1260 tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                           1449
```

<210> SEQ ID NO 17
<211> LENGTH: 482
<212> TYPE: PRT
<213> ORGANISM: Artificial Sequence -continued
<220> FEATURE:
<223> OTHER INFORMATION: Synthetically generated

<400> SEQUENCE: 17

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
            85                  90                  95

Ile Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
            165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
            245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
            325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Ser Asp Gly Val Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400
```

-continued

```
Tyr Ile Asp His Gln Asp Ile Ile Gly Trp Thr Arg Glu Gly Ile Asp
            405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys

<210> SEQ ID NO 18
<211> LENGTH: 1449
<212> TYPE: DNA
<213> ORGANISM: Artificial Sequence
<220> FEATURE:
<223> OTHER INFORMATION: Synthetically generated

<400> SEQUENCE: 18
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat gaagcatgg      420 acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg taatttgctg aacggaacgc ttgtccaacg acacccttct     960
cacgctgtga cacttgtcga taaccacgac acgcaaccag ggcaatcttt acagtcatgg    1020
gtcgaacctt ggtttaaacc acttgcttac gcctttattt taacgagaca agagggatat    1080
ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag ctccgtttc gatttgggtg    1440 gctaaataa                                                           1449
```

-continued

```
<210> SEQ ID NO 19
<211> LENGTH: 482
<212> TYPE: PRT
<213> ORGANISM: Artificial Sequence
<220> FEATURE:
<223> OTHER INFORMATION: Synthetically generated

<400> SEQUENCE: 19

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
            165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Glu Ala
                325                 330                 335

Leu Glu Ser Phe Val Gln Gly Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Ser Asp Gly Val Pro Gly Leu Lys Ser Lys Ile Asp
```

-continued

```
              370              375              380
Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
            450                 455                 460

Gly Trp Gly Glu Phe Lys Val Asn Gly Gly Ser Val Ser Ile Trp Val
465                 470                 475                 480

Ala Lys
```

```
<210> SEQ ID NO 20
<211> LENGTH: 1449
<212> TYPE: DNA
<213> ORGANISM: Artificial Sequence
<220> FEATURE:
<223> OTHER INFORMATION: Synthetically generated

<400> SEQUENCE: 20
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcggggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acacaaccgg gagaagcgct ggaatcattt    1020
gttcaaggat ggtttaaacc acttgcttac gcctttattt taacgagaca agagggatat    1080
ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt atttttatgat ttaaccggaa accgaagtga cacagtaacg    1380
attaatgcgg atggttgggg agaatttaaa gtaaacggag ctccgtttc gatttgggtg     1440
``` gctaaataa                                                                        1449

<210> SEQ ID NO 21
<211> LENGTH: 482
<212> TYPE: PRT
<213> ORGANISM: Artificial Sequence
<220> FEATURE:
<223> OTHER INFORMATION: Synthetically generated

<400> SEQUENCE: 21

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Lys Asn Asp Leu Gly Ala Leu
            260                 265                 270

Glu Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Glu Ala
                325                 330                 335

Leu Glu Ser Phe Val Gln Gly Trp Phe Lys Pro Leu Ala Tyr Ala Phe
            340                 345                 350

-continued

```
Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys

<210> SEQ ID NO 22
<211> LENGTH: 1449
<212> TYPE: DNA
<213> ORGANISM: Artificial Sequence
<220> FEATURE:
<223> OTHER INFORMATION: Synthetically generated

<400> SEQUENCE: 22
aatactgcac ctattaacga aacaatgatg caatattttg aatgggattt accgaacgat        60
ggaacccttt ggacaaaggt gaaaaatgaa gccgcaaatc tttcttcgct cggtattaca       120
gcgttatggc ttcctccagc gtataaagga acaagtcaaa gcgatgtcgg atacggcgtg       180
tacgatttat atgaccttgg ggaatttaat caaaaaggaa cgattcgaac aaaaatacgga       240 acaaaaacac aatatattca agccatccaa gctgccaaag ccgcagggat gcaagtatat       300
gcagatgttg tctttaatca taaggcagga gcggaccaaa cagaatttgt cgatgcggtt       360
gaggtagacc cttctaatcg aaatcaagaa gtgagcggaa cgtatcaaat tgaagcatgg       420
acaaaatttg attttcccgg tcgggggaac acatactcga gttttaaatg gcgttggtat       480
cattttgacg gtaccgattg ggatgaaagc cgaaaattaa atcggattta caaattccgc       540
ggaaaagcat gggactggga agtcgataca gaaaacggaa actatgatta tttaatgttc       600
gctgatttag atatggatca ccctgaggtt gtgacagaat aaaaaaactg gggaacgtgg       660
tacgtcaata ctacaaatat cgatggattc cgcttagatg ccgtaaaaca tattaaattt       720
agttttatgc gggactggct aacatatgta cgtaatcaaa caggaaaaaa tttatttgcc       780
gttggggaat tttggaaaaa tgatttgggc gcgctcgaga attacattac aaaaacaaat       840
ggatcgatgt cattatttga tgcacctttg cataacaact tttataccgc ttccaaatcg       900
agtggatatt ttgacatgcg taatttgctg aacggaacgc ttgtccaacg acacccttct       960
cacgctgtga cacttgtcga taaccacgac acacaaccgg gagaagcgct ggaatcattt      1020
gttcaaggat ggtttaaacc acttgcttac gcctttattt taacgagaca agagggtat      1080 ccttgcgtat tttacggtga ctattatgga atcccgaaat acaatattcc aggattaaaa      1140
agcaaaatcg acccgctttt aattgctcgt cgggactatg cctatggaac acaacgtgat      1200
tacattgacc atcaagacat tattggatgg acacgcgaag cattgatac aaaaccaaac      1260 tctggactgg cggctttaat taccgacggc cctggcggaa gcaaatggat gtatgtcggt      1320
```

```
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                           1449
```

```
<210> SEQ ID NO 23
<211> LENGTH: 482
<212> TYPE: PRT
<213> ORGANISM: Artificial Sequence
<220> FEATURE:
<223> OTHER INFORMATION: Synthetically generated

<400> SEQUENCE: 23

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Tyr
225                 230                 235                 240

Ser Phe Phe Pro Asp Trp Leu Thr Tyr Val Arg Asn Gln Thr Gly Lys
                245                 250                 255

Asn Leu Phe Ala Val Gly Glu Phe Trp Lys Asn Asp Leu Gly Ala Leu
            260                 265                 270

Glu Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335
```

```
Leu Gln Ser Trp Val Glu Pro Trp Phe Lys Pro Leu Ala Tyr Ala Phe
            340                 345             350

Ile Leu Thr Arg Gln Glu Gly Tyr Pro Cys Val Phe Tyr Gly Asp Tyr
            355             360             365

Tyr Gly Ile Pro Lys Tyr Asn Ile Pro Gly Leu Lys Ser Lys Ile Asp
    370             375             380

Pro Leu Leu Ile Ala Arg Arg Asp Tyr Ala Tyr Gly Thr Gln Arg Asp
385             390             395                 400

Tyr Ile Asp His Gln Asp Ile Ile Gly Trp Thr Arg Glu Gly Ile Asp
            405             410                 415

Thr Lys Pro Asn Ser Gly Leu Ala Ala Leu Ile Thr Asp Gly Pro Gly
            420             425             430

Gly Ser Lys Trp Met Tyr Val Gly Lys Lys His Ala Gly Lys Val Phe
            435             440             445

Tyr Asp Leu Thr Gly Asn Arg Ser Asp Thr Val Thr Ile Asn Ala Asp
    450             455             460

Gly Trp Gly Glu Phe Lys Val Asn Gly Gly Ser Val Ser Ile Trp Val
465             470             475             480

Ala Lys
```

<210> SEQ ID NO 24
<211> LENGTH: 1449
<212> TYPE: DNA
<213> ORGANISM: Artificial Sequence
<220> FEATURE:
<223> OTHER INFORMATION: Synthetically generated

<400> SEQUENCE: 24

```
aatactgcac ctattaacga aacaatgatg caatattttg aatgggattt accgaacgat        60
ggaacccttt ggaatagact ccataataat gcgcaaaacc ttaagaatgc aggtattaca       120
gcgttatggc ttcctccagc gtataaagga acaagtcaaa gcgatgtcgg atacggcgtg       180
tacgatttat atgaccttgg ggaatttaat caaaaaggaa cgattcgaac aaaatacgga       240
acaaaaacac aatatattca agccatccaa gctgccaaag ccgcagggat gcaagtatat       300
gcagatgttg tctttaatca taaggcggga gctgacggca cagaatttgt cgatgcggtt       360
gaggtagacc cttctaatcg aaatcaagaa gtgagcggaa cgtatcaaat tgaagcatgg       420
acaaaatttg attttcccgg tcgggggaac acatactcga gttttaaatg gcgttggtat       480
cattttgacg gtaccgattg ggatgaaagc cgaaaattaa atcggattta caaattccgc       540
ggaaaagcat gggactggga agtcgataca gaaaacggaa actatgatta tttaatgttc       600
gctgatttag atatggatca ccctgaggtt gtgacagaat aaaaaaactg gggaacgtgg       660
tacgtcaata ctacaaatat cgatggattc cgcttagatg ccgtaaaaca tattaaatac       720
agctttttcc ctgactggct aacatatgta cgtaatcaaa caggaaaaaa tttatttgcc       780 gttgggggaat tttggaaaaa tgatttgggc gcgctcgaga attacattac aaaaacaaat       840
ggatcgatgt cattatttga tgcacctttg cataacaact tttataccgc ttccaaatcg       900
agtggatatt ttgacatgcg taatttgctg aacggaacgc ttgtccaacg acacccttct       960
cacgctgtga cacttgtcga taaccacgac acgcaaccag ggcaatcttt acagtcatgg      1020
gtcgaacctt ggtttaaacc acttgcttac gcctttattt taacgagaca agagggatat      1080
ccttgcgtat tttacggtga ctattatgga atcccgaaat acaatattcc aggattaaaa      1140
agcaaaatcg acccgctttt aattgctcgt cgggactatg cctatggaac acaacgtgat      1200
```

```
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggtggggg agaatttaaa gtaaacggag gctccgtttc gatttgggtg    1440
gctaaataa                                                            1449
```

```
<210> SEQ ID NO 25
<211> LENGTH: 482
<212> TYPE: PRT
<213> ORGANISM: Artificial Sequence
<220> FEATURE:
<223> OTHER INFORMATION: Synthetically generated

<400> SEQUENCE: 25

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
            165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
```

```
305                 310                 315                 320

His Ala Val Thr Leu Val Asp Asn His Asp Thr Gln Pro Gly Gln Ser
            325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
            370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                    405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys
```

<210> SEQ ID NO 26
<211> LENGTH: 1449
<212> TYPE: DNA
<213> ORGANISM: Artificial Sequence
<220> FEATURE:
<223> OTHER INFORMATION: Synthetically generated

<400> SEQUENCE: 26

```
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat aaaaaaactg gggaacgtgg     660
tacgtcaata ctacaaatat cgatggattc cgcttagatg ccgtaaaaca tattaaattt     720 agtttatgc gggactggct aacatatgta cgtaatcaaa caggaaaaaa tttatttgcc     780 gttgggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg taatttgctg aacggaacgc ttgtccaacg acaccctctt     960
cacgctgtga cacttgtcga taaccacgac acgcaaccag gcaatcttt acagtcatgg    1020 gtcgaacctt ggtttaaacc acttgcttac gcctttattt taacgagaca agagggatat    1080
```

-continued

```
ccttgcgtat tttacggtga ctattatgga atcccgaaat acaatattcc aggattaaaa   1140
agcaaaatcg acccgctttt aattgctcgt cgggactatg cctatggaac acaacgtgat   1200
tacattgacc atcaagacat tattggatgg acacgcgaag gcattgatac aaaaccaaac   1260
tctggactgg cggctttaat taccgacggc cctggcggaa gcaaatggat gtatgtcggt   1320
aaaaaacatg ctggaaaagt attttatgat ttaaccggaa accgaagtga cacagtaacg   1380
attaatgcgg atggttgggg agaatttaaa gtaaacggag gctccgtttc gatttgggtg   1440
gctaaataa                                                           1449
```

```
<210> SEQ ID NO 27
<211> LENGTH: 482
<212> TYPE: PRT
<213> ORGANISM: Artificial Sequence
<220> FEATURE:
<223> OTHER INFORMATION: Synthetically generated

<400> SEQUENCE: 27

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
            165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285
```

-continued

```
Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys
```

```
<210> SEQ ID NO 28
<211> LENGTH: 1449
<212> TYPE: DNA
<213> ORGANISM: Artificial Sequence
<220> FEATURE:
<223> OTHER INFORMATION: Synthetically generated

<400> SEQUENCE: 28
aatactgcac ctattaacga aacaatgatg caatattttg aatgggattt accgaacgat        60
ggaacccttt ggaatagact ccataataat gcgcaaaacc ttaagaatgc aggtattaca       120
gcgttatggc ttcctccagc gtataaagga acaagtcaaa gcgatgtcgg atacggcgtg       180
tacgatttat atgaccttgg ggaatttaat caaaaaggaa cgattcgaac aaaatacgga       240
acaaaaacac aactggaacg cgcaattaga tccttaaaag ctaacggaat ccaagtatat       300
gcagatgttg tctttaatca taaggcggga gctgacggca cagaatttgt cgatgcggtt       360
gaggtagacc cttctaatcg aaatcaagaa gtgagcggaa cgtatcaaat tgaagcatgg       420
acaaaatttg attttcccgg tcggggaac acatactcga gttttaaatg gcgttggtat       480
cattttgacg gtaccgattg ggatgaaagc cgaaaattaa atcggattta caaattccgc       540
ggaaaagcat gggactggga agtcgataca gaaaacggaa actatgatta tttaatgttc       600
gctgatttag atatggatca ccctgaggtt gtgacagaat aaaaaaactg gggaacgtgg       660
tacgtcaata ctacaaatat cgatggattc cgcttagatg ccgtaaaaca tattaaattt       720
agttttatgc gggactggct aacatatgta cgtaatcaaa caggaaaaaa tttatttgcc       780
gttggggaat tttggagcta tgacgtcaat aagctgcata attacattac aaaaacaaat       840
ggatcgatgt cattatttga tgcacctttg cataacaact tttataccgc ttccaaatcg       900
agtggatatt ttgacatgcg ttatttattg aataatacat taatgaaaga tcaaccttca       960
```

-continued

```
ctcgctgtga cacttgtcga taaccacgac acgcaaccag ggcaatcttt acagtcatgg    1020
gtcgaacctt ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                           1449
```

```
<210> SEQ ID NO 29
<211> LENGTH: 482
<212> TYPE: PRT
<213> ORGANISM: Artificial Sequence
<220> FEATURE:
<223> OTHER INFORMATION: Synthetically generated

<400> SEQUENCE: 29

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270
```

-continued

```
His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Glu Ala
                325                 330                 335

Leu Glu Ser Phe Val Gln Gly Trp Phe Lys Pro Leu Ala Tyr Ala Phe
                340                 345                 350

Ile Leu Thr Arg Gln Glu Gly Tyr Pro Cys Val Phe Tyr Gly Asp Tyr
        355                 360                 365

Tyr Gly Ile Pro Ser Asp Gly Val Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
        420                 425                 430

Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys
```

```
<210> SEQ ID NO 30
<211> LENGTH: 1449
<212> TYPE: DNA
<213> ORGANISM: Artificial Sequence
<220> FEATURE:
<223> OTHER INFORMATION: Synthetically generated

<400> SEQUENCE: 30
aatactgcac ctattaacga aacaatgatg caatattttg aatgggattt accgaacgat        60
ggaacccttt ggacaaaggt gaaaaatgaa gccgcaaatc tttcttcgct cggtattaca       120
gcgttatggc ttcctccagc gtataaagga acaagtcaaa gcgatgtcgg atacggcgtg       180
tacgatttat atgaccttgg ggaatttaat caaaaaggaa cgattcgaac aaaatacgga       240
acaaaaacac aatatattca agccatccaa gctgccaaag ccgcagggat gcaagtatat       300
gcagatgttg tctttaatca taaggcggga gctgacggca cagaatttgt cgatgcggtt       360
gaggtagacc cttctaatcg aaatcaagaa gtgagcggaa cgtatcaaat tgaagcatgg       420
acaaaatttg attttcccgg tcgggggaac acatactcga gttttaaatg gcgttggtat       480
cattttgacg gtaccgattg ggatgaaagc cgaaaattaa atcggattta caaattccgc       540
ggaaaagcat gggactggga agtcgataca gaaaacggaa actatgatta tttaatgttc       600
gctgatttag atatggatca ccctgaggtt gtgacagaat aaaaaaactg gggaacgtgg       660
tacgtcaata ctacaaatat cgatggattc cgcttagatg ccgtaaaaca tattaaattt       720
agttttatgc gggactggct aacatatgta cgtaatcaaa caggaaaaaa tttatttgcc       780
gttggggaat tttggagcta tgacgtcaat aagctgcata attacattac aaaaacaaat       840
```

```
ggatcgatgt cattatttga tgcacctttg cataacaact tttataccgc ttccaaatcg    900
agtggatatt ttgacatgcg taatttgctg aacggaacgc ttgtccaacg acacccttct    960
cacgctgtga cacttgtcga taaccacgac acacaaccgg gagaagcgct ggaatcattt    1020
gttcaaggat ggtttaaacc acttgcttac gcctttattt taacgagaca agagggatat    1080
ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                            1449
```

```
<210> SEQ ID NO 31
<211> LENGTH: 482
<212> TYPE: PRT
<213> ORGANISM: Artificial Sequence
<220> FEATURE:
<223> OTHER INFORMATION: Synthetically generated

<400> SEQUENCE: 31

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Gly His Val Arg Gly Gln Thr Gly Lys
```

```
                    245                 250                 255
Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Ser Asp Gly Val Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys
```

```
<210> SEQ ID NO 32
<211> LENGTH: 1449
<212> TYPE: DNA
<213> ORGANISM: Artificial Sequence
<220> FEATURE:
<223> OTHER INFORMATION: Synthetically generated

<400> SEQUENCE: 32
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttccocgg tcggggggaac acatactcga gttttaaatg gcgttggtat     480 catttttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat aaaaaaactg gggaacgtgg     660
tacgtcaata ctacaaatat cgatggattc cgcttagatg ccgtaaaaca tattaaattt     720
```

```
agtttttatgc gggactggct aggccacgtt cgaggtcaaa caggtaaaaa ccttttttgcc        780 gttggggaat tttggagcta tgacgtcaat aagctgcata attacattac aaaaacaaat        840
ggatcgatgt cattatttga tgcacctttg cataacaact tttataccgc ttccaaatcg        900
agtggatatt ttgacatgcg ttatttattg aataatacat taatgaaaga tcaaccttca        960
ctcgctgtga cacttgtcga taaccacgac acgcaaccag ggcaatcttt acagtcatgg       1020
gtcgaacctt ggtttaaacc acttgcttac gcctttattt taacgagaca agagggatat       1080
ccttgcgtat tttacggtga ctattatgga atcccgagcg atggcgtccc aggattaaaa       1140
agcaaaatcg acccgctttt aattgctcgt cgggactatg cctatggaac acaacgtgat       1200
tacattgacc atcaagacat tattggatgg acacgcgaag cattgatac aaaaccaaac        1260 tctggactgg cggctttaat taccgacggc cctggcggaa gcaaatggat gtatgtcggt       1320
aaaaaacatg ctggaaaagt atttttatgat ttaaccggaa accgaagtga cacagtaacg      1380
attaatgcgg atggttgggg agaatttaaa gtaaacggag gctccgtttc gatttgggtg       1440
gctaaataa                                                                1449
```

```
<210> SEQ ID NO 33
<211> LENGTH: 482
<212> TYPE: PRT
<213> ORGANISM: Artificial Sequence
<220> FEATURE:
<223> OTHER INFORMATION: Synthetically generated

<400> SEQUENCE: 33

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
            85                  90                  95

Ile Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
            165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220
```

```
Thr Asn Ile Asp Gly Phe Arg Leu Asp Ala Val Lys His Ile Lys Phe
225             230             235             240

Ser Phe Met Arg Asp Trp Leu Thr Tyr Val Arg Asn Gln Thr Gly Lys
                245             250             255

Asn Leu Phe Ala Val Gly Glu Phe Trp Ser Tyr Asp Val Asn Lys Leu
            260             265             270

His Asn Tyr Ile Thr Lys Thr Asn Gly Ser Met Ser Leu Phe Asp Ala
        275             280             285

Pro Leu His Asn Asn Phe Tyr Thr Ala Ser Lys Ser Ser Gly Tyr Phe
    290             295             300

Asp Met Arg Asn Leu Leu Asn Gly Thr Leu Val Gln Arg His Pro Ser
305             310             315             320

His Ala Val Thr Leu Val Asp Asn His Asp Thr Gln Pro Gly Gln Ser
            325             330             335

Leu Gln Ser Trp Val Glu Pro Trp Phe Lys Pro Leu Ala Tyr Ala Phe
            340             345             350

Ile Leu Thr Arg Gln Glu Gly Tyr Pro Cys Val Phe Tyr Gly Asp Tyr
        355             360             365

Tyr Gly Ile Pro Lys Tyr Asn Ile Pro Gly Leu Lys Ser Lys Ile Asp
    370             375             380

Pro Leu Leu Ile Ala Arg Arg Asp Tyr Ala Tyr Gly Thr Gln Arg Asp
385             390             395             400

Tyr Ile Asp His Gln Asp Ile Ile Gly Trp Thr Arg Glu Gly Ile Asp
            405             410             415

Thr Lys Pro Asn Ser Gly Leu Ala Ala Leu Ile Thr Asp Gly Pro Gly
        420             425             430

Gly Ser Lys Trp Met Tyr Val Gly Lys Lys His Ala Gly Lys Val Phe
        435             440             445

Tyr Asp Leu Thr Gly Asn Arg Ser Asp Thr Val Thr Ile Asn Ala Asp
    450             455             460

Gly Trp Gly Glu Phe Lys Val Asn Gly Gly Ser Val Ser Ile Trp Val
465             470             475             480

Ala Lys
```

<210> SEQ ID NO 34
<211> LENGTH: 1449
<212> TYPE: DNA
<213> ORGANISM: Artificial Sequence
<220> FEATURE:
<223> OTHER INFORMATION: Synthetically generated

<400> SEQUENCE: 34

```
aatactgcac ctattaacga aacaatgatg caatattttg aatgggattt accgaacgat       60
ggaacccttt ggacaaaggt gaaaaatgaa gccgcaaatc tttcttcgct cggtattaca      120
gcgttatggc ttcctccagc gtataaagga acaagtcaaa gcgatgtcgg atacggcgtg      180
tacgatttat atgaccttgg ggaatttaat caaaaaggac cgattcgaac aaaatacgga      240
acaaaaacac aactggaacg cgcaattaga tccttaaaag ctaacggaat ccaagtatat      300
gcagatgttg tctttaatca taaggcagga gcggaccaaa cagaatttgt cgatgcggtt      360
gaggtagacc cttctaatcg aaatcaagaa gtgagcggaa cgtatcaaat tgaagcatgg      420
acaaaatttg attttcccgg tcgggggaac acatactcga gtttaaatg gcgttggtat       480 cattttgacg gtaccgattg ggatgaaagc gaaaattaa atcggattta caaattccgc       540
ggaaaagcat gggactggga agtcgataca gaaaacgaa actatgatta tttaatgttc       600
```

```
gctgatttag atatggatca ccctgaggtt gtgacagaat taaaaaactg gggaacgtgg    660
tacgtcaata ctacaaatat cgatggattc cgcttagatg ccgtaaaaca tattaaattt    720
agttttatgc gggactggct aacatatgta cgtaatcaaa caggtaaaaa cctttttgcc    780
gttggggaat tttggagcta tgacgtcaat aagctgcata attacattac aaaaacaaat    840
ggatcgatgt cattatttga tgcacctttg cataacaact tttataccgc ttccaaatcg    900
agtggatatt ttgacatgcg taatttgctg aacggaacgc ttgtccaacg acacccttct    960
cacgctgtga cacttgtcga taaccacgac acgcaaccag ggcaatcttt acagtcatgg   1020
gtcgaacctt ggtttaaacc acttgcttac gcctttattt taacgagaca agagggatat   1080
ccttgcgtat tttacggtga ctattatgga atcccgaaat acaatattcc aggattaaaa   1140
agcaaaatcg acccgctttt aattgctcgt cgggactatg cctatggaac acaacgtgat   1200
tacattgacc atcaagacat tattggatgg acacgcgaag gcattgatac aaaaccaaac   1260
tctggactgg cggctttaat taccgacggc cctggcggaa gcaaatggat gtatgtcggt   1320
aaaaaacatg ctggaaaagt attttatgat ttaaccggaa accgaagtga cacagtaacg   1380
attaatgcgg atggttgggg agaatttaaa gtaaacggag ctccgtttc gatttgggtg   1440 gctaaataa                                                            1449
```

<210> SEQ ID NO 35
<211> LENGTH: 482
<212> TYPE: PRT
<213> ORGANISM: Artificial Sequence
<220> FEATURE:
<223> OTHER INFORMATION: Synthetically generated

<400> SEQUENCE: 35

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
            195                 200                 205
```

```
Glu Val Val Thr Glu Leu Lys Asn Trp Gly Thr Trp Tyr Val Asn Thr
    210             215             220
Thr Asn Ile Asp Gly Phe Arg Leu Asp Ala Val Lys His Ile Lys Phe
225             230             235             240
Ser Phe Met Arg Asp Trp Leu Thr Tyr Val Arg Asn Gln Thr Gly Lys
            245             250             255
Asn Leu Phe Ala Val Gly Glu Phe Trp Ser Tyr Asp Val Asn Lys Leu
            260             265             270
His Asn Tyr Ile Thr Lys Thr Asn Gly Ser Met Ser Leu Phe Asp Ala
            275             280             285
Pro Leu His Asn Asn Phe Tyr Thr Ala Ser Lys Ser Ser Gly Tyr Phe
    290             295             300
Asp Met Arg Asn Leu Leu Asn Gly Thr Leu Val Gln Arg His Pro Ser
305             310             315             320
His Ala Val Thr Leu Val Asp Asn His Asp Thr Gln Pro Gly Gln Ser
            325             330             335
Leu Gln Ser Trp Val Glu Pro Trp Phe Lys Pro Leu Ala Tyr Ala Phe
            340             345             350
Ile Leu Thr Arg Gln Glu Gly Tyr Pro Cys Val Phe Tyr Gly Asp Tyr
            355             360             365
Tyr Gly Ile Pro Lys Tyr Asn Ile Pro Gly Leu Lys Ser Lys Ile Asp
    370             375             380
Pro Leu Leu Ile Ala Arg Arg Asp Tyr Ala Tyr Gly Thr Gln Arg Asp
385             390             395             400
Tyr Ile Asp His Gln Asp Ile Ile Gly Trp Thr Arg Glu Gly Ile Asp
            405             410             415
Thr Lys Pro Asn Ser Gly Leu Ala Ala Leu Ile Thr Asp Gly Pro Gly
            420             425             430
Gly Ser Lys Trp Met Tyr Val Gly Lys Lys His Ala Gly Lys Val Phe
            435             440             445
Tyr Asp Leu Thr Gly Asn Arg Ser Asp Thr Val Thr Ile Asn Ala Asp
    450             455             460
Gly Trp Gly Glu Phe Lys Val Asn Gly Gly Ser Val Ser Ile Trp Val
465             470             475             480
Ala Lys
```

```
<210> SEQ ID NO 36
<211> LENGTH: 1449
<212> TYPE: DNA
<213> ORGANISM: Artificial Sequence
<220> FEATURE:
<223> OTHER INFORMATION: Synthetically generated

<400> SEQUENCE: 36
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcggga gctgacggca cagaatttgt cgatgcggtt     360
gaggtagacc cttctaatcg aaatcaagaa gtgagcggaa cgtatcaaat gaagcatgg      420 acaaaatttg attttcccgg tcggggaac acatactcga gttttaaatg gcgttggtat     480
```

```
cattttgacg gtaccgattg ggatgaaagc cgaaaattaa atcggattta caaattccgc    540
ggaaaagcat gggactggga agtcgataca gaaaacggaa actatgatta tttaatgttc    600
gctgatttag atatggatca ccctgaggtt gtgacagaat aaaaaaactg gggaacgtgg    660
tacgtcaata ctacaaatat cgatggattc cgcttagatg ccgtaaaaca tattaaattt    720
agttttatgc gggactggct aacatatgta cgtaatcaaa caggaaaaaa tttatttgcc    780
gttggggaat tttggagcta tgacgtcaat aagctgcata attacattac aaaaacaaat    840
ggatcgatgt cattatttga tgcacctttg cataacaact tttataccgc ttccaaatcg    900
agtggatatt ttgacatgcg taatttgctg aacggaacgc ttgtccaacg cacccttct     960 cacgctgtga cacttgtcga taaccacgac acgcaaccag ggcaatcttt acagtcatgg   1020
gtcgaacctt ggtttaaacc acttgcttac gcctttattt taacgagaca agagggatat   1080
ccttgcgtat tttacggtga ctattatgga atcccgaaat acaatattcc aggattaaaa   1140
agcaaaatcg acccgctttt aattgctcgt cgggactatg cctatggaac acaacgtgat   1200
tacattgacc atcaagacat tattggatgg acacgcgaag gcattgatac aaaaccaaac   1260
tctggactgg cggctttaat taccgacggc cctggcggaa gcaaatggat gtatgtcggt   1320
aaaaaacatg ctggaaaagt attttatgat ttaaccggaa accgaagtga cacagtaacg   1380
attaatgcgg atggttgggg agaatttaaa gtaaacggag gctccgtttc gatttgggtg   1440
gctaaataa                                                          1449
```

<210> SEQ ID NO 37
<211> LENGTH: 482
<212> TYPE: PRT
<213> ORGANISM: Artificial Sequence
<220> FEATURE:
<223> OTHER INFORMATION: Synthetically generated

<400> SEQUENCE: 37

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
```

-continued

```
                180               185                190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
                260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
                340                 345                 350

Ile Leu Thr Arg Gln Glu Gly Tyr Pro Cys Val Phe Tyr Gly Asp Tyr
                355                 360                 365

Tyr Gly Ile Pro Lys Tyr Asn Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
                435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys
```

```
<210> SEQ ID NO 38
<211> LENGTH: 1449
<212> TYPE: DNA
<213> ORGANISM: Artificial Sequence
<220> FEATURE:
<223> OTHER INFORMATION: Synthetically generated

<400> SEQUENCE: 38
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
```

-continued

```
gaggtagacc cttctaatcg aaatcaagaa acatctggaa catatcaaat tcaagcatgg      420
acaaaatttg attttcccgg tcgggggaac acatactcga gttttaaatg gcgttggtat      480
cattttgacg gtaccgattg ggatgaaagc cgaaaattaa atcggattta caaattccgc      540
ggaaaagcat gggactggga agtcgataca gaaaacggaa actatgatta tttaatgttc      600
gctgatttag atatggatca ccctgaggtt gtgacagaat taaaaaactg gggaacgtgg      660
tacgtcaata ctacaaatat cgatggattc cgcttagatg ccgtaaaaca tattaaattt      720
agttttatgc gggactggct aacatatgta cgtaatcaaa caggaaaaaa tttatttgcc      780 gttgggggaat tttggagcta tgacgtcaat aagctgcata attacattac aaaaacaaat      840
ggatcgatgt cattatttga tgcacctttg cataacaact tttataccgc ttccaaatcg      900
agtggatatt ttgacatgcg ttatttattg aataatacat taatgaaaga tcaaccttca      960
ctcgctgtga cacttgtcga taaccacgac acgcaaccag ggcaatcttt acagtcatgg     1020
gtcgaacctt ggtttaaacc acttgcttac gcctttattt taacgagaca agagggatat     1080
ccttgcgtat tttacggtga ctattatgga atcccgaaat acaatattcc aggattaaaa     1140
agcaaaatcg acccgctttt aattgctcgt cgggactatg cctatggaac acaacgtgat     1200
tacattgacc atcaagacat tattggatgg acacgcgaag gcattgatac aaaaccaaac     1260
tctggactgg cggctttaat taccgacggc cctggcggaa gcaaatggat gtatgtcggt     1320
aaaaaacatg ctggaaaagt attttatgat ttaaccggaa accgaagtga cacagtaacg     1380
attaatgcgg atggttgggg agaatttaaa gtaaacggag gctccgtttc gatttgggtg     1440
gctaaataa                                                            1449
```

<210> SEQ ID NO 39
<211> LENGTH: 482
<212> TYPE: PRT
<213> ORGANISM: Artificial Sequence
<220> FEATURE:
<223> OTHER INFORMATION: Synthetically generated

<400> SEQUENCE: 39

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160
```

```
His Phe Asp Gly Thr Asp Trp Asp Glu Ser Arg Lys Leu Asn Arg Ile
                165             170             175

Tyr Lys Phe Arg Gly Lys Ala Trp Asp Trp Glu Val Asp Thr Glu Asn
            180             185             190

Gly Asn Tyr Asp Tyr Leu Met Phe Ala Asp Leu Asp Met Asp His Pro
            195             200             205

Glu Val Val Thr Glu Leu Lys Asn Trp Gly Thr Trp Tyr Val Asn Thr
        210             215             220

Thr Asn Ile Asp Gly Phe Arg Leu Asp Ala Val Lys His Ile Lys Phe
225             230             235             240

Ser Phe Met Arg Asp Trp Leu Thr Tyr Val Arg Asn Gln Thr Gly Lys
            245             250             255

Asn Leu Phe Ala Val Gly Glu Phe Trp Ser Tyr Asp Val Asn Lys Leu
            260             265             270

His Asn Tyr Ile Thr Lys Thr Asn Gly Ser Met Ser Leu Phe Asp Ala
            275             280             285

Pro Leu His Asn Asn Phe Tyr Thr Ala Ser Lys Ser Ser Gly Tyr Phe
        290             295             300

Asp Met Arg Asn Leu Leu Asn Gly Thr Leu Val Gln Arg His Pro Ser
305             310             315             320

His Ala Val Thr Leu Val Asp Asn His Asp Thr Gln Pro Gly Gln Ser
            325             330             335

Leu Gln Ser Trp Val Glu Pro Trp Phe Lys Pro Leu Ala Tyr Ala Phe
            340             345             350

Ile Leu Thr Arg Gln Glu Gly Tyr Pro Cys Val Phe Tyr Gly Asp Tyr
            355             360             365

Tyr Gly Ile Pro Lys Tyr Asn Ile Pro Gly Leu Lys Ser Lys Ile Asp
        370             375             380

Pro Leu Leu Ile Ala Arg Arg Asp Tyr Ala Tyr Gly Thr Gln Arg Asp
385             390             395             400

Tyr Ile Asp His Gln Asp Ile Ile Gly Trp Thr Arg Glu Gly Ile Asp
            405             410             415

Thr Lys Pro Asn Ser Gly Leu Ala Ala Leu Ile Thr Asp Gly Pro Gly
            420             425             430

Gly Ser Lys Trp Met Tyr Val Gly Lys Lys His Ala Gly Lys Val Phe
            435             440             445

Tyr Asp Leu Thr Gly Asn Arg Ser Asp Thr Val Thr Ile Asn Ala Asp
        450             455             460

Gly Trp Gly Glu Phe Lys Val Asn Gly Gly Ser Val Ser Ile Trp Val
465             470             475             480

Ala Lys
```

<210> SEQ ID NO 40
<211> LENGTH: 1449
<212> TYPE: DNA
<213> ORGANISM: Artificial Sequence
<220> FEATURE:
<223> OTHER INFORMATION: Synthetically generated

<400> SEQUENCE: 40

```
aatactgcac ctattaacga aacaatgatg caatattttg aatgggattt accgaacgat        60
ggaacccttt ggacaaaggt gaaaaatgaa gccgcaaatc tttcttcgct cggtattaca       120
gcgttatggc ttcctccagc gtataaagga acaagtcaaa gcgatgtcgg atacggcgtg       180
tacgatttat atgaccttgg ggaatttaat caaaaaggaa cgattcgaac aaaatacgga       240
```

-continued

```
acaaaaacac aactggaacg cgcaattaga tccttaaaag ctaacggaat ccaagtatat      300
gcagatgttg tctttaatca taaggcggga gctgacggca cagaatttgt cgatgcggtt      360
gaggtagacc cttctaatcg aaatcaagaa gtgagcggaa cgtatcaaat tgaagcatgg      420
acaaaatttg attttcccgg tcgggggaac acatactcga gttttaaatg gcgttggtat      480
cattttgacg gtaccgattg ggatgaaagc cgaaaattaa atcggattta caaattccgc      540
ggaaaagcat gggactggga agtcgataca gaaaacggaa actatgatta tttaatgttc      600
gctgatttag atatggatca ccctgaggtt gtgacagaat taaaaaactg gggaacgtgg      660
tacgtcaata ctacaaatat cgatggattc cgcttagatg ccgtaaaaca tattaaattt      720
agttttatgc gggactggct aacatatgta cgtaatcaaa caggaaaaaa tttatttgcc      780
gttggggaat tttggagcta tgacgtcaat aagctgcata attacattac aaaaacaaat      840
ggatcgatgt cattatttga tgcacctttg cataacaact tttataccgc ttccaaatcg      900
agtggatatt ttgacatgcg taatttgctg aacggaacgc ttgtccaacg acacccttct      960
cacgctgtga cacttgtcga taaccacgac acgcaaccag ggcaatcttt acagtcatgg     1020
gtcgaacctt ggtttaaacc acttgcttac gcctttattt taacgagaca agagggatat     1080
ccttgcgtat tttacggtga ctattatgga atcccgaaat acaatattcc aggattaaaa     1140
agcaaaatcg acccgctttt aattgctcgt cgggactatg cctatggaac acaacgtgat     1200
tacattgacc atcaagacat tattggatgg acacgcgaag gcattgatac aaaaccaaac     1260
tctggactgg cggctttaat taccgacggc cctggcggaa gcaaatggat gtatgtcggt     1320
aaaaaacatg ctggaaaagt attttatgat ttaaccggaa accgaagtga cacagtaacg     1380
attaatgcgg atggttgggg agaatttaaa gtaaacggag ctccgtttc gatttgggtg     1440 gctaaataa                                                            1449
```

<210> SEQ ID NO 41
<211> LENGTH: 482
<212> TYPE: PRT
<213> ORGANISM: Artificial Sequence
<220> FEATURE:
<223> OTHER INFORMATION: Synthetically generated

<400> SEQUENCE: 41

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140
```

```
Phe Pro Gly Arg Gly Asn Thr Tyr Ser Ser Phe Lys Trp Arg Trp Tyr
145             150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Asn Leu Leu Asn Gly Thr Leu Val Gln Arg His Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys
```

```
<210> SEQ ID NO 42
<211> LENGTH: 1449
<212> TYPE: DNA
<213> ORGANISM: Artificial Sequence
<220> FEATURE:
<223> OTHER INFORMATION: Synthetically generated

<400> SEQUENCE: 42
aatactgcac ctattaacga aacaatgatg caatattttg aatgggattt accgaacgat      60
ggaacccttt ggacaaaggt gaaaaatgaa gccgcaaatc tttcttcgct cggtattaca     120
```

```
gcgttatggc ttcctccagc gtataaagga acaagtcaaa gcgatgtcgg atacggcgtg      180
tacgatttat atgaccttgg ggaatttaat caaaaaggaa cgattcgaac aaaatacgga      240
acaaaaacac aactggaacg cgcaattaga tccttaaaag ctaacggaat ccaagtatat      300
gcagatgttg tctttaatca taaggcagga gcggaccaaa cagaatttgt cgatgcggtt      360
gaggtagacc cttctaatcg aaatcaagaa gtgagcggaa cgtatcaaat tgaagcatgg      420
acaaaatttg attttcccgg tcgggggaac acatactcga gttttaaatg gcgttggtat      480
cattttgacg gtaccgattg ggatgaaagc cgaaaattaa atcggattta caaattccgc      540
ggaaaagcat gggactggga agtcgataca gaaaacggaa actatgatta tttaatgttc      600
gctgatttag atatggatca ccctgaggtt gtgacagaat aaaaaactg gggaacgtgg       660 tacgtcaata ctacaaatat cgatggattc cgcttagatg ccgtaaaaca tattaaattt      720 agtttatgc gggactggct aacatatgta cgtaatcaaa caggaaaaaa tttatttgcc       780 gttgggggaat tttggagcta tgacgtcaat aagctgcata attacattac aaaaacaaat      840
ggatcgatgt cattatttga tgcacctttg cataacaact tttataccgc ttccaaatcg      900
agtggatatt ttgacatgcg taatttgctg aacggaacgc ttgtccaacg acacccttca      960
ctcgctgtga cacttgtcga taaccacgac acgcaaccag ggcaatcttt acagtcatgg     1020
gtcgaacctt ggtttaaacc acttgcttac gcctttattt taacgagaca agagggatat     1080
ccttgcgtat tttacggtga ctattatgga atcccgaaat acaatattcc aggattaaaa     1140
agcaaaatcg acccgctttt aattgctcgt cgggactatg cctatggaac acaacgtgat     1200
tacattgacc atcaagacat tattggatgg acacgcgaag gcattgatac aaaaccaaac     1260
tctggactgg cggctttaat taccgacggc cctggcggaa gcaaatggat gtatgtcggt     1320
aaaaaacatg ctggaaaagt attttatgat ttaaccggaa accgaagtga cacagtaacg     1380
attaatgcgg atggttgggg agaatttaaa gtaaacggag ctccgtttc gatttgggtg      1440 gctaaataa                                                             1449
```

```
<210> SEQ ID NO 43
<211> LENGTH: 482
<212> TYPE: PRT
<213> ORGANISM: Artificial Sequence
<220> FEATURE:
<223> OTHER INFORMATION: Synthetically generated

<400> SEQUENCE: 43

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
```

-continued

```
          115                    120                    125

Gln Glu Val Ser Gly Thr Tyr Gln Ile Glu Ala Trp Thr Lys Phe Asp
     130                    135                    140

Phe Pro Gly Arg Gly Asn Thr Tyr Ser Ser Phe Lys Trp Arg Trp Tyr
145                    150                    155                    160

His Phe Asp Gly Thr Asp Trp Asp Glu Ser Arg Lys Leu Asn Arg Ile
               165                    170                    175

Tyr Lys Phe Arg Gly Lys Ala Trp Asp Trp Glu Val Asp Thr Glu Asn
               180                    185                    190

Gly Asn Tyr Asp Tyr Leu Met Phe Ala Asp Leu Asp Met Asp His Pro
               195                    200                    205

Glu Val Val Thr Glu Leu Lys Asn Trp Gly Thr Trp Tyr Val Asn Thr
     210                    215                    220

Thr Asn Ile Asp Gly Phe Arg Leu Asp Ala Val Lys His Ile Lys Phe
225                    230                    235                    240

Ser Phe Met Arg Asp Trp Leu Thr Tyr Val Arg Asn Gln Thr Gly Lys
               245                    250                    255

Asn Leu Phe Ala Val Gly Glu Phe Trp Ser Tyr Asp Val Asn Lys Leu
               260                    265                    270

His Asn Tyr Ile Thr Lys Thr Asn Gly Ser Met Ser Leu Phe Asp Ala
               275                    280                    285

Pro Leu His Asn Asn Phe Tyr Thr Ala Ser Lys Ser Ser Gly Tyr Phe
     290                    295                    300

Asp Met Arg Tyr Leu Leu Asn Asn Thr Leu Met Lys Asp Gln Pro Ser
305                    310                    315                    320

Leu Ala Val Thr Leu Val Asp Asn His Asp Thr Gln Pro Gly Glu Ala
               325                    330                    335

Leu Glu Ser Phe Val Gln Gly Trp Phe Lys Pro Leu Ala Tyr Ala Phe
               340                    345                    350

Ile Leu Thr Arg Gln Glu Gly Tyr Pro Cys Val Phe Tyr Gly Asp Tyr
               355                    360                    365

Tyr Gly Ile Pro Lys Tyr Asn Ile Pro Gly Leu Lys Ser Lys Ile Asp
     370                    375                    380

Pro Leu Leu Ile Ala Arg Arg Asp Tyr Ala Tyr Gly Thr Gln Arg Asp
385                    390                    395                    400

Tyr Ile Asp His Gln Asp Ile Ile Gly Trp Thr Arg Glu Gly Ile Asp
               405                    410                    415

Thr Lys Pro Asn Ser Gly Leu Ala Ala Leu Ile Thr Asp Gly Pro Gly
               420                    425                    430

Gly Ser Lys Trp Met Tyr Val Gly Lys Lys His Ala Gly Lys Val Phe
               435                    440                    445

Tyr Asp Leu Thr Gly Asn Arg Ser Asp Thr Val Thr Ile Asn Ala Asp
     450                    455                    460

Gly Trp Gly Glu Phe Lys Val Asn Gly Gly Ser Val Ser Ile Trp Val
465                    470                    475                    480

Ala Lys
```

```
<210> SEQ ID NO 44
<211> LENGTH: 1449
<212> TYPE: DNA
<213> ORGANISM: Artificial Sequence
<220> FEATURE:
<223> OTHER INFORMATION: Synthetically generated

<400> SEQUENCE: 44
```

```
aatactgcac ctattaacga aacaatgatg caatattttg aatgggattt accgaacgat    60
ggaacccttt ggaatagact ccataataat gcgcaaaacc ttaagaatgc aggtattaca   120
gcgttatggc ttcctccagc gtataaagga acaagtcaaa gcgatgtcgg atacggcgtg   180
tacgatttat atgaccttgg ggaatttaat caaaaaggaa cgattcgaac aaaatacgga   240
acaaaaacac aatatattca agccatccaa gctgccaaag ccgcagggat gcaagtatat   300
gcagatgttg tctttaatca taaggcggga gctgacggca cagaatttgt cgatgcggtt   360
gaggtagacc cttctaatcg aaatcaagaa gtgagcggaa cgtatcaaat tgaagcatgg   420
acaaaatttg attttcccgg tcgggggaac acatactcga gttttaaatg gcgttggtat   480
cattttgacg gtaccgattg ggatgaaagc cgaaaattaa atcggattta caaattccgc   540
ggaaaagcat gggactggga agtcgataca gaaaacggaa actatgatta tttaatgttc   600
gctgatttag atatggatca ccctgaggtt gtgacagaat aaaaaaactg gggaacgtgg   660
tacgtcaata ctacaaatat cgatggattc cgcttagatg ccgtaaaaca tattaaattt   720
agttttatgc gggactggct aacatatgta cgtaatcaaa caggaaaaaa tttatttgcc   780
gttggggaat tttggagcta tgacgtcaat aagctgcata attacattac aaaaacaaat   840
ggatcgatgt cattatttga tgcacctttg cataacaact tttataccgc ttccaaatcg   900
agtggatatt ttgacatgcg ttatttattg aataatacat taatgaaaga tcaaccttca   960
ctcgctgtga cacttgtcga taaccacgac acacaaccgg gagaagcgct ggaatcattt  1020
gttcaaggat ggtttaaacc acttgcttac gcctttattt taacgagaca agagggatat  1080
ccttgcgtat tttacggtga ctattatgga atcccgaaat acaatattcc aggattaaaa  1140
agcaaaatcg acccgctttt aattgctcgt cgggactatg cctatggaac acaacgtgat  1200
tacattgacc atcaagacat tattggatgg acacgcgaag gcattgatac aaaaccaaac  1260
tctggactgg cggctttaat taccgacggc cctggcggaa gcaaatggat gtatgtcggt  1320
aaaaaacatg ctggaaaagt attttatgat ttaaccggaa accgaagtga cacagtaacg  1380
attaatgcgg atggttgggg agaatttaaa gtaaacggag ctccgtttc gatttgggtg   1440 gctaaataa                                                          1449
```

```
<210> SEQ ID NO 45
<211> LENGTH: 482
<212> TYPE: PRT
<213> ORGANISM: Artificial Sequence
<220> FEATURE:
<223> OTHER INFORMATION: Synthetically generated

<400> SEQUENCE: 45

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95
```

-continued

```
Ile Gln Val Tyr Ala Asp Val Val Phe Asn His Lys Ala Gly Ala Asp
                100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Glu Ala
                325                 330                 335

Leu Glu Ser Phe Val Gln Gly Trp Phe Lys Pro Leu Ala Tyr Ala Phe
            340                 345                 350

Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys
```

<210> SEQ ID NO 46
<211> LENGTH: 1449
<212> TYPE: DNA
<213> ORGANISM: Artificial Sequence
<220> FEATURE:
<223> OTHER INFORMATION: Synthetically generated

<400> SEQUENCE: 46

```
aatactgcac ctattaacga aacaatgatg caatattttg aatgggattt accgaacgat     60
ggaacccttt ggacaaaggt gaaaaatgaa gccgcaaatc tttcttcgct cggtattaca    120
gcgttatggc ttcctccagc gtataaagga acaagtcaaa gcgatgtcgg atacggcgtg    180
tacgatttat atgaccttgg ggaatttaat caaaaaggaa cgattcgaac aaaatacgga    240
acaaaaacac aactggaacg cgcaattaga tccttaaaag ctaacggaat ccaagtatat    300
gcagatgttg tctttaatca taaggcggga gctgacggca cagaatttgt cgatgcggtt    360
gaggtagacc cttctaatcg aaatcaagaa gtgagcggaa cgtatcaaat tgaagcatgg    420
acaaaatttg attttcccgg tcgggggaac acatactcga gttttaaatg gcgttggtat    480
cattttgacg gtaccgattg ggatgaaagc cgaaaattaa atcggattta caaattccgc    540
ggaaaagcat gggactggga agtcgataca gaaaacggaa actatgatta tttaatgttc    600
gctgatttag atatggatca ccctgaggtt gtgacagaat aaaaaaactg gggaacgtgg    660
tacgtcaata ctacaaatat cgatggattc cgcttagatg ccgtaaaaca tattaaattt    720
agttttatgc gggactggct aacatatgta cgtaatcaaa caggaaaaaa tttatttgcc    780
gttggggaat tttggagcta tgacgtcaat aagctgcata attacattac aaaaacaaat    840
ggatcgatgt cattatttga tgcacctttg cataacaact tttataccgc ttccaaatcg    900
agtggatatt ttgacatgcg ttatttattg aataatacat taatgaaaga tcaaccttca    960
ctcgctgtga cacttgtcga taaccacgac acacaaccgg gagaagcgct ggaatcattt   1020
gttcaaggat ggtttaaacc acttgcttac gcctttattt taacgagaca agagggatat   1080
ccttgcgtat tttacggtga ctattatgga atcccgaaat acaatattcc aggattaaaa   1140
agcaaaatcg acccgctttt aattgctcgt cgggactatg cctatggaac acaacgtgat   1200
tacattgacc atcaagacat tattggatgg acacgcgaag gcattgatac aaaaccaaac   1260
tctggactgg cggctttaat taccgacggc cctggcggaa gcaaatggat gtatgtcggt   1320
aaaaaacatg ctggaaaagt attttatgat ttaaccggaa accgaagtga cacagtaacg   1380
attaatgcgg atggttgggg agaatttaaa gtaaacggag gctccgtttc gatttgggtg   1440
gctaaataa                                                           1449
```

<210> SEQ ID NO 47
<211> LENGTH: 482
<212> TYPE: PRT
<213> ORGANISM: Artificial Sequence
<220> FEATURE:
<223> OTHER INFORMATION: Synthetically generated

<400> SEQUENCE: 47

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80
```

```
Thr Lys Thr Gln Leu Glu Arg Ala Ile Arg Ser Leu Lys Ala Asn Gly
                 85                  90                  95

Ile Gln Val Tyr Ala Asp Val Val Phe Asn His Lys Ala Gly Ala Asp
                100                 105                 110

Gly Thr Glu Phe Val Asp Ala Val Glu Val Asp Pro Ser Asn Arg Asn
                115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
                195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Tyr
225                 230                 235                 240

Ser Phe Phe Pro Asp Trp Leu Gly His Val Arg Gly Gln Thr Gly Lys
                245                 250                 255

Asn Leu Phe Ala Val Gly Glu Phe Trp Ser Tyr Asp Val Asn Lys Leu
                260                 265                 270

His Asn Tyr Ile Thr Lys Thr Asn Gly Ser Met Ser Leu Phe Asp Ala
                275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Glu Ala
                325                 330                 335

Leu Glu Ser Phe Val Gln Gly Trp Phe Lys Pro Leu Ala Tyr Ala Phe
                340                 345                 350

Ile Leu Thr Arg Gln Glu Gly Tyr Pro Cys Val Phe Tyr Gly Asp Tyr
                355                 360                 365

Tyr Gly Ile Pro Lys Tyr Asn Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys
```

<210> SEQ ID NO 48
<211> LENGTH: 1449
<212> TYPE: DNA
<213> ORGANISM: Artificial Sequence
<220> FEATURE:
<223> OTHER INFORMATION: Synthetically generated

<400> SEQUENCE: 48

```
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat aaaaaaactg gggaacgtgg     660
tacgtcaata ctacaaatat cgatggattc cgcttagatg ccgtaaaaca tattaaatac     720
agctttttcc ctgactggct aggccacgtt cgaggtcaaa caggtaaaaa cctttttgcc     780
gttggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acacaaccgg gagaagcgct ggaatcattt    1020
gttcaaggat ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                             1449
```

<210> SEQ ID NO 49
<211> LENGTH: 482
<212> TYPE: PRT
<213> ORGANISM: Artificial Sequence
<220> FEATURE:
<223> OTHER INFORMATION: Synthetically generated

<400> SEQUENCE: 49

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
```

```
              50                 55                 60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gln Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
                260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Glu Ala
                325                 330                 335

Leu Glu Ser Phe Val Gln Gly Trp Phe Lys Pro Leu Ala Tyr Ala Phe
                340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480
```

Ala Lys

<210> SEQ ID NO 50
<211> LENGTH: 1449
<212> TYPE: DNA
<213> ORGANISM: Artificial Sequence
<220> FEATURE:
<223> OTHER INFORMATION: Synthetically generated

<400> SEQUENCE: 50
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg taatttgctg aacggaacgc ttgtccaacg acacccttct     960
cacgctgtga cacttgtcga taaccacgac acacaaccgg gagaagcgct ggaatcattt    1020
gttcaaggat ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag ctccgtttc gatttgggtg     1440 gctaaataa                                                            1449

<210> SEQ ID NO 51
<211> LENGTH: 482
<212> TYPE: PRT
<213> ORGANISM: Artificial Sequence
<220> FEATURE:
<223> OTHER INFORMATION: Synthetically generated

<400> SEQUENCE: 51

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

```
Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Lys Asn Asp Leu Gly Ala Leu
            260                 265                 270

Glu Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
```

```
        450                455                460
Gly Trp Gly Glu Phe Lys Val Asn Gly Gly Ser Val Ser Ile Trp Val
465                470                475                480

Ala Lys

<210> SEQ ID NO 52
<211> LENGTH: 1449
<212> TYPE: DNA
<213> ORGANISM: Artificial Sequence
<220> FEATURE:
<223> OTHER INFORMATION: Synthetically generated

<400> SEQUENCE: 52
aatactgcac ctattaacga aacaatgatg caatattttg aatgggattt accgaacgat        60
ggaacccttt ggacaaaggt gaaaaatgaa gccgcaaatc tttcttcgct cggtattaca       120
gcgttatggc ttcctccagc gtataaagga acaagtcaaa gcgatgtcgg atacggcgtg       180
tacgatttat atgaccttgg ggaatttaat caaaaaggaa cgattcgaac aaaatacgga       240
acaaaaacac aatatattca agccatccaa gctgccaaag ccgcagggat gcaagtatat       300
gcagatgttg tctttaatca taaggcagga gcggaccaaa cagaatttgt cgatgcggtt       360
gaggtagacc cttctaatcg aaatcaagaa gtgagcggaa cgtatcaaat tgaagcatgg       420
acaaaatttg attttcccgg tcggggaac acatactcga gttttaaatg gcgttggtat       480
cattttgacg gtaccgattg ggatgaaagc cgaaaattaa atcggattta caaattccgc       540
ggaaaagcat gggactggga agtcgataca gaaaacggaa actatgatta tttaatgttc       600
gctgatttag atatggatca ccctgaggtt gtgacagaat taaaaaactg gggaacgtgg       660
tacgtcaata ctacaaatat cgatggattc cgcttagatg ccgtaaaaca tattaaattt       720
agttttatgc gggactggct aacatatgta cgtaatcaaa caggaaaaaa tttatttgcc       780 gttgggaat tttggaaaaa tgatttgggc gcgctcgaga attacattac aaaaacaaat       840
ggatcgatgt cattatttga tgcaccttg cataacaact tttataccgc ttccaaatcg       900
agtggatatt ttgacatgcg taatttgctg aacggaacgc ttgtccaacg acacccttct       960
cacgctgtga cacttgtcga taaccacgac acgcaaccag ggaatctttt acagtcatgg      1020 gtcgaaccttt ggtttaaacc acttgcttac gcctttattt taacgagaca agagggatat      1080
ccttgcgtat tttacggtga ctattatgga atcccgaaat acaatattcc aggattaaaa      1140
agcaaaatcg acccgctttt aattgctcgt cgggactatg cctatggaac acaacgtgat      1200
tacattgacc atcaagacat tattggatgg acacgcgaag gcattgatac aaaaccaaac      1260
tctggactgg cggctttaat taccgacggc cctggcggaa gcaaatggat gtatgtcggt      1320
aaaaaacatg ctggaaaagt attttatgat ttaaccggaa accgaagtga cacagtaacg      1380
attaatgcgg atggttgggg agaatttaaa gtaaacggag gctccgtttc gatttgggtg      1440
gctaaataa                                                             1449

<210> SEQ ID NO 53
<211> LENGTH: 482
<212> TYPE: PRT
<213> ORGANISM: Artificial Sequence
<220> FEATURE:
<223> OTHER INFORMATION: Synthetically generated

<400> SEQUENCE: 53

Asn Thr Ala Pro Ile Asn Glu Thr Met Met Gln Tyr Phe Glu Trp Asp
1                5                10                15
```

```
Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
            50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gln Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
                260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Ser Asp Gly Val Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430
```

Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys

<210> SEQ ID NO 54
<211> LENGTH: 1449
<212> TYPE: DNA
<213> ORGANISM: Artificial Sequence
<220> FEATURE:
<223> OTHER INFORMATION: Synthetically generated

<400> SEQUENCE: 54
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780 gttgggggaat tttggagcta tgacgtcaat aagctgcata attacattac aaaaaacaaat     840 ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acgcaaccag ggcaatcttt acagtcatgg    1020
gtcgaacctt ggtttaaacc acttgcttac gcctttattt taacgagaca agagggatat    1080
ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag cattgatac aaaaccaaac    1260 tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag ctccgtttc gatttgggtg    1440 gctaaataa                                                            1449

<210> SEQ ID NO 55
<211> LENGTH: 482
<212> TYPE: PRT
<213> ORGANISM: Artificial Sequence
<220> FEATURE:
<223> OTHER INFORMATION: Synthetically generated

```
<400> SEQUENCE: 55

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gln Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Tyr
225                 230                 235                 240

Ser Phe Phe Pro Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Glu Ala
                325                 330                 335

Leu Glu Ser Phe Val Gln Gly Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415
```

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys

<210> SEQ ID NO 56
<211> LENGTH: 1449
<212> TYPE: DNA
<213> ORGANISM: Artificial Sequence
<220> FEATURE:
<223> OTHER INFORMATION: Synthetically generated

<400> SEQUENCE: 56
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaatac     720
agctttttcc ctgactggct aacatatgta cgtaatcaaa caggaaaaaa tttatttgcc     780 gttgggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acacaaccgg gagaagcgct ggaatcattt    1020
gttcaaggat ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                            1449

<210> SEQ ID NO 57
<211> LENGTH: 482
<212> TYPE: PRT

<213> ORGANISM: Artificial Sequence
<220> FEATURE:
<223> OTHER INFORMATION: Synthetically generated

<400> SEQUENCE: 57

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
            165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
            245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
            325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
        355                 360                 365

Tyr Gly Ile Pro Ser Asp Gly Val Pro Gly Leu Lys Ser Lys Ile Asp
    370                 375                 380

Pro Leu Leu Ile Ala Arg Arg Asp Tyr Ala Tyr Gly Thr Gln Arg Asp

-continued

```
385              390              395              400

Tyr Ile Asp His Gln Asp Ile Ile Gly Trp Thr Arg Glu Gly Ile Asp
            405              410              415

Thr Lys Pro Asn Ser Gly Leu Ala Ala Leu Ile Thr Asp Gly Pro Gly
            420              425              430

Gly Ser Lys Trp Met Tyr Val Gly Lys Lys His Ala Gly Lys Val Phe
            435              440              445

Tyr Asp Leu Thr Gly Asn Arg Ser Asp Thr Val Thr Ile Asn Ala Asp
    450              455              460

Gly Trp Gly Glu Phe Lys Val Asn Gly Gly Ser Val Ser Ile Trp Val
465              470              475              480

Ala Lys
```

```
<210> SEQ ID NO 58
<211> LENGTH: 1449
<212> TYPE: DNA
<213> ORGANISM: Artificial Sequence
<220> FEATURE:
<223> OTHER INFORMATION: Synthetically generated

<400> SEQUENCE: 58
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg taatttgctg aacggaacgc ttgtccaacg acaccctctt     960
cacgctgtga cacttgtcga taaccacgac acgcaaccag gcaatcttt acagtcatgg    1020 gtcgaacctt ggtttaaacc acttgcttac gcctttattt taacgagaca gagggatat    1080 ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt atttttatgat ttaaccggaa accgaagtga cacagtaacg    1380
attaatgcgg atggttgggg agaatttaaa gtaaacggag gctccgtttc gatttgggtg    1440
gctaaataa                                                           1449
```

-continued

<210> SEQ ID NO 59
<211> LENGTH: 482
<212> TYPE: PRT
<213> ORGANISM: Artificial Sequence
<220> FEATURE:
<223> OTHER INFORMATION: Synthetically generated

<400> SEQUENCE: 59

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
            85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
            165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
            245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
            325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

```
Tyr Gly Ile Pro Ser Asp Gly Val Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys
```

<210> SEQ ID NO 60
<211> LENGTH: 1449
<212> TYPE: DNA
<213> ORGANISM: Artificial Sequence
<220> FEATURE:
<223> OTHER INFORMATION: Synthetically generated

<400> SEQUENCE: 60

```
aatactgcac ctattaacga acaatgatg caatattttg aatgggattt accgaacgat        60
ggaacccttt ggacaaaggt gaaaaatgaa gccgcaaatc tttcttcgct cggtattaca       120
gcgttatggc ttcctccagc gtataaagga acaagtcaaa gcgatgtcgg atacggcgtg       180
tacgatttat atgaccttgg ggaatttaat caaaaaggaa cgattcgaac aaaatacgga       240
acaaaaacac aactggaacg cgcaattaga tccttaaaag ctaacggaat ccaagtatat       300
gcagatgttg tctttaatca taaggcggga gctgacggca cagaatttgt cgatgcggtt       360
gaggtagacc cttctaatcg aaatcaagaa gtgagcggaa cgtatcaaat tgaagcatgg       420
acaaaatttg attttcccgg tcggggaac acatactcga gttttaaatg gcgttggtat       480
cattttgacg gtaccgattg ggatgaaagc cgaaaattaa atcggattta caaattccgc       540
ggaaaagcat gggactggga agtcgataca gaaaacggaa actatgatta tttaatgttc       600
gctgatttag atatggatca ccctgaggtt gtgacagaat taaaaaactg gggaacgtgg       660
tacgtcaata ctacaaatat cgatggattc cgcttagatg ccgtaaaaca tattaaattt       720
agttttatgc gggactggct aacatatgta cgtaatcaaa caggaaaaaa tttatttgcc       780
gttggggaat tttggagcta tgacgtcaat aagctgcata attacattac aaaaacaaat       840
ggatcgatgt cattatttga tgcacctttg cataacaact tttataccgc ttccaaatcg       900
agtggatatt ttgacatgcg ttatttattg aataatacat taatgaaaga tcaaccttca       960
ctcgctgtga cacttgtcga taaccacgac acgcaaccag gcaatcttt acagtcatgg      1020 gtcgaacctt ggtttaaacc acttgcttac gcctttattt taacgagaca agagggatat      1080
ccttgcgtat tttacggtga ctattatgga atcccgagcg atggcgtccc aggattaaaa      1140
agcaaaatcg acccgctttt aattgctcgt cgggactatg cctatggaac acaacgtgat      1200
tacattgacc atcaagacat tattggatgg acacgcgaag gcattgatac aaaaccaaac      1260
tctggactgg cggctttaat taccgacggc cctggcggaa gcaaatggat gtatgtcggt      1320
aaaaaacatg ctggaaaagt attttatgat ttaaccggaa accgaagtga cacagtaacg      1380
```

-continued

```
attaatgcgg atggttgggg agaatttaaa gtaaacggag gctccgtttc gatttgggtg      1440
gctaaataa                                                              1449
```

```
<210> SEQ ID NO 61
<211> LENGTH: 482
<212> TYPE: PRT
<213> ORGANISM: Artificial Sequence
<220> FEATURE:
<223> OTHER INFORMATION: Synthetically generated

<400> SEQUENCE: 61

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350
```

-continued

```
Ile Leu Thr Arg Gln Glu Gly Tyr Pro Cys Val Phe Tyr Gly Asp Tyr
        355                 360                 365

Tyr Gly Ile Pro Ser Asp Gly Val Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys

<210> SEQ ID NO 62
<211> LENGTH: 1449
<212> TYPE: DNA
<213> ORGANISM: Artificial Sequence
<220> FEATURE:
<223> OTHER INFORMATION: Synthetically generated

<400> SEQUENCE: 62
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat aaaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg taatttgctg aacggaacgc ttgtccaacg acacccttct     960
cacgctgtga cacttgtcga taaccacgac acgcaaccag gcaatctttt acagtcatgg    1020
gtcgaacctt ggtttaaacc acttgcttac gcctttattt taacgagaca agagggtatt    1080
ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
```

-continued

```
tctggactgg cggctttaat taccgacggc cctggcggaa gcaaatggat gtatgtcggt      1320
aaaaaacatg ctggaaaagt attttatgat ttaaccggaa accgaagtga cacagtaacg      1380
attaatgcgg atggttgggg agaatttaaa gtaaacggag gctccgtttc gatttgggtg      1440
gctaaataa                                                              1449
```

<210> SEQ ID NO 63
<211> LENGTH: 482
<212> TYPE: PRT
<213> ORGANISM: Artificial Sequence
<220> FEATURE:
<223> OTHER INFORMATION: Synthetically generated

<400> SEQUENCE: 63

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Gly His Val Arg Gly Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
```

-continued

```
                 325              330              335

Leu Gln Ser Trp Val Glu Pro Trp Phe Lys Pro Leu Ala Tyr Ala Phe
            340              345              350

Ile Leu Thr Arg Gln Glu Gly Tyr Pro Cys Val Phe Tyr Gly Asp Tyr
            355              360              365

Tyr Gly Ile Pro Lys Tyr Asn Ile Pro Gly Leu Lys Ser Lys Ile Asp
        370              375              380

Pro Leu Leu Ile Ala Arg Arg Asp Tyr Ala Tyr Gly Thr Gln Arg Asp
385              390              395              400

Tyr Ile Asp His Gln Asp Ile Ile Gly Trp Thr Arg Glu Gly Ile Asp
                405              410              415

Thr Lys Pro Asn Ser Gly Leu Ala Ala Leu Ile Thr Asp Gly Pro Gly
            420              425              430

Gly Ser Lys Trp Met Tyr Val Gly Lys Lys His Ala Gly Lys Val Phe
            435              440              445

Tyr Asp Leu Thr Gly Asn Arg Ser Asp Thr Val Thr Ile Asn Ala Asp
        450              455              460

Gly Trp Gly Glu Phe Lys Val Asn Gly Gly Ser Val Ser Ile Trp Val
465              470              475              480

Ala Lys
```

```
<210> SEQ ID NO 64
<211> LENGTH: 1449
<212> TYPE: DNA
<213> ORGANISM: Artificial Sequence
<220> FEATURE:
<223> OTHER INFORMATION: Synthetically generated

<400> SEQUENCE: 64
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat aaaaaaactg gggaacgtgg     660
tacgtcaata ctacaaatat cgatggattc cgcttagatg ccgtaaaaca tattaaattt     720
agttttatgc gggactggct aggccacgtt cgaggtcaaa caggtaaaaa ccttttttgcc     780 gttggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acgcaaccag ggcaatcttt acagtcatgg    1020
gtcgaacctt ggtttaaacc acttgcttac gcctttattt taacgagaca agagggatat    1080
ccttgcgtat tttacggtga ctattatgga atcccgaaat acaatattcc aggattaaaa    1140
```

-continued

```
agcaaaatcg accccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                            1449
```

<210> SEQ ID NO 65
<211> LENGTH: 482
<212> TYPE: PRT
<213> ORGANISM: Artificial Sequence
<220> FEATURE:
<223> OTHER INFORMATION: Synthetically generated

<400> SEQUENCE: 65

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Tyr
225                 230                 235                 240

Ser Phe Phe Pro Asp Trp Leu Thr Tyr Val Arg Asn Gln Thr Gly Lys
                245                 250                 255

Asn Leu Phe Ala Val Gly Glu Phe Trp Lys Asn Asp Leu Gly Ala Leu
            260                 265                 270

Glu Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300
```

-continued

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys

<210> SEQ ID NO 66
<211> LENGTH: 1449
<212> TYPE: DNA
<213> ORGANISM: Artificial Sequence
<220> FEATURE:
<223> OTHER INFORMATION: Synthetically generated

<400> SEQUENCE: 66
aatactgcac ctattaacga aacaatgatg caatattttg aatgggattt accgaacgat       60
ggaacccttt ggacaaaggt gaaaaatgaa gccgcaaatc tttcttcgct cggtattaca      120
gcgttatggc ttcctccagc gtataaagga acaagtcaaa gcgatgtcgg atacggcgtg      180
tacgatttat atgaccttgg ggaatttaat caaaaaggaa cgattcgaac aaaatacgga      240
acaaaaacac aatatattca agccatccaa gctgccaaag ccgcagggat gcaagtatat      300
gcagatgttg tctttaatca taaggcagga gcggaccaaa cagaatttgt cgatgcggtt      360
gaggtagacc cttctaatcg aaatcaagaa gtgagcggaa cgtatcaaat tgaagcatgg      420
acaaaatttg attttcccgg tcggggaac acatactcga gttttaaatg cgttggtat      480 cattttgacg gtaccgattg ggatgaaagc cgaaaattaa atcggattta caaattccgc      540
ggaaaagcat gggactggga agtcgataca gaaaacggaa actatgatta tttaatgttc      600
gctgatttag atatggatca ccctgaggtt gtgacagaat aaaaaaactg gggaacgtgg      660
tacgtcaata ctacaaatat cgatggattc cgcttagatg ccgtaaaaca tattaaatac      720
agctttttcc ctgactggct aacatatgta cgtaatcaaa caggaaaaaa tttatttgcc      780
gttggggaat tttggaaaaa tgatttgggc gcgctcgaga attacattac aaaaacaaat      840
ggatcgatgt cattatttga tgcacctttg cataacaact tttataccgc ttccaaatcg      900
agtggatatt ttgacatgcg taatttgctg aacggaacgc ttgtccaacg acacccttct      960
cacgctgtga cacttgtcga taaccacgac acgcaaccag gcaatctttt acagtcatgg     1020

```
gtcgaacctt ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                             1449
```

<210> SEQ ID NO 67
<211> LENGTH: 482
<212> TYPE: PRT
<213> ORGANISM: Artificial Sequence
<220> FEATURE:
<223> OTHER INFORMATION: Synthetically generated

<400> SEQUENCE: 67

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
        275                 280                 285
```

```
Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Glu Ala
                325                 330                 335

Leu Glu Ser Phe Val Gln Gly Trp Phe Lys Pro Leu Ala Tyr Ala Phe
                340                 345                 350

Ile Leu Thr Arg Gln Glu Gly Tyr Pro Cys Val Phe Tyr Gly Asp Tyr
                355                 360                 365

Tyr Gly Ile Pro Ser Asp Gly Val Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
                435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys
```

```
<210> SEQ ID NO 68
<211> LENGTH: 1449
<212> TYPE: DNA
<213> ORGANISM: Artificial Sequence
<220> FEATURE:
<223> OTHER INFORMATION: Synthetically generated

<400> SEQUENCE: 68
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcggggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat aaaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780 gttgggggaat tttggagcta tgacgtcaat aagctgcata attacattac aaaaacaaat     840
ggatcgatgt cattatttga tgcacctttg cataacaact tttataccgc ttccaaatcg     900
```

-continued

```
agtggatatt ttgacatgcg ttatttattg aataatacat taatgaaaga tcaaccttca    960
ctcgctgtga cacttgtcga taaccacgac acacaaccgg gagaagcgct ggaatcattt    1020
gttcaaggat ggtttaaacc acttgcttac gcctttattt taacgagaca agagggatat    1080
ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                            1449
```

<210> SEQ ID NO 69
<211> LENGTH: 482
<212> TYPE: PRT
<213> ORGANISM: Artificial Sequence
<220> FEATURE:
<223> OTHER INFORMATION: Synthetically generated

<400> SEQUENCE: 69

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Gly His Val Arg Gly Gln Thr Gly Lys
                245                 250                 255

Asn Leu Phe Ala Val Gly Glu Phe Trp Ser Tyr Asp Val Asn Lys Leu
```

```
              260               265               270
His Asn Tyr Ile Thr Lys Thr Asn Gly Ser Met Ser Leu Phe Asp Ala
        275               280               285

Pro Leu His Asn Asn Phe Tyr Thr Ala Ser Lys Ser Ser Gly Tyr Phe
        290               295               300

Asp Met Arg Tyr Leu Leu Asn Asn Thr Leu Met Lys Asp Gln Pro Ser
305               310               315               320

Leu Ala Val Thr Leu Val Asp Asn His Asp Thr Gln Pro Gly Glu Ala
            325               330               335

Leu Glu Ser Phe Val Gln Gly Trp Phe Lys Pro Leu Ala Tyr Ala Phe
            340               345               350

Ile Leu Thr Arg Gln Glu Gly Tyr Pro Cys Val Phe Tyr Gly Asp Tyr
            355               360               365

Tyr Gly Ile Pro Lys Tyr Asn Ile Pro Gly Leu Lys Ser Lys Ile Asp
        370               375               380

Pro Leu Leu Ile Ala Arg Arg Asp Tyr Ala Tyr Gly Thr Gln Arg Asp
385               390               395               400

Tyr Ile Asp His Gln Asp Ile Ile Gly Trp Thr Arg Glu Gly Ile Asp
            405               410               415

Thr Lys Pro Asn Ser Gly Leu Ala Ala Leu Ile Thr Asp Gly Pro Gly
            420               425               430

Gly Ser Lys Trp Met Tyr Val Gly Lys Lys His Ala Gly Lys Val Phe
            435               440               445

Tyr Asp Leu Thr Gly Asn Arg Ser Asp Thr Val Thr Ile Asn Ala Asp
        450               455               460

Gly Trp Gly Glu Phe Lys Val Asn Gly Gly Ser Val Ser Ile Trp Val
465               470               475               480

Ala Lys
```

```
<210> SEQ ID NO 70
<211> LENGTH: 1449
<212> TYPE: DNA
<213> ORGANISM: Artificial Sequence
<220> FEATURE:
<223> OTHER INFORMATION: Synthetically generated

<400> SEQUENCE: 70
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcggggaac acatactcga gttttaaatg gcgttggtat     480
cattttgacg gtaccgattg ggatgaaagc cgaaaattaa atcggattta caattccgc     540 ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aggccacgtt cgaggtcaaa caggtaaaaa cctttttgcc     780
```

-continued

```
gttgggggaat tttggagcta tgacgtcaat aagctgcata attacattac aaaaacaaat      840
ggatcgatgt cattatttga tgcacctttg cataacaact tttataccgc ttccaaatcg      900
agtggatatt ttgacatgcg ttatttattg aataatacat taatgaaaga tcaaccttca      960
ctcgctgtga cacttgtcga taaccacgac acacaaccgg gagaagcgct ggaatcattt     1020
gttcaaggat ggtttaaacc acttgcttac gcctttattt taacgagaca agagggatat     1080
ccttgcgtat tttacggtga ctattatgga atcccgaaat acaatattcc aggattaaaa     1140
agcaaaatcg acccgctttt aattgctcgt cgggactatg cctatggaac acaacgtgat     1200
tacattgacc atcaagacat tattggatgg acacgcgaag gcattgatac aaaaccaaac     1260
tctggactgg cggctttaat taccgacggc cctggcggaa gcaaatggat gtatgtcggt     1320
aaaaaacatg ctggaaaagt attttatgat ttaaccggaa accgaagtga cacagtaacg     1380
attaatgcgg atggttgggg agaatttaaa gtaaacggag gctccgtttc gatttgggtg     1440
gctaaataa                                                             1449
```

```
<210> SEQ ID NO 71
<211> LENGTH: 482
<212> TYPE: PRT
<213> ORGANISM: Artificial Sequence
<220> FEATURE:
<223> OTHER INFORMATION: Synthetically generated

<400> SEQUENCE: 71

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240
```

```
Ser Phe Met Arg Asp Trp Leu Thr Tyr Val Arg Asn Gln Thr Gly Lys
            245             250             255

Asn Leu Phe Ala Val Gly Glu Phe Trp Ser Tyr Asp Val Asn Lys Leu
            260             265             270

His Asn Tyr Ile Thr Lys Thr Asn Gly Ser Met Ser Leu Phe Asp Ala
            275             280             285

Pro Leu His Asn Asn Phe Tyr Thr Ala Ser Lys Ser Ser Gly Tyr Phe
    290             295             300

Asp Met Arg Tyr Leu Leu Asn Asn Thr Leu Met Lys Asp Gln Pro Ser
305             310             315             320

Leu Ala Val Thr Leu Val Asp Asn His Asp Thr Gln Pro Gly Gln Ser
            325             330             335

Leu Gln Ser Trp Val Glu Pro Trp Phe Lys Pro Leu Ala Tyr Ala Phe
            340             345             350

Ile Leu Thr Arg Gln Glu Gly Tyr Pro Cys Val Phe Tyr Gly Asp Tyr
            355             360             365

Tyr Gly Ile Pro Lys Tyr Asn Ile Pro Gly Leu Lys Ser Lys Ile Asp
    370             375             380

Pro Leu Leu Ile Ala Arg Arg Asp Tyr Ala Tyr Gly Thr Gln Arg Asp
385             390             395             400

Tyr Ile Asp His Gln Asp Ile Ile Gly Trp Thr Arg Glu Gly Ile Asp
            405             410             415

Thr Lys Pro Asn Ser Gly Leu Ala Ala Leu Ile Thr Asp Gly Pro Gly
            420             425             430

Gly Ser Lys Trp Met Tyr Val Gly Lys Lys His Ala Gly Lys Val Phe
            435             440             445

Tyr Asp Leu Thr Gly Asn Arg Ser Asp Thr Val Thr Ile Asn Ala Asp
    450             455             460

Gly Trp Gly Glu Phe Lys Val Asn Gly Gly Ser Val Ser Ile Trp Val
465             470             475             480

Ala Lys
```

<210> SEQ ID NO 72
<211> LENGTH: 1449
<212> TYPE: DNA
<213> ORGANISM: Artificial Sequence
<220> FEATURE:
<223> OTHER INFORMATION: Synthetically generated

<400> SEQUENCE: 72

```
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat aaaaaactg gggaacgtgg      660
```

-continued

```
tacgtcaata ctacaaatat cgatggattc cgcttagatg ccgtaaaaca tattaaattt    720
agttttatgc gggactggct aacatatgta cgtaatcaaa caggaaaaaa tttatttgcc    780
gttggggaat tttggagcta tgacgtcaat aagctgcata attacattac aaaaacaaat    840
ggatcgatgt cattatttga tgcacctttg cataacaact tttataccgc ttccaaatcg    900
agtggatatt ttgacatgcg ttatttattg aataatacat taatgaaaga tcaaccttca    960
ctcgctgtga cacttgtcga taaccacgac acgcaaccag ggcaatcttt acagtcatgg   1020
gtcgaacctt ggtttaaacc acttgcttac gcctttattt taacgagaca agagggatat   1080
ccttgcgtat tttacggtga ctattatgga atcccgaaat acaatattcc aggattaaaa   1140
agcaaaatcg acccgctttt aattgctcgt cgggactatg cctatggaac acaacgtgat   1200
tacattgacc atcaagacat tattggatgg acacgcgaag gcattgatac aaaaccaaac   1260
tctggactgg cggctttaat taccgacggc cctggcggaa gcaaatggat gtatgtcggt   1320
aaaaaacatg ctggaaaagt attttatgat ttaaccggaa accgaagtga cacagtaacg   1380
attaatgcgg atggttgggg agaatttaaa gtaaacggag gctccgtttc gatttgggtg   1440
gctaaataa                                                           1449
```

```
<210> SEQ ID NO 73
<211> LENGTH: 482
<212> TYPE: PRT
<213> ORGANISM: Artificial Sequence
<220> FEATURE:
<223> OTHER INFORMATION: Synthetically generated

<400> SEQUENCE: 73

Asn Thr Ala Pro Ile Asn Glu Thr Met Met Gln Tyr Phe Glu Trp Asp
1               5                  10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220
```

-continued

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
                260                 265                 270

His Asn Tyr Ile Thr Lys Thr Asn Gly Ser Met Ser Leu Phe Asp Ala
                275                 280                 285

Pro Leu His Asn Asn Phe Tyr Thr Ala Ser Lys Ser Ser Gly Tyr Phe
                290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
                340                 345                 350

Ile Leu Thr Arg Gln Glu Gly Tyr Pro Cys Val Phe Tyr Gly Asp Tyr
                355                 360                 365

Tyr Gly Ile Pro Lys Tyr Asn Ile Pro Gly Leu Lys Ser Lys Ile Asp
                370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
                435                 440                 445

Tyr Asp Leu Thr Gly Asn Arg Ser Asp Thr Val Thr Ile Asn Ala Asp
                450                 455                 460

Gly Trp Gly Glu Phe Lys Val Asn Gly Gly Ser Val Ser Ile Trp Val
465                 470                 475                 480

Ala Lys

<210> SEQ ID NO 74
<211> LENGTH: 1449
<212> TYPE: DNA
<213> ORGANISM: Artificial Sequence
<220> FEATURE:
<223> OTHER INFORMATION: Synthetically generated

<400> SEQUENCE: 74
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcggggaac acatactcga gttttaaatg gcgttggtat     480
cattttgacg gtaccgattg ggatgaaagc cgaaaattaa atcggattta caaattccgc     540

-continued

```
ggaaaagcat gggactggga agtcgataca gaaaacggaa actatgatta tttaatgttc      600
gctgatttag atatggatca ccctgaggtt gtgacagaat taaaaaactg gggaacgtgg      660
tacgtcaata ctacaaatat cgatggattc cgcttagatg ccgtaaaaca tattaaattt      720
agttttatgc gggactggct aacatatgta cgtaatcaaa caggaaaaaa tttatttgcc      780
gttggggaat tttggagcta tgacgtcaat aagctgcata attacattac aaaaacaaat      840
ggatcgatgt cattatttga tgcacctttg cataacaact tttataccgc ttccaaatcg      900
agtggatatt ttgacatgcg ttatttattg aataatacat taatgaaaga tcaaccttca      960
ctcgctgtga cacttgtcga taaccacgac acgcaaccag ggcaatcttt acagtcatgg     1020
gtcgaacctt ggtttaaacc acttgcttac gcctttattt taacgagaca agagggatat     1080
ccttgcgtat tttacggtga ctattatgga atcccgaaat acaatattcc aggattaaaa     1140
agcaaaatcg acccgctttt aattgctcgt cgggactatg cctatggaac acaacgtgat     1200
tacattgacc atcaagacat tattggatgg acacgcgaag cattgatac aaaaccaaac      1260 tctggactgg cggctttaat taccgacggc cctggcggaa gcaaatggat gtatgtcggt     1320
aaaaaacatg ctggaaaagt attttatgat ttaaccggaa accgaagtga cacagtaacg     1380
attaatgcgg atggttgggg agaatttaaa gtaaacggag gctccgtttc gatttgggtg     1440
gctaaataa                                                            1449
```

<210> SEQ ID NO 75
<211> LENGTH: 482
<212> TYPE: PRT
<213> ORGANISM: Artificial Sequence
<220> FEATURE:
<223> OTHER INFORMATION: Synthetically generated

<400> SEQUENCE: 75

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
```

```
            195                 200                 205
Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
                260                 265                 270

His Asn Tyr Ile Thr Lys Thr Asn Gly Ser Met Ser Leu Phe Asp Ala
                275                 280                 285

Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
                340                 345                 350

Ile Leu Thr Arg Gln Glu Gly Tyr Pro Cys Val Phe Tyr Gly Asp Tyr
                355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
                435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys
```

<210> SEQ ID NO 76
<211> LENGTH: 1449
<212> TYPE: DNA
<213> ORGANISM: Artificial Sequence
<220> FEATURE:
<223> OTHER INFORMATION: Synthetically generated

<400> SEQUENCE: 76

```
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggac cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
```

-continued

```
acaaaatttg attttcccgg tcgggggaac acatactcga gttttaaatg gcgttggtat   480
cattttgacg gtaccgattg ggatgaaagc cgaaaattaa atcggattta caaattccgc   540
ggaaaagcat gggactggga agtcgataca gaaaacggaa actatgatta tttaatgttc   600
gctgatttag atatggatca ccctgaggtt gtgacagaat taaaaaactg gggaacgtgg   660
tacgtcaata ctacaaatat cgatggattc cgcttagatg ccgtaaaaca tattaaattt   720
agttttatgc gggactggct aacatatgta cgtaatcaaa caggaaaaaa tttatttgcc   780
gttggggaat tttggagcta tgacgtcaat aagctgcata attacattac aaaaacaaat   840
ggatcgatgt cattatttga tgcacctttg cataacaact tttataccgc ttccaaatcg   900
agtggatatt ttgacatgcg ttatttattg aataatacat taatgaaaga tcaaccttca   960
ctcgctgtga cacttgtcga taaccacgac acgcaaccag ggcaatcttt acagtcatgg   1020
gtcgaacctt ggtttaaacc acttgcttac gcctttattt taacgagaca agagggatat   1080
ccttgcgtat tttacggtga ctattatgga atcccgaaat acaatattcc aggattaaaa   1140
agcaaaatcg acccgctttt aattgctcgt cgggactatg cctatggaac acaacgtgat   1200
tacattgacc atcaagacat tattggatgg acacgcgaag gcattgatac aaaaccaaac   1260
tctggactgg cggctttaat taccgacggc cctggcggaa gcaaatggat gtatgtcggt   1320
aaaaaacatg ctggaaaagt attttatgat ttaaccggaa accgaagtga cacagtaacg   1380
attaatgcgg atggttgggg agaatttaaa gtaaacggag gctccgtttc gatttgggtg   1440
gctaaataa                                                           1449
```

<210> SEQ ID NO 77
<211> LENGTH: 482
<212> TYPE: PRT
<213> ORGANISM: Artificial Sequence
<220> FEATURE:
<223> OTHER INFORMATION: Synthetically generated

<400> SEQUENCE: 77

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175
```

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys

<210> SEQ ID NO 78
<211> LENGTH: 1449
<212> TYPE: DNA
<213> ORGANISM: Artificial Sequence
<220> FEATURE:
<223> OTHER INFORMATION: Synthetically generated

<400> SEQUENCE: 78
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300

-continued

```
gcagatgttg tctttaatca taaggcagga gcggaccaaa cagaatttgt cgatgcggtt      360
gaggtagacc cttctaatcg aaatcaagaa acatctggaa catatcaaat tcaagcatgg      420
acaaaatttg attttcccgg tcgggggaac acatactcga gttttaaatg gcgttggtat      480
cattttgacg gtaccgattg ggatgaaagc cgaaaattaa atcggattta caaattccgc      540
ggaaaagcat gggactggga agtcgataca gaaaacggaa actatgatta tttaatgttc      600
gctgatttag atatggatca ccctgaggtt gtgacagaat aaaaaaactg gggaacgtgg      660
tacgtcaata ctacaaatat cgatggattc cgcttagatg ccgtaaaaca tattaaattt      720
agttttatgc gggactggct aacatatgta cgtaatcaaa caggaaaaaa tttatttgcc      780 gttgggggaat tttggagcta tgacgtcaat aagctgcata attacattac aaaaacaaat      840
ggatcgatgt cattatttga tgcacctttg cataacaact tttataccgc ttccaaatcg      900
agtggatatt ttgacatgcg ttatttattg aataatacat taatgaaaga tcaaccttca      960
ctcgctgtga cacttgtcga taaccacgac acgcaaccag ggcaatcttt acagtcatgg     1020
gtcgaacctt ggtttaaacc acttgcttac gcctttattt taacgagaca agagggatat     1080
ccttgcgtat tttacggtga ctattatgga atcccgaaat acaatattcc aggattaaaa     1140
agcaaaatcg acccgctttt aattgctcgt cgggactatg cctatggaac acaacgtgat     1200
tacattgacc atcaagacat tattggatgg acacgcgaag gcattgatac aaaaccaaac     1260
tctggactgg cggctttaat taccgacggc cctggcggaa gcaaatggat gtatgtcggt     1320
aaaaaacatg ctggaaaagt attttatgat ttaaccggaa accgaagtga cacagtaacg     1380
attaatgcgg atggttgggg agaatttaaa gtaaacggag gctccgtttc gatttgggtg     1440
gctaaataa                                                           1449
```

```
<210> SEQ ID NO 79
<211> LENGTH: 482
<212> TYPE: PRT
<213> ORGANISM: Artificial Sequence
<220> FEATURE:
<223> OTHER INFORMATION: Synthetically generated

<400> SEQUENCE: 79

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160
```

-continued

```
His Phe Asp Gly Thr Asp Trp Asp Glu Ser Arg Lys Leu Asn Arg Ile
            165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
            245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
            325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
            405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys
```

```
<210> SEQ ID NO 80
<211> LENGTH: 1449
<212> TYPE: DNA
<213> ORGANISM: Artificial Sequence
<220> FEATURE:
<223> OTHER INFORMATION: Synthetically generated

<400> SEQUENCE: 80
aatactgcac ctattaacga aacaatgatg caatattttg aatgggattt accgaacgat        60
ggaacccttt ggacaaaggt gaaaaatgaa gccgcaaatc tttcttcgct cggtattaca       120
gcgttatggc ttcctccagc gtataaagga acaagtcaaa gcgatgtcgg atacggcgtg       180
```

```
tacgatttat atgaccttgg ggaatttaat caaaaaggaa cgattcgaac aaaatacgga      240
acaaaaacac aatatattca agccatccaa gctgccaaag ccgcagggat gcaagtatat      300
gcagatgttg tctttaatca taaggcagga gcggaccaaa cagaatttgt cgatgcggtt      360
gaggtagacc cttctaatcg aaatcaagaa gtgagcggaa cgtatcaaat tgaagcatgg      420
acaaaatttg attttcccgg tcgggggaac acatactcga gttttaaatg gcgttggtat      480
cattttgacg gtaccgattg ggatgaaagc cgaaaattaa atcggattta caaattccgc      540
ggaaaagcat gggactggga agtcgataca gaaaacggaa actatgatta tttaatgttc      600
gctgatttag atatggatca ccctgaggtt gtgacagaat taaaaaactg gggaacgtgg      660
tacgtcaata ctacaaatat cgatggattc cgcttagatg ccgtaaaaca tattaaattt      720
agttttatgc gggactggct aacatatgta cgtaatcaaa caggaaaaaa tttatttgcc      780
gttggggaat tttggagcta tgacgtcaat aagctgcata attacattac aaaaacaaat      840
ggatcgatgt cattatttga tgcacctttg cataacaact tttataccgc ttccaaatcg      900
agtggatatt ttgacatgcg taatttgctg aacggaacgc ttgtccaacg acacccttct      960
cacgctgtga cacttgtcga taaccacgac acgcaaccag ggcaatcttt acagtcatgg     1020
gtcgaacctt ggtttaaacc acttgcttac gcctttattt taacgagaca agagggatat     1080
ccttgcgtat tttacggtga ctattatgga atcccgaaat acaatattcc aggattaaaa     1140
agcaaaatcg acccgctttt aattgctcgt cgggactatg cctatggaac acaacgtgat     1200
tacattgacc atcaagacat tattggatgg acacgcgaag gcattgatac aaaaccaaac     1260
tctggactgg cggctttaat taccgacggc cctggcggaa gcaaatggat gtatgtcggt     1320
aaaaaacatg ctggaaaagt attttatgat ttaaccggaa accgaagtga cacagtaacg     1380
attaatgcgg atggttgggg agaatttaaa gtaaacggag gctccgtttc gatttgggtg     1440
gctaaataa                                                            1449
```

```
<210> SEQ ID NO 81
<211> LENGTH: 482
<212> TYPE: PRT
<213> ORGANISM: Artificial Sequence
<220> FEATURE:
<223> OTHER INFORMATION: Synthetically generated

<400> SEQUENCE: 81

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
```

-continued

```
            130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
                195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
                260                 265                 270

His Asn Tyr Ile Thr Lys Thr Asn Gly Ser Met Ser Leu Phe Asp Ala
                275                 280                 285

Pro Leu His Asn Asn Phe Tyr Thr Ala Ser Lys Ser Ser Gly Tyr Phe
        290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
                340                 345                 350

Ile Leu Thr Arg Gln Glu Gly Tyr Pro Cys Val Phe Tyr Gly Asp Tyr
                355                 360                 365

Tyr Gly Ile Pro Lys Tyr Asn Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
                435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys
```

```
<210> SEQ ID NO 82
<211> LENGTH: 1449
<212> TYPE: DNA
<213> ORGANISM: Artificial Sequence
<220> FEATURE:
<223> OTHER INFORMATION: Synthetically generated

<400> SEQUENCE: 82
aatactgcac ctattaacga aacaatgatg caatattttg aatgggattt accgaacgat       60
```

```
ggaacccttt ggacaaaggt gaaaaatgaa gccgcaaatc tttcttcgct cggtattaca    120
gcgttatggc ttcctccagc gtataaagga acaagtcaaa gcgatgtcgg atacggcgtg    180
tacgatttat atgaccttgg ggaatttaat caaaaaggaa cgattcgaac aaaatacgga    240
acaaaaacac aatatattca agccatccaa gctgccaaag ccgcagggat gcaagtatat    300
gcagatgttg tctttaatca taaggcggga gctgacggca cagaatttgt cgatgcggtt    360
gaggtagacc cttctaatcg aaatcaagaa gtgagcggaa cgtatcaaat tgaagcatgg    420
acaaaatttg attttcccgg tcgggggaac acatactcga gttttaaatg gcgttggtat    480 catttttgacg gtaccgattg ggatgaaagc cgaaaattaa atcggattta caaattccgc    540
ggaaaagcat gggactggga agtcgataca gaaaacggaa actatgatta tttaatgttc    600
gctgatttag atatggatca ccctgaggtt gtgacagaat aaaaaaactg gggaacgtgg    660
tacgtcaata ctacaaatat cgatggattc cgcttagatg ccgtaaaaca tattaaattt    720
agttttatgc gggactggct aacatatgta cgtaatcaaa caggaaaaaa tttatttgcc    780
gttggggaat tttggagcta tgacgtcaat aagctgcata attacattac aaaaacaaat    840
ggatcgatgt cattatttga tgcacctttg cataacaact tttataccgc ttccaaatcg    900
agtggatatt ttgacatgcg taatttgctg aacggaacgc ttgtccaacg acacccttct    960
cacgctgtga cacttgtcga taaccacgac acgcaaccag ggcaatcttt acagtcatgg   1020
gtcgaacctt ggtttaaacc acttgcttac gcctttattt taacgagaca agagggtat   1080 ccttgcgtat tttacggtga ctattatgga atcccgaaat acaatattcc aggattaaaa   1140
agcaaaatcg acccgctttt aattgctcgt cgggactatg cctatggaac acaacgtgat   1200
tacattgacc atcaagacat tattggatgg acacgcgaag gcattgatac aaaaccaaac   1260
tctggactgg cggctttaat taccgacggc cctggcggaa gcaaatggat gtatgtcggt   1320
aaaaaacatg ctggaaaagt attttatgat ttaaccggaa accgaagtga cacagtaacg   1380
attaatgcgg atggttgggg agaatttaaa gtaaacggag gctccgtttc gatttgggtg   1440
gctaaataa                                                           1449
```

```
<210> SEQ ID NO 83
<211> LENGTH: 482
<212> TYPE: PRT
<213> ORGANISM: Artificial Sequence
<220> FEATURE:
<223> OTHER INFORMATION: Synthetically generated

<400> SEQUENCE: 83

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110
```

-continued

```
Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
                260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
        290                 295                 300

Asp Met Arg Tyr Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
                340                 345                 350

Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys
```

<210> SEQ ID NO 84
<211> LENGTH: 1449
<212> TYPE: DNA
<213> ORGANISM: Artificial Sequence
<220> FEATURE:
<223> OTHER INFORMATION: Synthetically generated

<400> SEQUENCE: 84
aatactgcac ctattaacga aacaatgatg caatattttg aatgggattt accgaacgat        60
ggaacccttt ggacaaaggt gaaaaatgaa gccgcaaatc tttcttcgct cggtattaca       120
gcgttatggc ttcctccagc gtataaagga acaagtcaaa gcgatgtcgg atacggcgtg       180
tacgatttat atgaccttgg ggaatttaat caaaaaggaa cgattcgaac aaaatacgga       240
acaaaaacac aatatattca agccatccaa gctgccaaag ccgcagggat gcaagtatat       300
gcagatgttg tctttaatca taaggcagga gcggaccaaa cagaatttgt cgatgcggtt       360
gaggtagacc cttctaatcg aaatcaagaa gtgagcggaa cgtatcaaat tgaagcatgg       420
acaaaatttg attttcccgg tcgggggaac acatactcga gttttaaatg gcgttggtat       480
cattttgacg gtaccgattg ggatgaaagc cgaaaattaa atcggattta caaattccgc       540
ggaaaagcat gggactggga agtcgataca gaaaacggaa actatgatta tttaatgttc       600
gctgatttag atatggatca ccctgaggtt gtgacagaat taaaaaactg gggaacgtgg       660
tacgtcaata ctacaaatat cgatggattc cgcttagatg ccgtaaaaca tattaaattt       720
agttttatgc gggactggct aacatatgta cgtaatcaaa caggaaaaaa tttatttgcc       780
gttggggaat tttggagcta tgacgtcaat aagctgcata attacattac aaaaacaaat       840
ggatcgatgt cattatttga tgcacctttg cataacaact tttataccgc ttccaaatcg       900
agtggatatt ttgacatgcg ttatttgctg aacggaacgc ttgtccaacg cacccttct       960 cacgctgtga cacttgtcga taaccacgac acgcaaccag ggcaatcttt acagtcatgg      1020
gtcgaacctt ggtttaaacc acttgcttac gcctttattt taacgagaca agagggatat      1080
ccttgcgtat tttacggtga ctattatgga atcccgaaat acaatattcc aggattaaaa      1140
agcaaaatcg acccgctttt aattgctcgt cgggactatg cctatggaac acaacgtgat      1200
tacattgacc atcaagacat tattggatgg acacgcgaag gcattgatac aaaaccaaac      1260
tctggactgg cggctttaat taccgacggc cctggcggaa gcaaatggat gtatgtcggt      1320
aaaaaacatg ctggaaaagt attttatgat ttaaccggaa accgaagtga cacagtaacg      1380
attaatgcgg atggttgggg agaatttaaa gtaaacggag ctccgtttc gatttgggtg      1440 gctaaataa                                                              1449

<210> SEQ ID NO 85
<211> LENGTH: 482
<212> TYPE: PRT
<213> ORGANISM: Artificial Sequence
<220> FEATURE:
<223> OTHER INFORMATION: Synthetically generated

<400> SEQUENCE: 85

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

```
Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
            130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
            210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
            290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Glu Ala
                325                 330                 335

Leu Glu Ser Phe Val Gln Gly Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
            370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
            450                 455                 460

Gly Trp Gly Glu Phe Lys Val Asn Gly Gly Ser Val Ser Ile Trp Val
465                 470                 475                 480

Ala Lys
```

<210> SEQ ID NO 86
<211> LENGTH: 1449
<212> TYPE: DNA

<213> ORGANISM: Artificial Sequence
<220> FEATURE:
<223> OTHER INFORMATION: Synthetically generated

<400> SEQUENCE: 86

```
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780 gttgggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acacaaccgg gagaagcgct ggaatcattt    1020
gttcaaggat ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaataa                                                            1449
```

<210> SEQ ID NO 87
<211> LENGTH: 482
<212> TYPE: PRT
<213> ORGANISM: Artificial Sequence
<220> FEATURE:
<223> OTHER INFORMATION: Synthetically generated

<400> SEQUENCE: 87

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
```

-continued

```
65                70                75                80

Thr Lys Thr Gln Leu Glu Arg Ala Ile Arg Ser Leu Lys Ala Asn Gly
                85                90                95

Ile Gln Val Tyr Ala Asp Val Val Phe Asn His Lys Ala Gly Ala Asp
                100                105                110

Gly Thr Glu Phe Val Asp Ala Val Glu Val Asp Pro Ser Asn Arg Asn
                115                120                125

Gln Glu Thr Ser Gly Thr Tyr Gln Ile Gln Ala Trp Thr Lys Phe Asp
    130                135                140

Phe Pro Gly Arg Gly Asn Thr Tyr Ser Ser Phe Lys Trp Arg Trp Tyr
145                150                155                160

His Phe Asp Gly Thr Asp Trp Asp Glu Ser Arg Lys Leu Asn Arg Ile
                165                170                175

Tyr Lys Phe Arg Gly Lys Ala Trp Asp Trp Glu Val Asp Thr Glu Asn
                180                185                190

Gly Asn Tyr Asp Tyr Leu Met Phe Ala Asp Leu Asp Met Asp His Pro
                195                200                205

Glu Val Val Thr Glu Leu Lys Asn Trp Gly Thr Trp Tyr Val Asn Thr
    210                215                220

Thr Asn Ile Asp Gly Phe Arg Leu Asp Ala Val Lys His Ile Lys Phe
225                230                235                240

Ser Phe Met Arg Asp Trp Leu Thr Tyr Val Arg Asn Gln Thr Gly Lys
                245                250                255

Asn Leu Phe Ala Val Gly Glu Phe Trp Ser Tyr Asp Val Asn Lys Leu
                260                265                270

His Asn Tyr Ile Thr Lys Thr Asn Gly Ser Met Ser Leu Phe Asp Ala
                275                280                285

Pro Leu His Asn Asn Phe Tyr Thr Ala Ser Lys Ser Ser Gly Tyr Phe
    290                295                300

Asp Met Arg Tyr Leu Leu Asn Asn Thr Leu Met Lys Asp Gln Pro Ser
305                310                315                320

Leu Ala Val Thr Leu Val Asp Asn His Asp Thr Gln Pro Gly Gln Ser
                325                330                335

Leu Gln Ser Trp Val Glu Pro Trp Phe Lys Pro Leu Ala Tyr Ala Phe
                340                345                350

Ile Leu Thr Arg Gln Glu Gly Tyr Pro Cys Val Phe Tyr Gly Asp Tyr
                355                360                365

Tyr Gly Ile Pro Lys Tyr Asn Ile Pro Gly Leu Lys Ser Lys Ile Asp
    370                375                380

Pro Leu Leu Ile Ala Arg Arg Asp Tyr Ala Tyr Gly Thr Gln Arg Asp
385                390                395                400

Tyr Ile Asp His Gln Asp Ile Ile Gly Trp Thr Arg Glu Gly Ile Asp
                405                410                415

Thr Lys Pro Asn Ser Gly Leu Ala Ala Leu Ile Thr Asp Gly Pro Gly
                420                425                430

Gly Ser Lys Trp Met Tyr Val Gly Lys Lys His Ala Gly Lys Val Phe
                435                440                445

Tyr Asp Leu Thr Gly Asn Arg Ser Asp Thr Val Thr Ile Asn Ala Asp
    450                455                460

Gly Trp Gly Glu Phe Lys Val Asn Gly Gly Ser Val Ser Ile Trp Val
465                470                475                480

Ala Lys
```

<210> SEQ ID NO 88
<211> LENGTH: 1449
<212> TYPE: DNA
<213> ORGANISM: Artificial Sequence
<220> FEATURE:
<223> OTHER INFORMATION: Synthetically generated

<400> SEQUENCE: 88
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa acatctggaa catatcaaat tcaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720 agtttatgc gggactggct aacatatgta cgtaatcaaa caggaaaaaa tttatttgcc     780
gttggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acgcaaccag ggcaatcttt acagtcatgg    1020
gtcgaacctt ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag ctccgtttc gatttgggtg    1440 gctaaataa                                                            1449

<210> SEQ ID NO 89
<211> LENGTH: 482
<212> TYPE: PRT
<213> ORGANISM: Artificial Sequence
<220> FEATURE:
<223> OTHER INFORMATION: Synthetically generated

<400> SEQUENCE: 89

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gln Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
                260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
            325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Ser Asp Gly Val Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val

```
465            470            475            480

Ala Lys

<210> SEQ ID NO 90
<211> LENGTH: 1449
<212> TYPE: DNA
<213> ORGANISM: Artificial Sequence
<220> FEATURE:
<223> OTHER INFORMATION: Synthetically generated

<400> SEQUENCE: 90
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaaatacgga    240 acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa gtgagcggaa cgtatcaaat tgaagcatgg     420
acaaaatttg attttcccgg tcggggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780 gttgggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acgcaaccag ggcaatcttt acagtcatgg    1020
gtcgaacctt ggtttaaacc acttgcttac gcctttattt taacgagaca agagggatat    1080
ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag ctccgtttc gatttgggtg     1440 gctaaataa                                                            1449

<210> SEQ ID NO 91
<211> LENGTH: 482
<212> TYPE: PRT
<213> ORGANISM: Artificial Sequence
<220> FEATURE:
<223> OTHER INFORMATION: Synthetically generated

<400> SEQUENCE: 91

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30
```

```
Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gln Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
        180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
                260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Glu Ala
                325                 330                 335

Leu Glu Ser Phe Val Gln Gly Trp Phe Lys Pro Leu Ala Tyr Ala Phe
                340                 345                 350

Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
        435                 440                 445
```

-continued

```
Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys

<210> SEQ ID NO 92
<211> LENGTH: 1449
<212> TYPE: DNA
<213> ORGANISM: Artificial Sequence
<220> FEATURE:
<223> OTHER INFORMATION: Synthetically generated

<400> SEQUENCE: 92
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcagga gcggaccaaa cagaatttgt cgatgcggtt     360
gaggtagacc cttctaatcg aaatcaagaa acatctggaa catatcaaat tcaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acacaaccgg gagaagcgct ggaatcattt    1020
gttcaaggat ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag ctccgtttc gatttgggtg    1440 gctaaataa                                                            1449

<210> SEQ ID NO 93
<211> LENGTH: 482
<212> TYPE: PRT
<213> ORGANISM: Artificial Sequence
<220> FEATURE:
<223> OTHER INFORMATION: Synthetically generated

<400> SEQUENCE: 93

Asn Thr Ala Pro Ile Asn Glu Thr Met Met Gln Tyr Phe Glu Trp Asp
```

```
1              5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
            85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
            165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
            245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
            325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Ser Asp Gly Val Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
            405                 410                 415

Thr Lys Pro Asn Ser Gly Leu Ala Ala Leu Ile Thr Asp Gly Pro Gly
            420                 425                 430
```

-continued

```
Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys

<210> SEQ ID NO 94
<211> LENGTH: 1449
<212> TYPE: DNA
<213> ORGANISM: Artificial Sequence
<220> FEATURE:
<223> OTHER INFORMATION: Synthetically generated

<400> SEQUENCE: 94
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780 gttgggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acgcaaccag ggcaatcttt acagtcatgg    1020
gtcgaacctt ggtttaaacc acttgcttac gcctttattt taacgagaca agagggatat    1080
ccttgcgtat tttacggtga ctattatgga atcccgagcg atggcgtccc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag ctccgtttc gatttgggtg    1440 gctaaataa                                                            1449

<210> SEQ ID NO 95
<211> LENGTH: 482
<212> TYPE: PRT
<213> ORGANISM: Artificial Sequence
<220> FEATURE:
<223> OTHER INFORMATION: Synthetically generated
```

```
<400> SEQUENCE: 95

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gln Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
            325                 330                 335

Leu Gln Ser Trp Val Glu Pro Trp Phe Lys Pro Leu Ala Tyr Ala Phe
        340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
```

-continued

```
               405              410              415
Thr Lys Pro Asn Ser Gly Leu Ala Ala Leu Ile Thr Asp Gly Pro Gly
            420              425              430
Gly Ser Lys Trp Met Tyr Val Gly Lys Lys His Ala Gly Lys Val Phe
        435              440              445
Tyr Asp Leu Thr Gly Asn Arg Ser Asp Thr Val Thr Ile Asn Ala Asp
    450              455              460
Gly Trp Gly Glu Phe Lys Val Asn Gly Gly Ser Val Ser Ile Trp Val
465              470              475              480
Ala Lys
```

<210> SEQ ID NO 96
<211> LENGTH: 1449
<212> TYPE: DNA
<213> ORGANISM: Artificial Sequence
<220> FEATURE:
<223> OTHER INFORMATION: Synthetically generated

<400> SEQUENCE: 96

```
aatactgcac ctattaacga aacaatgatg caatattttg aatgggattt accgaacgat     60
ggaacccttt ggacaaaggt gaaaaatgaa gccgcaaatc tttcttcgct cggtattaca    120
gcgttatggc ttcctccagc gtataaagga acaagtcaaa gcgatgtcgg atacggcgtg    180
tacgatttat atgaccttgg ggaatttaat caaaaaggac cgattcgaac aaaatacgga    240
acaaaaacac aatatattca agccatccaa gctgccaaag ccgcagggat gcaagtatat    300
gcagatgttg tctttaatca taaggcagga gcggaccaaa cagaatttgt cgatgcggtt    360
gaggtagacc cttctaatcg aaatcaagaa gtgagcggaa cgtatcaaat gaagcatgg     420 acaaaatttg attttcccgg tcgggggaac acatactcga gttttaaatg gcgttggtat    480
cattttgacg gtaccgattg ggatgaaagc cgaaaattaa atcggattta caaattccgc    540
ggaaaagcat gggactggga agtcgataca gaaaacggaa actatgatta tttaatgttc    600
gctgatttag atatggatca ccctgaggtt gtgacagaat taaaaaactg gggaacgtgg    660
tacgtcaata ctacaaatat cgatggattc cgcttagatg ccgtaaaaca tattaaattt    720
agttttatgc gggactggct aacatatgta cgtaatcaaa caggaaaaaa tttatttgcc    780 gttgggggaat tttggagcta tgacgtcaat aagctgcata attacattac aaaaacaaat    840
ggatcgatgt cattatttga tgcacctttg cataacaact tttataccgc ttccaaatcg    900
agtggatatt ttgacatgcg ttatttattg aataatacat taatgaaaga tcaaccttca    960
ctcgctgtga cacttgtcga taaccacgac acgcaaccag ggcaatcttt acagtcatgg   1020
gtcgaacctt ggtttaaacc acttgcttac gcctttattt taacgagaca agagggatat   1080
ccttgcgtat tttacggtga ctattatgga atcccgaaat acaatattcc aggattaaaa   1140
agcaaaatcg acccgctttt aattgctcgt cgggactatg cctatggaac acaacgtgat   1200
tacattgacc atcaagacat tattggatgg acacgcgaag gcattgatac aaaaccaaac   1260
tctggactgg cggctttaat taccgacggc cctggcggaa gcaaatggat gtatgtcggt   1320
aaaaaacatg ctggaaaagt attttatgat ttaaccggaa accgaagtga cacagtaacg   1380
attaatgcgg atggttgggg agaatttaaa gtaaacggag gctccgtttc gatttgggtg   1440
gctaaataa                                                          1449
```

<210> SEQ ID NO 97
<211> LENGTH: 482

-continued

```
<212> TYPE: PRT
<213> ORGANISM: Artificial Sequence
<220> FEATURE:
<223> OTHER INFORMATION: Synthetically generated

<400> SEQUENCE: 97

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
                260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
    370                 375                 380
```

```
Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys
```

```
<210> SEQ ID NO 98
<211> LENGTH: 1449
<212> TYPE: DNA
<213> ORGANISM: Artificial Sequence
<220> FEATURE:
<223> OTHER INFORMATION: Synthetically generated
```

```
<400> SEQUENCE: 98
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780 gttgggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acgcaaccag ggcaatcttt acagtcatgg    1020
gtcgaacctt ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag cattgatac aaaaccaaac     1260 tctggactgg cggctttaat taccgacggc cctggcggaa gcaaatggat gtatgtcggt    1320
aaaaaacatg ctggaaaagt atttttatgat ttaaccggaa accgaagtga cacagtaacg    1380
attaatgcgg atggttgggg agaatttaaa gtaaacggag gctccgtttc gatttgggtg    1440
gctaaataa                                                           1449
```

```
<210> SEQ ID NO 99
<211> LENGTH: 482
<212> TYPE: PRT
<213> ORGANISM: Artificial Sequence
<220> FEATURE:
<223> OTHER INFORMATION: Synthetically generated

<400> SEQUENCE: 99

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Tyr
225                 230                 235                 240

Ser Phe Phe Pro Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365
```

```
Tyr Gly Ile Pro Lys Tyr Asn Ile Pro Gly Leu Lys Ser Lys Ile Asp
    370              375              380

Pro Leu Leu Ile Ala Arg Arg Asp Tyr Ala Tyr Gly Thr Gln Arg Asp
385              390              395              400

Tyr Ile Asp His Gln Asp Ile Ile Gly Trp Thr Arg Glu Gly Ile Asp
             405              410              415

Thr Lys Pro Asn Ser Gly Leu Ala Ala Leu Ile Thr Asp Gly Pro Gly
         420              425              430

Gly Ser Lys Trp Met Tyr Val Gly Lys Lys His Ala Gly Lys Val Phe
         435              440              445

Tyr Asp Leu Thr Gly Asn Arg Ser Asp Thr Val Thr Ile Asn Ala Asp
    450              455              460

Gly Trp Gly Glu Phe Lys Val Asn Gly Gly Ser Val Ser Ile Trp Val
465              470              475              480

Ala Lys
```

<210> SEQ ID NO 100
<211> LENGTH: 1449
<212> TYPE: DNA
<213> ORGANISM: Artificial Sequence
<220> FEATURE:
<223> OTHER INFORMATION: Synthetically generated

<400> SEQUENCE: 100

```
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcggga gctgacggca cagaatttgt cgatgcggtt     360
gaggtagacc cttctaatcg aaatcaagaa gtgagcggaa cgtatcaaat gaagcatgg      420 acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaatac     720 agcttttcc ctgactggct aacatatgta cgtaatcaaa caggaaaaaa tttatttgcc      780
gttggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acgcaaccag gcaatctttt acagtcatgg    1020
gtcgaacctt ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt atttttatgat ttaaccggaa accgaagtga cacagtaacg    1380
```

```
attaatgcgg atggttgggg agaatttaaa gtaaacggag gctccgtttc gatttgggtg      1440
gctaaataa                                                               1449
```

<210> SEQ ID NO 101
<211> LENGTH: 482
<212> TYPE: PRT
<213> ORGANISM: Artificial Sequence
<220> FEATURE:
<223> OTHER INFORMATION: Synthetically generated

<400> SEQUENCE: 101

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Thr Ser Gly Thr Tyr Gln Ile Gln Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Tyr
225                 230                 235                 240

Ser Phe Phe Pro Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
```

```
                340             345             350
Ile Leu Thr Arg Gln Glu Gly Tyr Pro Cys Val Phe Tyr Gly Asp Tyr
        355             360             365
Tyr Gly Ile Pro Lys Tyr Asn Ile Pro Gly Leu Lys Ser Lys Ile Asp
        370             375             380
Pro Leu Leu Ile Ala Arg Arg Asp Tyr Ala Tyr Gly Thr Gln Arg Asp
385             390             395             400
Tyr Ile Asp His Gln Asp Ile Ile Gly Trp Thr Arg Glu Gly Ile Asp
            405             410             415
Thr Lys Pro Asn Ser Gly Leu Ala Ala Leu Ile Thr Asp Gly Pro Gly
            420             425             430
Gly Ser Lys Trp Met Tyr Val Gly Lys Lys His Ala Gly Lys Val Phe
            435             440             445
Tyr Asp Leu Thr Gly Asn Arg Ser Asp Thr Val Thr Ile Asn Ala Asp
        450             455             460
Gly Trp Gly Glu Phe Lys Val Asn Gly Gly Ser Val Ser Ile Trp Val
465             470             475             480
Ala Lys
```

<210> SEQ ID NO 102
<211> LENGTH: 1449
<212> TYPE: DNA
<213> ORGANISM: Artificial Sequence
<220> FEATURE:
<223> OTHER INFORMATION: Synthetically generated

<400> SEQUENCE: 102

```
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcggga gctgacggca cagaatttgt cgatgcggtt     360
gaggtagacc cttctaatcg aaatcaagaa acatctggaa catatcaaat tcaagcatgg     420
acaaaatttg attttcccgg tcggggaac acatactcga gttttaaatg gcgttggtat      480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaatac     720
agctttttcc ctgactggct aacatatgta cgtaatcaaa caggaaaaaa tttatttgcc     780
gttggggaat tttggagcta tgacgtcaat aagctgcata attacattac aaaaacaaat     840
ggatcgatgt cattatttga tgcacctttg cataacaact tttataccgc ttccaaatcg     900
agtggatatt ttgacatgcg ttatttattg aataatacat aatgaaaga tcaaccttca      960 ctcgctgtga cacttgtcga taaccacgac acgcaaccag gcaatcttt acagtcatgg     1020 gtcgaacctt ggtttaaacc acttgcttac gcctttattt taacgagaca gagagggatat     1080 ccttgcgtat tttacggtga ctattatgga atcccgaaat acaatattcc aggattaaaa     1140
agcaaaatcg acccgctttt aattgctcgt cgggactatg cctatggaac acaacgtgat     1200
tacattgacc atcaagacat tattggatgg acacgcgaag gcattgatac aaaaccaaac     1260
```

-continued

```
tctggactgg cggctttaat taccgacggc cctggcggaa gcaaatggat gtatgtcggt      1320
aaaaaacatg ctggaaaagt attttatgat ttaaccggaa accgaagtga cacagtaacg      1380
attaatgcgg atggttgggg agaatttaaa gtaaacggag ctccgtttc gatttgggtg       1440 gctaaataa                                                              1449
```

<210> SEQ ID NO 103
<211> LENGTH: 76
<212> TYPE: PRT
<213> ORGANISM: Artificial Sequence
<220> FEATURE:
<223> OTHER INFORMATION: Synthetically generated

<400> SEQUENCE: 103

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg
65                  70                  75
```

<210> SEQ ID NO 104
<211> LENGTH: 76
<212> TYPE: PRT
<213> ORGANISM: Artificial Sequence
<220> FEATURE:
<223> OTHER INFORMATION: Synthetically generated

<400> SEQUENCE: 104

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg
65                  70                  75
```

<210> SEQ ID NO 105
<211> LENGTH: 132
<212> TYPE: PRT
<213> ORGANISM: Artificial Sequence
<220> FEATURE:
<223> OTHER INFORMATION: Synthetically generated

<400> SEQUENCE: 105

```
Thr Lys Tyr Gly Thr Lys Thr Gln Tyr Ile Gln Ala Ile Gln Ala Ala
1               5                   10                  15

Lys Ala Ala Gly Met Gln Val Tyr Ala Asp Val Val Phe Asn His Lys
            20                  25                  30

Ala Gly Ala Asp Gly Thr Glu Phe Val Asp Ala Val Glu Val Asp Pro
        35                  40                  45

Ser Asn Arg Asn Gln Glu Thr Ser Gly Thr Tyr Gln Ile Gln Ala Trp
```

-continued

```
            50                  55                  60

Thr Lys Phe Asp Phe Pro Gly Arg Gly Asn Thr Tyr Ser Ser Phe Lys
65                  70                  75                  80

Trp Arg Trp Tyr His Phe Asp Gly Thr Asp Trp Asp Glu Ser Arg Lys
                85                  90                  95

Leu Asn Arg Ile Tyr Lys Phe Arg Gly Lys Ala Trp Asp Trp Glu Val
                100                 105                 110

Asp Thr Glu Asn Gly Asn Tyr Asp Tyr Leu Met Phe Ala Asp Leu Asp
            115                 120                 125

Met Asp His Pro
    130

<210> SEQ ID NO 106
<211> LENGTH: 132
<212> TYPE: PRT
<213> ORGANISM: Artificial Sequence
<220> FEATURE:
<223> OTHER INFORMATION: Synthetically generated

<400> SEQUENCE: 106

Thr Lys Tyr Gly Thr Lys Thr Gln Tyr Ile Gln Ala Ile Gln Ala Ala
1               5                   10                  15

Lys Ala Ala Gly Met Gln Val Tyr Ala Asp Val Val Phe Asn His Lys
                20                  25                  30

Ala Gly Ala Asp Gly Thr Glu Phe Val Asp Ala Val Glu Val Asp Pro
            35                  40                  45

Ser Asn Arg Asn Gln Glu Val Ser Gly Thr Tyr Gln Ile Glu Ala Trp
    50                  55                  60

Thr Lys Phe Asp Phe Pro Gly Arg Gly Asn Thr Tyr Ser Ser Phe Lys
65                  70                  75                  80

Trp Arg Trp Tyr His Phe Asp Gly Thr Asp Trp Asp Glu Ser Arg Lys
                85                  90                  95

Leu Asn Arg Ile Tyr Lys Phe Arg Gly Lys Ala Trp Asp Trp Glu Val
                100                 105                 110

Asp Thr Glu Asn Gly Asn Tyr Asp Tyr Leu Met Phe Ala Asp Leu Asp
            115                 120                 125

Met Asp His Pro
    130

<210> SEQ ID NO 107
<211> LENGTH: 132
<212> TYPE: PRT
<213> ORGANISM: Artificial Sequence
<220> FEATURE:
<223> OTHER INFORMATION: Synthetically generated

<400> SEQUENCE: 107

Thr Lys Tyr Gly Thr Lys Thr Gln Tyr Ile Gln Ala Ile Gln Ala Ala
1               5                   10                  15

Lys Ala Ala Gly Met Gln Val Tyr Ala Asp Val Val Phe Asn His Lys
                20                  25                  30

Ala Gly Ala Asp Gln Thr Glu Phe Val Asp Ala Val Glu Val Asp Pro
            35                  40                  45

Ser Asn Arg Asn Gln Glu Thr Ser Gly Thr Tyr Gln Ile Gln Ala Trp
    50                  55                  60

Thr Lys Phe Asp Phe Pro Gly Arg Gly Asn Thr Tyr Ser Ser Phe Lys
65                  70                  75                  80
```

```
Trp Arg Trp Tyr His Phe Asp Gly Thr Asp Trp Asp Glu Ser Arg Lys
                85                  90                  95

Leu Asn Arg Ile Tyr Lys Phe Arg Gly Lys Ala Trp Asp Trp Glu Val
            100                 105                 110

Asp Thr Glu Asn Gly Asn Tyr Asp Tyr Leu Met Phe Ala Asp Leu Asp
        115                 120                 125

Met Asp His Pro
    130
```

```
<210> SEQ ID NO 108
<211> LENGTH: 132
<212> TYPE: PRT
<213> ORGANISM: Artificial Sequence
<220> FEATURE:
<223> OTHER INFORMATION: Synthetically generated

<400> SEQUENCE: 108

Thr Lys Tyr Gly Thr Lys Thr Gln Tyr Ile Gln Ala Ile Gln Ala Ala
1               5                   10                  15

Lys Ala Ala Gly Met Gln Val Tyr Ala Asp Val Val Phe Asn His Lys
            20                  25                  30

Ala Gly Ala Asp Gln Thr Glu Phe Val Asp Ala Val Glu Val Asp Pro
        35                  40                  45

Ser Asn Arg Asn Gln Glu Val Ser Gly Thr Tyr Gln Ile Glu Ala Trp
    50                  55                  60

Thr Lys Phe Asp Phe Pro Gly Arg Gly Asn Thr Tyr Ser Ser Phe Lys
65                  70                  75                  80

Trp Arg Trp Tyr His Phe Asp Gly Thr Asp Trp Asp Glu Ser Arg Lys
                85                  90                  95

Leu Asn Arg Ile Tyr Lys Phe Arg Gly Lys Ala Trp Asp Trp Glu Val
            100                 105                 110

Asp Thr Glu Asn Gly Asn Tyr Asp Tyr Leu Met Phe Ala Asp Leu Asp
        115                 120                 125

Met Asp His Pro
    130
```

```
<210> SEQ ID NO 109
<211> LENGTH: 132
<212> TYPE: PRT
<213> ORGANISM: Artificial Sequence
<220> FEATURE:
<223> OTHER INFORMATION: Synthetically generated

<400> SEQUENCE: 109

Thr Lys Tyr Gly Thr Lys Thr Gln Leu Glu Arg Ala Ile Arg Ser Leu
1               5                   10                  15

Lys Ala Asn Gly Ile Gln Val Tyr Ala Asp Val Val Phe Asn His Lys
            20                  25                  30

Ala Gly Ala Asp Gly Thr Glu Phe Val Asp Ala Val Glu Val Asp Pro
        35                  40                  45

Ser Asn Arg Asn Gln Glu Thr Ser Gly Thr Tyr Gln Ile Gln Ala Trp
    50                  55                  60

Thr Lys Phe Asp Phe Pro Gly Arg Gly Asn Thr Tyr Ser Ser Phe Lys
65                  70                  75                  80

Trp Arg Trp Tyr His Phe Asp Gly Thr Asp Trp Asp Glu Ser Arg Lys
                85                  90                  95

Leu Asn Arg Ile Tyr Lys Phe Arg Gly Lys Ala Trp Asp Trp Glu Val
            100                 105                 110
```

```
Asp Thr Glu Asn Gly Asn Tyr Asp Tyr Leu Met Phe Ala Asp Leu Asp
        115                 120                 125

Met Asp His Pro
    130

<210> SEQ ID NO 110
<211> LENGTH: 132
<212> TYPE: PRT
<213> ORGANISM: Artificial Sequence
<220> FEATURE:
<223> OTHER INFORMATION: Synthetically generated

<400> SEQUENCE: 110

Thr Lys Tyr Gly Thr Lys Thr Gln Leu Glu Arg Ala Ile Arg Ser Leu
1               5                   10                  15

Lys Ala Asn Gly Ile Gln Val Tyr Ala Asp Val Val Phe Asn His Lys
            20                  25                  30

Ala Gly Ala Asp Gly Thr Glu Phe Val Asp Ala Val Glu Val Asp Pro
        35                  40                  45

Ser Asn Arg Asn Gln Glu Val Ser Gly Thr Tyr Gln Ile Glu Ala Trp
    50                  55                  60

Thr Lys Phe Asp Phe Pro Gly Arg Gly Asn Thr Tyr Ser Ser Phe Lys
65                  70                  75                  80

Trp Arg Trp Tyr His Phe Asp Gly Thr Asp Trp Asp Glu Ser Arg Lys
                85                  90                  95

Leu Asn Arg Ile Tyr Lys Phe Arg Gly Lys Ala Trp Asp Trp Glu Val
            100                 105                 110

Asp Thr Glu Asn Gly Asn Tyr Asp Tyr Leu Met Phe Ala Asp Leu Asp
        115                 120                 125

Met Asp His Pro
    130

<210> SEQ ID NO 111
<211> LENGTH: 132
<212> TYPE: PRT
<213> ORGANISM: Artificial Sequence
<220> FEATURE:
<223> OTHER INFORMATION: Synthetically generated

<400> SEQUENCE: 111

Thr Lys Tyr Gly Thr Lys Thr Gln Leu Glu Arg Ala Ile Arg Ser Leu
1               5                   10                  15

Lys Ala Asn Gly Ile Gln Val Tyr Ala Asp Val Val Phe Asn His Lys
            20                  25                  30

Ala Gly Ala Asp Gln Thr Glu Phe Val Asp Ala Val Glu Val Asp Pro
        35                  40                  45

Ser Asn Arg Asn Gln Glu Thr Ser Gly Thr Tyr Gln Ile Gln Ala Trp
    50                  55                  60

Thr Lys Phe Asp Phe Pro Gly Arg Gly Asn Thr Tyr Ser Ser Phe Lys
65                  70                  75                  80

Trp Arg Trp Tyr His Phe Asp Gly Thr Asp Trp Asp Glu Ser Arg Lys
                85                  90                  95

Leu Asn Arg Ile Tyr Lys Phe Arg Gly Lys Ala Trp Asp Trp Glu Val
            100                 105                 110

Asp Thr Glu Asn Gly Asn Tyr Asp Tyr Leu Met Phe Ala Asp Leu Asp
        115                 120                 125

Met Asp His Pro
```

```
        130

<210> SEQ ID NO 112
<211> LENGTH: 132
<212> TYPE: PRT
<213> ORGANISM: Artificial Sequence
<220> FEATURE:
<223> OTHER INFORMATION: Synthetically generated

<400> SEQUENCE: 112

Thr Lys Tyr Gly Thr Lys Thr Gln Leu Glu Arg Ala Ile Arg Ser Leu
1               5                   10                  15

Lys Ala Asn Gly Ile Gln Val Tyr Ala Asp Val Val Phe Asn His Lys
            20                  25                  30

Ala Gly Ala Asp Gln Thr Glu Phe Val Asp Ala Val Glu Val Asp Pro
        35                  40                  45

Ser Asn Arg Asn Gln Glu Val Ser Gly Thr Tyr Gln Ile Glu Ala Trp
    50                  55                  60

Thr Lys Phe Asp Phe Pro Gly Arg Gly Asn Thr Tyr Ser Ser Phe Lys
65                  70                  75                  80

Trp Arg Trp Tyr His Phe Asp Gly Thr Asp Trp Asp Glu Ser Arg Lys
                85                  90                  95

Leu Asn Arg Ile Tyr Lys Phe Arg Gly Lys Ala Trp Asp Trp Glu Val
            100                 105                 110

Asp Thr Glu Asn Gly Asn Tyr Asp Tyr Leu Met Phe Ala Asp Leu Asp
        115                 120                 125

Met Asp His Pro
    130

<210> SEQ ID NO 113
<211> LENGTH: 92
<212> TYPE: PRT
<213> ORGANISM: Artificial Sequence
<220> FEATURE:
<223> OTHER INFORMATION: Synthetically generated

<400> SEQUENCE: 113

Glu Val Val Thr Glu Leu Lys Asn Trp Gly Thr Trp Tyr Val Asn Thr
1               5                   10                  15

Thr Asn Ile Asp Gly Phe Arg Leu Asp Ala Val Lys His Ile Lys Tyr
            20                  25                  30

Ser Phe Phe Pro Asp Trp Leu Thr Tyr Val Arg Asn Gln Thr Gly Lys
        35                  40                  45

Asn Leu Phe Ala Val Gly Glu Phe Trp Ser Tyr Asp Val Asn Lys Leu
    50                  55                  60

His Asn Tyr Ile Thr Lys Thr Asn Gly Ser Met Ser Leu Phe Asp Ala
65                  70                  75                  80

Pro Leu His Asn Asn Phe Tyr Thr Ala Ser Lys Ser
                85                  90

<210> SEQ ID NO 114
<211> LENGTH: 92
<212> TYPE: PRT
<213> ORGANISM: Artificial Sequence
<220> FEATURE:
<223> OTHER INFORMATION: Synthetically generated

<400> SEQUENCE: 114

Glu Val Val Thr Glu Leu Lys Asn Trp Gly Thr Trp Tyr Val Asn Thr
1               5                   10                  15
```

-continued

```
Thr Asn Ile Asp Gly Phe Arg Leu Asp Ala Val Lys His Ile Lys Tyr
        20              25              30

Ser Phe Phe Pro Asp Trp Leu Thr Tyr Val Arg Asn Gln Thr Gly Lys
        35              40              45

Asn Leu Phe Ala Val Gly Glu Phe Trp Lys Asn Asp Leu Gly Ala Leu
        50              55              60

Glu Asn Tyr Ile Thr Lys Thr Asn Gly Ser Met Ser Leu Phe Asp Ala
65              70              75              80

Pro Leu His Asn Asn Phe Tyr Thr Ala Ser Lys Ser
                85              90
```

<210> SEQ ID NO 115
<211> LENGTH: 92
<212> TYPE: PRT
<213> ORGANISM: Artificial Sequence
<220> FEATURE:
<223> OTHER INFORMATION: Synthetically generated

<400> SEQUENCE: 115

```
Glu Val Val Thr Glu Leu Lys Asn Trp Gly Thr Trp Tyr Val Asn Thr
1               5               10              15

Thr Asn Ile Asp Gly Phe Arg Leu Asp Ala Val Lys His Ile Lys Tyr
        20              25              30

Ser Phe Phe Pro Asp Trp Leu Gly His Val Arg Gly Gln Thr Gly Lys
        35              40              45

Asn Leu Phe Ala Val Gly Glu Phe Trp Ser Tyr Asp Val Asn Lys Leu
        50              55              60

His Asn Tyr Ile Thr Lys Thr Asn Gly Ser Met Ser Leu Phe Asp Ala
65              70              75              80

Pro Leu His Asn Asn Phe Tyr Thr Ala Ser Lys Ser
                85              90
```

<210> SEQ ID NO 116
<211> LENGTH: 92
<212> TYPE: PRT
<213> ORGANISM: Artificial Sequence
<220> FEATURE:
<223> OTHER INFORMATION: Synthetically generated

<400> SEQUENCE: 116

```
Glu Val Val Thr Glu Leu Lys Asn Trp Gly Thr Trp Tyr Val Asn Thr
1               5               10              15

Thr Asn Ile Asp Gly Phe Arg Leu Asp Ala Val Lys His Ile Lys Tyr
        20              25              30

Ser Phe Phe Pro Asp Trp Leu Gly His Val Arg Gly Gln Thr Gly Lys
        35              40              45

Asn Leu Phe Ala Val Gly Glu Phe Trp Lys Asn Asp Leu Gly Ala Leu
        50              55              60

Glu Asn Tyr Ile Thr Lys Thr Asn Gly Ser Met Ser Leu Phe Asp Ala
65              70              75              80

Pro Leu His Asn Asn Phe Tyr Thr Ala Ser Lys Ser
                85              90
```

<210> SEQ ID NO 117
<211> LENGTH: 92
<212> TYPE: PRT
<213> ORGANISM: Artificial Sequence
<220> FEATURE:
<223> OTHER INFORMATION: Synthetically generated

<400> SEQUENCE: 117

Glu Val Val Thr Glu Leu Lys Asn Trp Gly Thr Trp Tyr Val Asn Thr
1               5                   10                  15

Thr Asn Ile Asp Gly Phe Arg Leu Asp Ala Val Lys His Ile Lys Phe
            20                  25                  30

Ser Phe Met Arg Asp Trp Leu Thr Tyr Val Arg Asn Gln Thr Gly Lys
        35                  40                  45

Asn Leu Phe Ala Val Gly Glu Phe Trp Ser Tyr Asp Val Asn Lys Leu
    50                  55                  60

His Asn Tyr Ile Thr Lys Thr Asn Gly Ser Met Ser Leu Phe Asp Ala
65                  70                  75                  80

Pro Leu His Asn Asn Phe Tyr Thr Ala Ser Lys Ser
            85                  90

<210> SEQ ID NO 118
<211> LENGTH: 92
<212> TYPE: PRT
<213> ORGANISM: Artificial Sequence
<220> FEATURE:
<223> OTHER INFORMATION: Synthetically generated

<400> SEQUENCE: 118

Glu Val Val Thr Glu Leu Lys Asn Trp Gly Thr Trp Tyr Val Asn Thr
1               5                   10                  15

Thr Asn Ile Asp Gly Phe Arg Leu Asp Ala Val Lys His Ile Lys Phe
            20                  25                  30

Ser Phe Met Arg Asp Trp Leu Thr Tyr Val Arg Asn Gln Thr Gly Lys
        35                  40                  45

Asn Leu Phe Ala Val Gly Glu Phe Trp Lys Asn Asp Leu Gly Ala Leu
    50                  55                  60

Glu Asn Tyr Ile Thr Lys Thr Asn Gly Ser Met Ser Leu Phe Asp Ala
65                  70                  75                  80

Pro Leu His Asn Asn Phe Tyr Thr Ala Ser Lys Ser
            85                  90

<210> SEQ ID NO 119
<211> LENGTH: 92
<212> TYPE: PRT
<213> ORGANISM: Artificial Sequence
<220> FEATURE:
<223> OTHER INFORMATION: Synthetically generated

<400> SEQUENCE: 119

Glu Val Val Thr Glu Leu Lys Asn Trp Gly Thr Trp Tyr Val Asn Thr
1               5                   10                  15

Thr Asn Ile Asp Gly Phe Arg Leu Asp Ala Val Lys His Ile Lys Phe
            20                  25                  30

Ser Phe Met Arg Asp Trp Leu Gly His Val Arg Gly Gln Thr Gly Lys
        35                  40                  45

Asn Leu Phe Ala Val Gly Glu Phe Trp Ser Tyr Asp Val Asn Lys Leu
    50                  55                  60

His Asn Tyr Ile Thr Lys Thr Asn Gly Ser Met Ser Leu Phe Asp Ala
65                  70                  75                  80

Pro Leu His Asn Asn Phe Tyr Thr Ala Ser Lys Ser
            85                  90

<210> SEQ ID NO 120

<211> LENGTH: 92
<212> TYPE: PRT
<213> ORGANISM: Artificial Sequence
<220> FEATURE:
<223> OTHER INFORMATION: Synthetically generated

<400> SEQUENCE: 120

```
Glu Val Val Thr Glu Leu Lys Asn Trp Gly Thr Trp Tyr Val Asn Thr
1               5                   10                  15

Thr Asn Ile Asp Gly Phe Arg Leu Asp Ala Val Lys His Ile Lys Phe
            20                  25                  30

Ser Phe Met Arg Asp Trp Leu Gly His Val Arg Gly Gln Thr Gly Lys
        35                  40                  45

Asn Leu Phe Ala Val Gly Glu Phe Trp Lys Asn Asp Leu Gly Ala Leu
    50                  55                  60

Glu Asn Tyr Ile Thr Lys Thr Asn Gly Ser Met Ser Leu Phe Asp Ala
65                  70                  75                  80

Pro Leu His Asn Asn Phe Tyr Thr Ala Ser Lys Ser
                85                  90
```

<210> SEQ ID NO 121
<211> LENGTH: 182
<212> TYPE: PRT
<213> ORGANISM: Artificial Sequence
<220> FEATURE:
<223> OTHER INFORMATION: Synthetically generated

<400> SEQUENCE: 121

```
Ser Gly Tyr Phe Asp Met Arg Tyr Leu Leu Asn Asn Thr Leu Met Lys
1               5                   10                  15

Asp Gln Pro Ser Leu Ala Val Thr Leu Val Asp Asn His Asp Thr Gln
            20                  25                  30

Pro Gly Gln Ser Leu Gln Ser Trp Val Glu Pro Trp Phe Lys Pro Leu
        35                  40                  45

Ala Tyr Ala Phe Ile Leu Thr Arg Gln Glu Gly Tyr Pro Cys Val Phe
    50                  55                  60

Tyr Gly Asp Tyr Tyr Gly Ile Pro Lys Tyr Asn Ile Pro Gly Leu Lys
65                  70                  75                  80

Ser Lys Ile Asp Pro Leu Leu Ile Ala Arg Arg Asp Tyr Ala Tyr Gly
                85                  90                  95

Thr Gln Arg Asp Tyr Ile Asp His Gln Asp Ile Ile Gly Trp Thr Arg
            100                 105                 110

Glu Gly Ile Asp Thr Lys Pro Asn Ser Gly Leu Ala Ala Leu Ile Thr
        115                 120                 125

Asp Gly Pro Gly Gly Ser Lys Trp Met Tyr Val Gly Lys Lys His Ala
    130                 135                 140

Gly Lys Val Phe Tyr Asp Leu Thr Gly Asn Arg Ser Asp Thr Val Thr
145                 150                 155                 160

Ile Asn Ala Asp Gly Trp Gly Glu Phe Lys Val Asn Gly Gly Ser Val
                165                 170                 175

Ser Ile Trp Val Ala Lys
            180
```

<210> SEQ ID NO 122
<211> LENGTH: 182
<212> TYPE: PRT
<213> ORGANISM: Artificial Sequence
<220> FEATURE:
<223> OTHER INFORMATION: Synthetically generated

<400> SEQUENCE: 122

```
Ser Gly Tyr Phe Asp Met Arg Tyr Leu Leu Asn Asn Thr Leu Met Lys
1               5                   10                  15

Asp Gln Pro Ser Leu Ala Val Thr Leu Val Asp Asn His Asp Thr Gln
            20                  25                  30

Pro Gly Gln Ser Leu Gln Ser Trp Val Glu Pro Trp Phe Lys Pro Leu
        35                  40                  45

Ala Tyr Ala Phe Ile Leu Thr Arg Gln Glu Gly Tyr Pro Cys Val Phe
        50                  55                  60

Tyr Gly Asp Tyr Tyr Gly Ile Pro Ser Asp Gly Val Pro Gly Leu Lys
65                  70                  75                  80

Ser Lys Ile Asp Pro Leu Leu Ile Ala Arg Arg Asp Tyr Ala Tyr Gly
                85                  90                  95

Thr Gln Arg Asp Tyr Ile Asp His Gln Asp Ile Ile Gly Trp Thr Arg
            100                 105                 110

Glu Gly Ile Asp Thr Lys Pro Asn Ser Gly Leu Ala Ala Leu Ile Thr
            115                 120                 125

Asp Gly Pro Gly Gly Ser Lys Trp Met Tyr Val Gly Lys Lys His Ala
        130                 135                 140

Gly Lys Val Phe Tyr Asp Leu Thr Gly Asn Arg Ser Asp Thr Val Thr
145                 150                 155                 160

Ile Asn Ala Asp Gly Trp Gly Glu Phe Lys Val Asn Gly Gly Ser Val
                165                 170                 175

Ser Ile Trp Val Ala Lys
            180
```

<210> SEQ ID NO 123
<211> LENGTH: 182
<212> TYPE: PRT
<213> ORGANISM: Artificial Sequence
<220> FEATURE:
<223> OTHER INFORMATION: Synthetically generated

<400> SEQUENCE: 123

```
Ser Gly Tyr Phe Asp Met Arg Tyr Leu Leu Asn Asn Thr Leu Met Lys
1               5                   10                  15

Asp Gln Pro Ser Leu Ala Val Thr Leu Val Asp Asn His Asp Thr Gln
            20                  25                  30

Pro Gly Glu Ala Leu Glu Ser Phe Val Gln Gly Trp Phe Lys Pro Leu
        35                  40                  45

Ala Tyr Ala Phe Ile Leu Thr Arg Gln Glu Gly Tyr Pro Cys Val Phe
        50                  55                  60

Tyr Gly Asp Tyr Tyr Gly Ile Pro Lys Tyr Asn Ile Pro Gly Leu Lys
65                  70                  75                  80

Ser Lys Ile Asp Pro Leu Leu Ile Ala Arg Arg Asp Tyr Ala Tyr Gly
                85                  90                  95

Thr Gln Arg Asp Tyr Ile Asp His Gln Asp Ile Ile Gly Trp Thr Arg
            100                 105                 110

Glu Gly Ile Asp Thr Lys Pro Asn Ser Gly Leu Ala Ala Leu Ile Thr
            115                 120                 125

Asp Gly Pro Gly Gly Ser Lys Trp Met Tyr Val Gly Lys Lys His Ala
        130                 135                 140

Gly Lys Val Phe Tyr Asp Leu Thr Gly Asn Arg Ser Asp Thr Val Thr
145                 150                 155                 160
```

```
Ile Asn Ala Asp Gly Trp Gly Glu Phe Lys Val Asn Gly Gly Ser Val
            165                 170                 175

Ser Ile Trp Val Ala Lys
            180

<210> SEQ ID NO 124
<211> LENGTH: 182
<212> TYPE: PRT
<213> ORGANISM: Artificial Sequence
<220> FEATURE:
<223> OTHER INFORMATION: Synthetically generated

<400> SEQUENCE: 124

Ser Gly Tyr Phe Asp Met Arg Tyr Leu Leu Asn Asn Thr Leu Met Lys
1               5                   10                  15

Asp Gln Pro Ser Leu Ala Val Thr Leu Val Asp Asn His Asp Thr Gln
            20                  25                  30

Pro Gly Glu Ala Leu Glu Ser Phe Val Gln Gly Trp Phe Lys Pro Leu
        35                  40                  45

Ala Tyr Ala Phe Ile Leu Thr Arg Gln Glu Gly Tyr Pro Cys Val Phe
    50                  55                  60

Tyr Gly Asp Tyr Tyr Gly Ile Pro Ser Asp Gly Val Pro Gly Leu Lys
65                  70                  75                  80

Ser Lys Ile Asp Pro Leu Leu Ile Ala Arg Arg Asp Tyr Ala Tyr Gly
            85                  90                  95

Thr Gln Arg Asp Tyr Ile Asp His Gln Asp Ile Ile Gly Trp Thr Arg
            100                 105                 110

Glu Gly Ile Asp Thr Lys Pro Asn Ser Gly Leu Ala Ala Leu Ile Thr
        115                 120                 125

Asp Gly Pro Gly Gly Ser Lys Trp Met Tyr Val Gly Lys Lys His Ala
    130                 135                 140

Gly Lys Val Phe Tyr Asp Leu Thr Gly Asn Arg Ser Asp Thr Val Thr
145                 150                 155                 160

Ile Asn Ala Asp Gly Trp Gly Glu Phe Lys Val Asn Gly Gly Ser Val
            165                 170                 175

Ser Ile Trp Val Ala Lys
            180

<210> SEQ ID NO 125
<211> LENGTH: 182
<212> TYPE: PRT
<213> ORGANISM: Artificial Sequence
<220> FEATURE:
<223> OTHER INFORMATION: Synthetically generated

<400> SEQUENCE: 125

Ser Gly Tyr Phe Asp Met Arg Asn Leu Leu Asn Gly Thr Leu Val Gln
1               5                   10                  15

Arg His Pro Ser His Ala Val Thr Leu Val Asp Asn His Asp Thr Gln
            20                  25                  30

Pro Gly Gln Ser Leu Gln Ser Trp Val Glu Pro Trp Phe Lys Pro Leu
        35                  40                  45

Ala Tyr Ala Phe Ile Leu Thr Arg Gln Glu Gly Tyr Pro Cys Val Phe
    50                  55                  60

Tyr Gly Asp Tyr Tyr Gly Ile Pro Lys Tyr Asn Ile Pro Gly Leu Lys
65                  70                  75                  80

Ser Lys Ile Asp Pro Leu Leu Ile Ala Arg Arg Asp Tyr Ala Tyr Gly
            85                  90                  95
```

-continued

```
Thr Gln Arg Asp Tyr Ile Asp His Gln Asp Ile Ile Gly Trp Thr Arg
        100             105             110

Glu Gly Ile Asp Thr Lys Pro Asn Ser Gly Leu Ala Ala Leu Ile Thr
        115             120             125

Asp Gly Pro Gly Gly Ser Lys Trp Met Tyr Val Gly Lys Lys His Ala
    130             135             140

Gly Lys Val Phe Tyr Asp Leu Thr Gly Asn Arg Ser Asp Thr Val Thr
145             150             155             160

Ile Asn Ala Asp Gly Trp Gly Glu Phe Lys Val Asn Gly Gly Ser Val
            165             170             175

Ser Ile Trp Val Ala Lys
        180

<210> SEQ ID NO 126
<211> LENGTH: 182
<212> TYPE: PRT
<213> ORGANISM: Artificial Sequence
<220> FEATURE:
<223> OTHER INFORMATION: Synthetically generated

<400> SEQUENCE: 126

Ser Gly Tyr Phe Asp Met Arg Asn Leu Leu Asn Gly Thr Leu Val Gln
1               5               10              15

Arg His Pro Ser His Ala Val Thr Leu Val Asp Asn His Asp Thr Gln
            20              25              30

Pro Gly Gln Ser Leu Gln Ser Trp Val Glu Pro Trp Phe Lys Pro Leu
        35              40              45

Ala Tyr Ala Phe Ile Leu Thr Arg Gln Glu Gly Tyr Pro Cys Val Phe
    50              55              60

Tyr Gly Asp Tyr Tyr Gly Ile Pro Ser Asp Gly Val Pro Gly Leu Lys
65              70              75              80

Ser Lys Ile Asp Pro Leu Leu Ile Ala Arg Arg Asp Tyr Ala Tyr Gly
            85              90              95

Thr Gln Arg Asp Tyr Ile Asp His Gln Asp Ile Ile Gly Trp Thr Arg
        100             105             110

Glu Gly Ile Asp Thr Lys Pro Asn Ser Gly Leu Ala Ala Leu Ile Thr
        115             120             125

Asp Gly Pro Gly Gly Ser Lys Trp Met Tyr Val Gly Lys Lys His Ala
    130             135             140

Gly Lys Val Phe Tyr Asp Leu Thr Gly Asn Arg Ser Asp Thr Val Thr
145             150             155             160

Ile Asn Ala Asp Gly Trp Gly Glu Phe Lys Val Asn Gly Gly Ser Val
            165             170             175

Ser Ile Trp Val Ala Lys
        180

<210> SEQ ID NO 127
<211> LENGTH: 182
<212> TYPE: PRT
<213> ORGANISM: Artificial Sequence
<220> FEATURE:
<223> OTHER INFORMATION: Synthetically generated

<400> SEQUENCE: 127

Ser Gly Tyr Phe Asp Met Arg Asn Leu Leu Asn Gly Thr Leu Val Gln
1               5               10              15

Arg His Pro Ser His Ala Val Thr Leu Val Asp Asn His Asp Thr Gln
```

-continued

```
             20              25              30

Pro Gly Glu Ala Leu Glu Ser Phe Val Gln Gly Trp Phe Lys Pro Leu
        35              40              45

Ala Tyr Ala Phe Ile Leu Thr Arg Gln Glu Gly Tyr Pro Cys Val Phe
    50              55              60

Tyr Gly Asp Tyr Tyr Gly Ile Pro Lys Tyr Asn Ile Pro Gly Leu Lys
65              70              75              80

Ser Lys Ile Asp Pro Leu Leu Ile Ala Arg Arg Asp Tyr Ala Tyr Gly
            85              90              95

Thr Gln Arg Asp Tyr Ile Asp His Gln Asp Ile Ile Gly Trp Thr Arg
            100             105             110

Glu Gly Ile Asp Thr Lys Pro Asn Ser Gly Leu Ala Ala Leu Ile Thr
        115             120             125

Asp Gly Pro Gly Gly Ser Lys Trp Met Tyr Val Gly Lys Lys His Ala
        130             135             140

Gly Lys Val Phe Tyr Asp Leu Thr Gly Asn Arg Ser Asp Thr Val Thr
145             150             155             160

Ile Asn Ala Asp Gly Trp Gly Glu Phe Lys Val Asn Gly Gly Ser Val
            165             170             175

Ser Ile Trp Val Ala Lys
            180

<210> SEQ ID NO 128
<211> LENGTH: 182
<212> TYPE: PRT
<213> ORGANISM: Artificial Sequence
<220> FEATURE:
<223> OTHER INFORMATION: Synthetically generated

<400> SEQUENCE: 128

Ser Gly Tyr Phe Asp Met Arg Asn Leu Leu Asn Gly Thr Leu Val Gln
1               5               10              15

Arg His Pro Ser His Ala Val Thr Leu Val Asp Asn His Asp Thr Gln
            20              25              30

Pro Gly Glu Ala Leu Glu Ser Phe Val Gln Gly Trp Phe Lys Pro Leu
        35              40              45

Ala Tyr Ala Phe Ile Leu Thr Arg Gln Glu Gly Tyr Pro Cys Val Phe
    50              55              60

Tyr Gly Asp Tyr Tyr Gly Ile Pro Ser Asp Gly Val Pro Gly Leu Lys
65              70              75              80

Ser Lys Ile Asp Pro Leu Leu Ile Ala Arg Arg Asp Tyr Ala Tyr Gly
            85              90              95

Thr Gln Arg Asp Tyr Ile Asp His Gln Asp Ile Ile Gly Trp Thr Arg
            100             105             110

Glu Gly Ile Asp Thr Lys Pro Asn Ser Gly Leu Ala Ala Leu Ile Thr
        115             120             125

Asp Gly Pro Gly Gly Ser Lys Trp Met Tyr Val Gly Lys Lys His Ala
        130             135             140

Gly Lys Val Phe Tyr Asp Leu Thr Gly Asn Arg Ser Asp Thr Val Thr
145             150             155             160

Ile Asn Ala Asp Gly Trp Gly Glu Phe Lys Val Asn Gly Gly Ser Val
            165             170             175

Ser Ile Trp Val Ala Lys
            180
```

```
<210> SEQ ID NO 129
<211> LENGTH: 182
<212> TYPE: PRT
<213> ORGANISM: Artificial Sequence
<220> FEATURE:
<223> OTHER INFORMATION: Synthetically generated

<400> SEQUENCE: 129

Ser Gly Tyr Phe Asp Met Arg Asn Leu Leu Asn Gly Thr Leu Val Gln
1               5                   10                  15

Arg His Pro Ser Leu Ala Val Thr Leu Val Asp Asn His Asp Thr Gln
            20                  25                  30

Pro Gly Gln Ser Leu Gln Ser Trp Val Glu Pro Trp Phe Lys Pro Leu
        35                  40                  45

Ala Tyr Ala Phe Ile Leu Thr Arg Gln Glu Gly Tyr Pro Cys Val Phe
    50                  55                  60

Tyr Gly Asp Tyr Tyr Gly Ile Pro Lys Tyr Asn Ile Pro Gly Leu Lys
65                  70                  75                  80

Ser Lys Ile Asp Pro Leu Leu Ile Ala Arg Arg Asp Tyr Ala Tyr Gly
                85                  90                  95

Thr Gln Arg Asp Tyr Ile Asp His Gln Asp Ile Ile Gly Trp Thr Arg
            100                 105                 110

Glu Gly Ile Asp Thr Lys Pro Asn Ser Gly Leu Ala Ala Leu Ile Thr
        115                 120                 125

Asp Gly Pro Gly Gly Ser Lys Trp Met Tyr Val Gly Lys Lys His Ala
    130                 135                 140

Gly Lys Val Phe Tyr Asp Leu Thr Gly Asn Arg Ser Asp Thr Val Thr
145                 150                 155                 160

Ile Asn Ala Asp Gly Trp Gly Glu Phe Lys Val Asn Gly Gly Ser Val
                165                 170                 175

Ser Ile Trp Val Ala Lys
            180

<210> SEQ ID NO 130
<211> LENGTH: 182
<212> TYPE: PRT
<213> ORGANISM: Artificial Sequence
<220> FEATURE:
<223> OTHER INFORMATION: Synthetically generated

<400> SEQUENCE: 130

Ser Gly Tyr Phe Asp Met Arg Tyr Leu Leu Asn Gly Thr Leu Val Gln
1               5                   10                  15

Arg His Pro Ser His Ala Val Thr Leu Val Asp Asn His Asp Thr Gln
            20                  25                  30

Pro Gly Gln Ser Leu Gln Ser Trp Val Glu Pro Trp Phe Lys Pro Leu
        35                  40                  45

Ala Tyr Ala Phe Ile Leu Thr Arg Gln Glu Gly Tyr Pro Cys Val Phe
    50                  55                  60

Tyr Gly Asp Tyr Tyr Gly Ile Pro Lys Tyr Asn Ile Pro Gly Leu Lys
65                  70                  75                  80

Ser Lys Ile Asp Pro Leu Leu Ile Ala Arg Arg Asp Tyr Ala Tyr Gly
                85                  90                  95

Thr Gln Arg Asp Tyr Ile Asp His Gln Asp Ile Ile Gly Trp Thr Arg
            100                 105                 110

Glu Gly Ile Asp Thr Lys Pro Asn Ser Gly Leu Ala Ala Leu Ile Thr
        115                 120                 125
```

```
Asp Gly Pro Gly Gly Ser Lys Trp Met Tyr Val Gly Lys Lys His Ala
    130                 135                 140

Gly Lys Val Phe Tyr Asp Leu Thr Gly Asn Arg Ser Asp Thr Val Thr
145                 150                 155                 160

Ile Asn Ala Asp Gly Trp Gly Glu Phe Lys Val Asn Gly Gly Ser Val
                165                 170                 175

Ser Ile Trp Val Ala Lys
            180

<210> SEQ ID NO 131
<211> LENGTH: 482
<212> TYPE: PRT
<213> ORGANISM: Artificial Sequence
<220> FEATURE:
<223> OTHER INFORMATION: Synthetically generated

<400> SEQUENCE: 131

His Asp Gly Thr Asn Gly Thr Ile Met Gln Tyr Phe Glu Trp Asn Val
1               5                   10                  15

Pro Asn Asp Gly Gln His Trp Asn Arg Leu His Asn Asn Ala Gln Asn
                20                  25                  30

Leu Lys Asn Ala Gly Ile Thr Ala Ile Trp Ile Pro Pro Ala Trp Lys
            35                  40                  45

Gly Thr Ser Gln Ser Asp Thr Gly Tyr Gly Ala Tyr Asp Leu Tyr Asp
        50                  55                  60

Leu Gly Glu Phe Asn Gln Arg Gly Thr Val Arg Thr Lys Tyr Gly Thr
65                  70                  75                  80

Lys Ala Glu Leu Glu Arg Ala Ile Arg Ser Leu Lys Ala Asn Gly Ile
                85                  90                  95

Gln Val Tyr Gly Asp Val Val Met Asn His Lys Ala Gly Ala Asp Gln
                100                 105                 110

Thr Glu Gln Val Gln Ala Val Glu Val Asn Pro Gln Asn Arg Asn Gln
            115                 120                 125

Glu Val Ser Gly Thr Tyr Gln Ile Glu Ala Trp Thr Gly Phe Asn Phe
        130                 135                 140

Pro Gly Arg Gly Asn Gln His Ser Ser Phe Lys Trp Arg Trp Tyr His
145                 150                 155                 160

Phe Asp Gly Thr Asp Phe Asp Gln Ser Arg Gly Leu Ser Asn Arg Ile
                165                 170                 175

Tyr Lys Phe Arg Thr Lys Ala Trp Asp Trp Glu Val Asp Thr Glu Phe
                180                 185                 190

Gly Asn Tyr Asp Tyr Leu Met Tyr Ala Asp Leu Asp Met Asp His Pro
            195                 200                 205

Glu Val Ile Asn Glu Leu Asn Arg Trp Gly Val Trp Tyr Ala Asn Thr
        210                 215                 220

Leu Asn Leu Asp Gly Phe Arg Leu Asp Ala Val Lys His Ile Lys Phe
225                 230                 235                 240

Ser Phe Met Arg Asp Trp Leu Gly His Val Arg Gly Gln Thr Gly Lys
                245                 250                 255

Asn Leu Phe Ala Val Ala Glu Tyr Trp Lys Asn Asp Leu Gly Ala Leu
            260                 265                 270

Glu Asn Tyr Leu Ser Lys Thr Asn Trp Thr Met Ser Ala Phe Asp Val
        275                 280                 285

Pro Leu His Tyr Asn Leu Tyr Gln Ala Ser Asn Ser Ser Gly Asn Tyr
    290                 295                 300
```

-continued

```
Asp Met Arg Asn Leu Leu Asn Gly Thr Leu Val Gln Arg His Pro Ser
305                 310                 315                 320

His Ala Val Thr Phe Val Asp Asn His Asp Thr Gln Pro Gly Glu Ala
                325                 330                 335

Leu Glu Ser Phe Val Gln Gly Trp Phe Lys Pro Leu Ala Tyr Ala Thr
                340                 345                 350

Ile Leu Thr Arg Glu Gln Gly Tyr Pro Gln Val Phe Tyr Gly Asp Tyr
                355                 360                 365

Tyr Gly Ile Pro Ser Asp Gly Val Pro Ser Tyr Arg Gln Gln Ile Asp
        370                 375                 380

Pro Leu Leu Ala Ala Arg Gln Gln Tyr Ala Tyr Gly Thr Gln His Asp
385                 390                 395                 400

Tyr Leu Asp Asn Gln Asp Val Ile Gly Trp Thr Arg Glu Gly Asp Ser
                405                 410                 415

Ala His Ala Gly Ser Gly Leu Ala Thr Val Met Ser Asp Gly Pro Gly
                420                 425                 430

Gly Ser Lys Thr Met Tyr Val Gly Thr Ala His Ala Gly Gln Val Phe
                435                 440                 445

Lys Asp Ile Thr Gly Asn Arg Thr Asp Thr Val Thr Ile Asn Ser Ala
        450                 455                 460

Gly Asn Gly Thr Phe Arg Cys Asn Lys Gly Ser Val Ser Ile Trp Val
465                 470                 475                 480

Lys Gln
```

```
<210> SEQ ID NO 132
<211> LENGTH: 583
<212> TYPE: PRT
<213> ORGANISM: Artificial Sequence
<220> FEATURE:
<223> OTHER INFORMATION: Bacillus sp.

<400> SEQUENCE: 132

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
                35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gly Thr Glu Phe Val Asp Ala Val Glu Val Asp Pro Ser Asn Arg Asn
                115                 120                 125

Gln Glu Thr Ser Gly Thr Tyr Gln Ile Gln Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
```

-continued

```
                180                 185                 190

Glu Asn Gly Asn Tyr Asp Tyr Leu Met Phe Ala Asp Leu Asp Met Asp
            195                 200                 205

His Pro Glu Val Val Thr Glu Leu Lys Asn Trp Gly Thr Trp Tyr Val
            210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
            275                 280                 285

Asp Ala Pro Leu His Asn Asn Phe Tyr Thr Ala Ser Lys Ser Ser Gly
            290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
                340                 345                 350

Ala Phe Ile Leu Thr Arg Gln Glu Gly Tyr Pro Cys Val Phe Tyr Gly
                355                 360                 365

Asp Tyr Tyr Gly Ile Pro Lys Tyr Asn Ile Pro Gly Leu Lys Ser Lys
            370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
                420                 425                 430

Pro Gly Gly Ser Lys Trp Met Tyr Val Gly Lys Lys His Ala Gly Lys
            435                 440                 445

Val Phe Tyr Asp Leu Thr Gly Asn Arg Ser Asp Thr Val Thr Ile Asn
            450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
                485                 490                 495

Thr Thr Ser Gly Gln Asn Val Tyr Val Val Ala Asn Ile Pro Glu Leu
                500                 505                 510

Gly Asn Trp Asn Thr Ala Asn Ala Ile Lys Met Asn Pro Ser Ser Tyr
                515                 520                 525

Pro Thr Trp Lys Ala Thr Ile Ala Leu Pro Gln Gly Lys Ala Ile Glu
            530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
                565                 570                 575

Thr Ala Ser Trp Asn Val Pro
                580
```

<210> SEQ ID NO 133

```
<211> LENGTH: 484
<212> TYPE: PRT
<213> ORGANISM: Artificial Sequence
<220> FEATURE:
<223> OTHER INFORMATION: Synthetically generated

<400> SEQUENCE: 133

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
            165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
            195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
            245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
    275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
            325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Gly Leu Lys Ser Lys
    370                 375                 380
```

```
Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
                420                 425                 430

Pro Gly Gly Ser Lys Trp Met Tyr Val Gly Lys Lys His Ala Gly Lys
                435                 440                 445

Val Phe Tyr Asp Leu Thr Gly Asn Arg Ser Asp Thr Val Thr Ile Asn
            450                 455                 460

Ala Asp Gly Trp Gly Glu Phe Lys Val Asn Gly Gly Ser Val Ser Ile
465                 470                 475                 480

Trp Val Ala Lys

<210> SEQ ID NO 134
<211> LENGTH: 482
<212> TYPE: PRT
<213> ORGANISM: Artificial Sequence
<220> FEATURE:
<223> OTHER INFORMATION: Synthetically generated

<400> SEQUENCE: 134

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
                20                  25                  30

Asn Leu Lys Asn Ala Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255
```

-continued

```
Asn Leu Phe Ala Val Gly Glu Phe Trp Lys Asn Asp Leu Gly Ala Leu
            260                 265                 270

Glu Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Thr Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Asn Gly Thr Phe Lys Val Asn Gly Gly Ser Val Ser Ile Trp Val
465                 470                 475                 480

Ala Lys

<210> SEQ ID NO 135
<211> LENGTH: 1446
<212> TYPE: DNA
<213> ORGANISM: Artificial Sequence
<220> FEATURE:
<223> OTHER INFORMATION: Synthetically generated

<400> SEQUENCE: 135
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcggggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
```

-continued

```
gttggggaat tttggaaaaa tgatttgggc gcgctcgaga attacattac aaaaacaaat      840
ggatcgatgt cattatttga tgcacctttg cataacaact tttataccgc ttccaaatcg      900
agtggatatt ttgacatgcg taatttgctg aacggaacgc ttgtccaacg acacccttct      960
cacgctgtga cacttgtcga taaccacgac acgcaaccag ggcaatcttt acagtcatgg     1020
gtcgaacctt ggtttaaacc acttgcttac gcctttattt taacgagaca agagggatat     1080
ccttgcgtat tttacggtga ctattatgga atcccgaaat acaatattcc aggattaaaa     1140
agcaaaatcg acccgctttt aattgctcgt cgggactatg cctatggaac acaacgtgat     1200
tacattgacc atcaagacat tattggatgg acacgcgaag gcattgatac aaaaccaaac     1260
tctggactgg cggctttaat taccgacggc cctggcggaa gcaaaacgat gtatgtcggt     1320
aaaaaacatg ctggaaaagt attttatgat ttaaccggaa accgaagtga cacagtaacg     1380
attaatgcgg atggtaacgg aacgtttaaa gtaaacggag gctccgtttc gatttgggtg     1440
gctaaa                                                                 1446
```

```
<210> SEQ ID NO 136
<211> LENGTH: 482
<212> TYPE: PRT
<213> ORGANISM: Artificial Sequence
<220> FEATURE:
<223> OTHER INFORMATION: Synthetically generated

<400> SEQUENCE: 136

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240
```

```
Ser Phe Met Arg Asp Trp Leu Thr Tyr Val Arg Asn Gln Thr Gly Lys
            245                 250                 255

Asn Leu Phe Ala Val Gly Glu Phe Trp Lys Asn Asp Leu Gly Ala Leu
            260                 265                 270

Glu Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
        290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
            325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
            405                 410                 415

Thr Lys Pro Asn Ser Gly Leu Ala Ala Leu Ile Thr Asp Gly Pro Gly
            420                 425                 430

Gly Ser Lys Tyr Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
        450                 455                 460

Gly Asn Gly Glu Phe Lys Val Asn Gly Gly Ser Val Ser Ile Trp Val
465                 470                 475                 480

Ala Lys
```

<210> SEQ ID NO 137
<211> LENGTH: 1446
<212> TYPE: DNA
<213> ORGANISM: Artificial Sequence
<220> FEATURE:
<223> OTHER INFORMATION: Synthetically generated

<400> SEQUENCE: 137

```
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
```

```
tacgtcaata ctacaaatat cgatggattc cgcttagatg ccgtaaaaca tattaaattt    720
agttttatgc gggactggct aacatatgta cgtaatcaaa caggaaaaaa tttatttgcc    780
gttggggaat tttggaaaaa tgatttgggc gcgctcgaga attacattac aaaaacaaat    840
ggatcgatgt cattatttga tgcacctttg cataacaact tttataccgc ttccaaatcg    900
agtggatatt ttgacatgcg taatttgctg aacggaacgc ttgtccaacg acacccttct    960
cacgctgtga cacttgtcga taaccacgac acgcaaccag ggcaatcttt acagtcatgg   1020
gtcgaacctt ggtttaaacc acttgcttac gcctttattt taacgagaca agagggatat   1080
ccttgcgtat tttacggtga ctattatgga atcccgaaat acaatattcc aggattaaaa   1140
agcaaaatcg acccgctttt aattgctcgt cgggactatg cctatggaac acaacgtgat   1200
tacattgacc atcaagacat tattggatgg acacgcgaag gcattgatac aaaaccaaac   1260
tctggactgg cggctttaat taccgacggc cctggcggaa gcaaatatat gtatgtcggt   1320
aaaaaacatg ctggaaaagt attttatgat ttaaccggaa accgaagtga cacagtaacg   1380
attaatgcgg atggtaacgg agaatttaaa gtaaacggag gctccgtttc gatttgggtg   1440
gctaaa                                                             1446
```

<210> SEQ ID NO 138
<211> LENGTH: 482
<212> TYPE: PRT
<213> ORGANISM: Artificial Sequence
<220> FEATURE:
<223> OTHER INFORMATION: Synthetically generated

<400> SEQUENCE: 138

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
```

-continued

```
            210              215              220

Thr Asn Ile Asp Gly Phe Arg Leu Asp Ala Val Lys His Ile Lys Phe
225              230              235              240

Ser Phe Met Arg Asp Trp Leu Thr Tyr Val Arg Asn Gln Thr Gly Lys
                 245              250              255

Asn Leu Phe Ala Val Gly Glu Phe Trp Lys Asn Asp Leu Gly Ala Leu
             260              265              270

Glu Asn Tyr Ile Thr Lys Thr Asn Gly Ser Met Ser Leu Phe Asp Ala
             275              280              285

Pro Leu His Asn Asn Phe Tyr Thr Ala Ser Lys Ser Ser Gly Tyr Phe
             290              295              300

Asp Met Arg Asn Leu Leu Asn Gly Thr Leu Val Gln Arg His Pro Ser
305              310              315              320

His Ala Val Thr Leu Val Asp Asn His Asp Thr Gln Pro Gly Gln Ser
                 325              330              335

Leu Gln Ser Trp Val Glu Pro Trp Phe Lys Pro Leu Ala Tyr Ala Phe
                 340              345              350

Ile Leu Thr Arg Gln Glu Gly Tyr Pro Cys Val Phe Tyr Gly Asp Tyr
             355              360              365

Tyr Gly Ile Pro Lys Tyr Asn Ile Pro Gly Leu Lys Ser Lys Ile Asp
             370              375              380

Pro Leu Leu Ile Ala Arg Arg Asp Tyr Ala Tyr Gly Thr Gln Arg Asp
385              390              395              400

Tyr Ile Asp His Gln Asp Ile Ile Gly Trp Thr Arg Glu Gly Ile Asp
                 405              410              415

Thr Lys Pro Asn Ser Gly Leu Ala Ala Leu Ile Thr Asp Gly Pro Gly
                 420              425              430

Gly Ser Lys Arg Met Tyr Val Gly Lys Lys His Ala Gly Lys Val Phe
                 435              440              445

Tyr Asp Leu Thr Gly Asn Arg Ser Asp Thr Val Thr Ile Asn Ala Asp
             450              455              460

Gly Asn Gly Thr Phe Lys Val Asn Gly Gly Ser Val Ser Ile Trp Val
465              470              475              480

Ala Lys
```

<210> SEQ ID NO 139
<211> LENGTH: 1446
<212> TYPE: DNA
<213> ORGANISM: Artificial Sequence
<220> FEATURE:
<223> OTHER INFORMATION: Synthetically generated

<400> SEQUENCE: 139

```
aatactgcac ctattaacga aacaatgatg caatattttg aatgggattt accgaacgat       60
ggaacccttt ggaatagact ccataataat gcgcaaaacc ttaagaatgc aggtattaca      120
gcgttatggc ttcctccagc gtataaagga acaagtcaaa gcgatgtcgg atacggcgtg      180
tacgatttat atgaccttgg ggaatttaat caaaaaggaa cgattcgaac aaaatacgga      240
acaaaaacac aactggaacg cgcaattaga tccttaaaag ctaacggaat ccaagtatat      300
gcagatgttg tctttaatca taaggcggga gctgacggca cagaatttgt cgatgcggtt      360
gaggtagacc cttctaatcg aaatcaagaa gtgagcggaa cgtatcaaat tgaagcatgg      420
acaaaatttg attttcccgg tcggggaac acatactcga gttttaaatg gcgttggtat      480
cattttgacg gtaccgattg ggatgaaagc cgaaaattaa atcggattta caaattccgc      540
```

-continued

```
ggaaaagcat gggactggga agtcgataca gaaaacggaa actatgatta tttaatgttc    600
gctgatttag atatggatca ccctgaggtt gtgacagaat taaaaaactg gggaacgtgg    660
tacgtcaata ctacaaatat cgatggattc cgcttagatg ccgtaaaaca tattaaattt    720
agttttatgc gggactggct aacatatgta cgtaatcaaa caggaaaaaa tttatttgcc    780
gttggggaat tttggaaaaa tgatttgggc gcgctcgaga attacattac aaaaacaaat    840
ggatcgatgt cattatttga tgcacctttg cataacaact tttataccgc ttccaaatcg    900
agtggatatt ttgacatgcg taatttgctg aacggaacgc ttgtccaacg acacccttct    960
cacgctgtga cacttgtcga taaccacgac acgcaaccag ggcaatcttt acagtcatgg   1020
gtcgaacctt ggtttaaacc acttgcttac gcctttattt taacgagaca agagggatat   1080
ccttgcgtat tttacggtga ctattatgga atcccgaaat acaatattcc aggattaaaa   1140
agcaaaatcg acccgctttt aattgctcgt cgggactatg cctatggaac acaacgtgat   1200
tacattgacc atcaagacat tattggatgg acacgcgaag gcattgatac aaaaccaaac   1260
tctggactgg cggctttaat taccgacggc cctggcggaa gcaaacgcat gtatgtcggt   1320
aaaaaacatg ctggaaaagt attttatgat ttaaccggaa accgaagtga cacagtaacg   1380
attaatgcgg atggtaacgg aacgtttaaa gtaaacggag gctccgtttc gatttgggtg   1440
gctaaa                                                             1446
```

<210> SEQ ID NO 140
<211> LENGTH: 482
<212> TYPE: PRT
<213> ORGANISM: Artificial Sequence
<220> FEATURE:
<223> OTHER INFORMATION: Synthetically generated

<400> SEQUENCE: 140

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190
```

-continued

```
Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Lys Asn Asp Leu Gly Ala Leu
                260                 265                 270

Glu Asn Tyr Ile Thr Lys Thr Asn Gly Ser Met Ser Leu Phe Asp Ala
                275                 280                 285

Pro Leu His Asn Asn Phe Tyr Thr Ala Ser Lys Ser Ser Gly Tyr Phe
        290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Glu Trp Phe Lys Pro Leu Ala Tyr Ala Phe
                340                 345                 350

Ile Leu Thr Arg Gln Glu Gly Tyr Pro Cys Val Phe Tyr Gly Asp Tyr
                355                 360                 365

Tyr Gly Ile Pro Lys Tyr Asn Ile Pro Gly Met Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
                435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys
```

```
<210> SEQ ID NO 141
<211> LENGTH: 1446
<212> TYPE: DNA
<213> ORGANISM: Artificial Sequence
<220> FEATURE:
<223> OTHER INFORMATION: Synthetically generated

<400> SEQUENCE: 141
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
```

-continued

```
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780 gttgggggaat tttggaaaaa tgatttgggc gcgctcgaga attacattac aaaaacaaat     840
ggatcgatgt cattatttga tgcacctttg cataacaact tttataccgc ttccaaatcg     900
agtggatatt ttgacatgcg taatttgctg aacggaacgc ttgtccaacg acaccttct      960 cacgctgtga cacttgtcga taaccacgac acgcaaccag ggcaatcttt acagtcatgg    1020
gtcgaagaat ggtttaaacc acttgcttac gcctttattt taacgagaca agagggatat    1080
ccttgcgtat tttacggtga ctattatgga atcccgaaat acaatattcc aggaatgaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggcttttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaa                                                              1446
```

<210> SEQ ID NO 142
<211> LENGTH: 482
<212> TYPE: PRT
<213> ORGANISM: Artificial Sequence
<220> FEATURE:
<223> OTHER INFORMATION: Synthetically generated

<400> SEQUENCE: 142

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175
```

```
Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
            210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Lys Asn Asp Leu Gly Ala Leu
            260                 265                 270

Glu Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
            290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
                340                 345                 350

Ile Leu Thr Arg Gln Glu Gly Tyr Pro Cys Val Phe Tyr Gly Asp Tyr
                355                 360                 365

Tyr Gly Ile Pro Lys His Gly Ile Pro Gly Leu Lys Ser Lys Ile Asp
            370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
                435                 440                 445

Tyr Asp Leu Thr Gly Asn Arg Ser Asp Thr Val Thr Ile Asn Ala Asp
            450                 455                 460

Gly Trp Gly Glu Phe Lys Val Asn Gly Gly Ser Val Ser Ile Trp Val
465                 470                 475                 480

Ala Lys
```

<210> SEQ ID NO 143
<211> LENGTH: 1446
<212> TYPE: DNA
<213> ORGANISM: Artificial Sequence
<220> FEATURE:
<223> OTHER INFORMATION: Synthetically generated

<400> SEQUENCE: 143

```
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
```

```
gcagatgttg tctttaatca taaggcggga gctgacggca cagaatttgt cgatgcggtt      360
gaggtagacc cttctaatcg aaatcaagaa gtgagcggaa cgtatcaaat tgaagcatgg      420
acaaaatttg attttcccgg tcgggggaac acatactcga gttttaaatg gcgttggtat      480
cattttgacg gtaccgattg ggatgaaagc cgaaaattaa atcggattta caaattccgc      540
ggaaaagcat gggactggga agtcgataca gaaaacggaa actatgatta tttaatgttc      600
gctgatttag atatggatca ccctgaggtt gtgacagaat aaaaaaactg gggaacgtgg      660
tacgtcaata ctacaaatat cgatggattc cgcttagatg ccgtaaaaca tattaaattt      720
agttttatgc gggactggct aacatatgta cgtaatcaaa caggaaaaaa tttatttgcc      780
gttggggaat tttggaaaaa tgatttgggc gcgctcgaga attacattac aaaaacaaat      840
ggatcgatgt cattatttga tgcacctttg cataacaact tttataccgc ttccaaatcg      900
agtggatatt ttgacatgcg taatttgctg aacggaacgc ttgtccaacg acacccttct      960
cacgctgtga cacttgtcga taaccacgac acgcaaccag ggcaatcttt acagtcatgg     1020
gtcgaacctt ggtttaaacc acttgcttac gcctttattt taacgagaca agagggatat     1080
ccttgcgtat tttacggtga ctattatgga atcccgaaac atggcattcc aggattaaaa     1140
agcaaaatcg acccgctttt aattgctcgt cgggactatg cctatggaac acaacgtgat     1200
tacattgacc atcaagacat tattggatgg acacgcgaag gcattgatac aaaaccaaac     1260
tctggactgg cggctttaat taccgacggc cctggcggaa gcaaatggat gtatgtcggt     1320
aaaaaacatg ctggaaaagt attttatgat ttaaccggaa accgaagtga cacagtaacg     1380
attaatgcgg atggttgggg agaatttaaa gtaaacggag gctccgtttc gatttgggtg     1440
gctaaa                                                                 1446
```

```
<210> SEQ ID NO 144
<211> LENGTH: 482
<212> TYPE: PRT
<213> ORGANISM: Artificial Sequence
<220> FEATURE:
<223> OTHER INFORMATION: Synthetically generated

<400> SEQUENCE: 144

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
```

-continued

```
145              150              155              160

His Phe Asp Gly Thr Asp Trp Asp Glu Ser Arg Lys Leu Asn Arg Ile
             165              170              175

Tyr Lys Phe Arg Gly Lys Ala Trp Asp Trp Glu Val Asp Thr Glu Asn
             180              185              190

Gly Asn Tyr Asp Tyr Leu Met Phe Ala Asp Leu Asp Met Asp His Pro
             195              200              205

Glu Val Val Thr Glu Leu Lys Asn Trp Gly Thr Trp Tyr Val Asn Thr
    210              215              220

Thr Asn Ile Asp Gly Phe Arg Leu Asp Ala Val Lys His Ile Lys Phe
225              230              235              240

Ser Phe Met Arg Asp Trp Leu Thr Tyr Val Arg Asn Gln Thr Gly Lys
             245              250              255

Asn Leu Phe Ala Val Gly Glu Phe Trp Lys Asn Asp Leu Gly Ala Leu
             260              265              270

Glu Asn Tyr Ile Thr Lys Thr Asn Gly Ser Met Ser Leu Phe Asp Ala
             275              280              285

Pro Leu His Asn Asn Phe Tyr Thr Ala Ser Lys Ser Ser Gly Tyr Phe
    290              295              300

Asp Met Arg Asn Leu Leu Asn Gly Thr Leu Val Gln Arg His Pro Ser
305              310              315              320

His Ala Val Thr Leu Val Asp Asn His Asp Thr Gln Pro Gly Gln Ser
             325              330              335

Leu Gln Ser Trp Val Glu Pro Trp Phe Lys Pro Leu Ala Tyr Ala Phe
             340              345              350

Ile Leu Thr Arg Gln Glu Gly Tyr Pro Cys Val Phe Tyr Gly Asp Tyr
             355              360              365

Tyr Gly Ile Pro Lys Tyr Asn Ile Pro Gly Leu Lys Ser Lys Ile Asp
    370              375              380

Pro Leu Leu Glu Ala Arg Arg Asp Tyr Ala Tyr Gly Thr Gln Arg Asp
385              390              395              400

Tyr Ile Asp His Gln Asp Ile Ile Gly Trp Thr Arg Glu Gly Ile Asp
             405              410              415

Thr Lys Pro Asn Ser Gly Leu Ala Ala Leu Ile Thr Asp Gly Pro Gly
             420              425              430

Gly Ser Lys Trp Met Tyr Val Gly Lys Lys His Ala Gly Lys Val Phe
             435              440              445

Tyr Asp Ile Thr Gly Asn Arg Ser Asp Thr Val Thr Ile Asn Ala Asp
    450              455              460

Gly Trp Gly Glu Phe Lys Val Asn Gly Gly Ser Val Ser Ile Trp Val
465              470              475              480

Ala Lys
```

```
<210> SEQ ID NO 145
<211> LENGTH: 1446
<212> TYPE: DNA
<213> ORGANISM: Artificial Sequence
<220> FEATURE:
<223> OTHER INFORMATION: Synthetically generated

<400> SEQUENCE: 145
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
```

```
tacgatttat atgaccttgg ggaatttaat caaaaaggaa cgattcgaac aaaatacgga        240
acaaaaacac aactggaacg cgcaattaga tccttaaaag ctaacggaat ccaagtatat        300
gcagatgttg tctttaatca taaggcggga gctgacggca cagaatttgt cgatgcggtt        360
gaggtagacc cttctaatcg aaatcaagaa gtgagcggaa cgtatcaaat tgaagcatgg        420
acaaaatttg attttcccgg tcgggggaac acatactcga gttttaaatg gcgttggtat        480
cattttgacg gtaccgattg ggatgaaagc cgaaaattaa atcggattta caaattccgc        540
ggaaaagcat gggactggga agtcgataca gaaaacggaa actatgatta tttaatgttc        600
gctgatttag atatggatca ccctgaggtt gtgacagaat aaaaaaactg gggaacgtgg        660
tacgtcaata ctacaaatat cgatggattc cgcttagatg ccgtaaaaca tattaaattt        720
agttttatgc gggactggct aacatatgta cgtaatcaaa caggaaaaaa tttatttgcc        780
gttggggaat tttggaaaaa tgatttgggc gcgctcgaga attacattac aaaaacaaat        840
ggatcgatgt cattatttga tgcacctttg cataacaact tttataccgc ttccaaatcg        900
agtggatatt ttgacatgcg taatttgctg aacggaacgc ttgtccaacg acacccttct        960
cacgctgtga cacttgtcga taaccacgac acgcaaccag ggcaatcttt acagtcatgg       1020
gtcgaacctt ggtttaaacc acttgcttac gcctttattt taacgagaca agagggatat       1080
ccttgcgtat tttacggtga ctattatgga atcccgaaat acaatattcc aggattaaaa       1140
agcaaaatcg acccgctttt agaagctcgt cgggactatg cctatggaac acaacgtgat       1200
tacattgacc atcaagacat tattggatgg acacgcgaag gcattgatac aaaaccaaac       1260
tctggactgg cggctttaat taccgacggc cctggcggaa gcaaatggat gtatgtcggt       1320
aaaaaacatg ctggaaaagt attttatgat atcaccggaa accgaagtga cacagtaacg       1380
attaatgcgg atggttgggg agaatttaaa gtaaacggag gctccgtttc gatttgggtg       1440
gctaaa                                                                  1446
```

<210> SEQ ID NO 146
<211> LENGTH: 482
<212> TYPE: PRT
<213> ORGANISM: Artificial Sequence
<220> FEATURE:
<223> OTHER INFORMATION: Synthetically generated

<400> SEQUENCE: 146

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125
```

-continued

```
Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
                195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Lys Asn Asp Leu Gly Ala Leu
                260                 265                 270

Glu Asn Tyr Ile Thr Lys Thr Asn Gly Ser Met Ser Leu Phe Asp Ala
                275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
                340                 345                 350

Ile Leu Thr Arg Gln Glu Gly Tyr Pro Cys Val Phe Tyr Gly Asp Tyr
                355                 360                 365

Tyr Gly Ile Pro Lys Tyr Asn Ile Pro Gly Leu Lys Ser Lys Ile Asp
    370                 375                 380

Pro Leu Leu Glu Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
                435                 440                 445

Lys Asp Ile Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Gln
```

```
<210> SEQ ID NO 147
<211> LENGTH: 1446
<212> TYPE: DNA
<213> ORGANISM: Artificial Sequence
<220> FEATURE:
<223> OTHER INFORMATION: Synthetically generated

<400> SEQUENCE: 147
aatactgcac ctattaacga aacaatgatg caatattttg aatgggattt accgaacgat      60
```

-continued

```
ggaacccttt ggaatagact ccataataat gcgcaaaacc ttaagaatgc aggtattaca    120
gcgttatggc ttcctccagc gtataaagga acaagtcaaa gcgatgtcgg atacggcgtg    180
tacgatttat atgaccttgg ggaatttaat caaaaaggaa cgattcgaac aaaatacgga    240
acaaaaacac aactggaacg cgcaattaga tccttaaaag ctaacggaat ccaagtatat    300
gcagatgttg tctttaatca taaggcggga gctgacggca cagaatttgt cgatgcggtt    360
gaggtagacc cttctaatcg aaatcaagaa gtgagcggaa cgtatcaaat tgaagcatgg    420
acaaaatttg attttcccgg tcgggggaac acatactcga gttttaaatg gcgttggtat    480
cattttgacg gtaccgattg ggatgaaagc cgaaaattaa atcggattta caaattccgc    540
ggaaaagcat gggactggga agtcgataca gaaaacggaa actatgatta tttaatgttc    600
gctgatttag atatggatca ccctgaggtt gtgacagaat taaaaaactg gggaacgtgg    660
tacgtcaata ctacaaatat cgatggattc cgcttagatg ccgtaaaaca tattaaattt    720
agttttatgc gggactggct aacatatgta cgtaatcaaa caggaaaaaa tttatttgcc    780
gttggggaat tttggaaaaa tgatttgggc gcgctcgaga attacattac aaaaacaaat    840
ggatcgatgt cattatttga tgcacctttg cataacaact tttataccgc ttccaaatcg    900
agtggatatt ttgacatgcg taatttgctg aacggaacgc ttgtccaacg acacccttct    960
cacgctgtga cacttgtcga taaccacgac acgcaaccag gcaatctttt acagtcatgg    1020
gtcgaacctt ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt agaagctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt atttaaagat atcaccggaa accgaagtga cacagtaacg    1380
attaatgcgg atggttgggg agaatttaaa gtaaacggag gctccgtttc gatttgggtg    1440
gctcag                                                               1446
```

<210> SEQ ID NO 148
<211> LENGTH: 482
<212> TYPE: PRT
<213> ORGANISM: Artificial Sequence
<220> FEATURE:
<223> OTHER INFORMATION: Synthetically generated

<400> SEQUENCE: 148

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110
```

```
Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Lys Asn Asp Leu Gly Ala Leu
                260                 265                 270

Glu Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
                340                 345                 350

Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Asp Ser
                405                 410                 415

Ser His Pro Asn Ser Gly Leu Ala Ala Leu Ile Thr Asp Gly Pro Gly
                420                 425                 430

Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys
```

<210> SEQ ID NO 149
<211> LENGTH: 1446
<212> TYPE: DNA
<213> ORGANISM: Artificial Sequence
<220> FEATURE:
<223> OTHER INFORMATION: Synthetically generated -continued

<400> SEQUENCE: 149

```
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat aaaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggaaaaa tgatttgggc gcgctcgaga attacattac aaaaacaaat     840
ggatcgatgt cattatttga tgcacctttg cataacaact tttataccgc ttccaaatcg     900
agtggatatt ttgacatgcg taatttgctg aacggaacgc ttgtccaacg acacccttct     960
cacgctgtga cacttgtcga taaccacgac acgcaaccag ggcaatcttt acagtcatgg    1020
gtcgaacctt ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcgatagcag ccatccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaa                                                               1446
```

<210> SEQ ID NO 150
<211> LENGTH: 482
<212> TYPE: PRT
<213> ORGANISM: Artificial Sequence
<220> FEATURE:
<223> OTHER INFORMATION: Synthetically generated

<400> SEQUENCE: 150

```
Asn Thr Ala Pro Thr Asn Glu Thr Met Met Gln Tyr Phe Glu Trp Asp
1               5                  10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
```

-continued

```
                    85                      90                      95

Ile Gln Val Tyr Ala Asp Val Val Phe Asn His Lys Ala Gly Ala Asp
                100                     105                     110

Gly Thr Glu Phe Val Asp Ala Val Glu Val Asp Pro Ser Asn Arg Asn
                115                     120                     125

Gln Glu Val Ser Gly Thr Tyr Gln Ile Glu Ala Trp Thr Lys Phe Asp
        130                     135                     140

Phe Pro Gly Arg Gly Asn Thr Tyr Ser Ser Phe Lys Trp Arg Trp Tyr
145                     150                     155                     160

His Phe Asp Gly Thr Asp Trp Asp Glu Ser Arg Lys Leu Asn Arg Ile
                165                     170                     175

Tyr Lys Phe Arg Gly Lys Ala Trp Asp Trp Glu Val Asp Thr Glu Asn
                180                     185                     190

Gly Asn Tyr Asp Tyr Leu Met Phe Ala Asp Leu Asp Met Asp His Pro
                195                     200                     205

Glu Val Val Thr Glu Leu Lys Asn Trp Gly Thr Trp Tyr Val Asn Thr
        210                     215                     220

Thr Asn Ile Asp Gly Phe Arg Leu Asp Ala Val Lys His Ile Lys Phe
225                     230                     235                     240

Ser Phe Met Arg Asp Trp Leu Thr Tyr Val Arg Asn Gln Thr Gly Lys
                245                     250                     255

Asn Leu Phe Ala Val Gly Glu Phe Trp Lys Asn Asp Leu Gly Ala Leu
                260                     265                     270

Glu Asn Tyr Ile Thr Lys Thr Asn Gly Ser Met Ser Leu Phe Asp Ala
                275                     280                     285

Pro Leu His Asn Asn Phe Tyr Thr Ala Ser Lys Ser Ser Gly Tyr Phe
        290                     295                     300

Asp Met Arg Asn Leu Leu Asn Gly Thr Leu Val Gln Arg His Pro Ser
305                     310                     315                     320

His Ala Val Thr Leu Val Asp Asn His Asp Thr Gln Pro Gly Gln Ser
                325                     330                     335

Leu Gln Ser Trp Val Glu Pro Trp Phe Lys Pro Leu Ala Tyr Ala Phe
                340                     345                     350

Ile Leu Thr Arg Gln Glu Gly Tyr Pro Cys Val Phe Tyr Gly Asp Tyr
                355                     360                     365

Tyr Gly Ile Pro Lys Tyr Asn Ile Pro Gly Leu Lys Ser Lys Ile Asp
        370                     375                     380

Pro Leu Leu Ile Ala Arg Gln Asp Tyr Ala Tyr Gly Thr Gln Arg Asp
385                     390                     395                     400

Tyr Ile Asp His Gln Asp Ile Ile Gly Trp Thr Arg Glu Gly Asp Ser
                405                     410                     415

Ser His Pro Asn Ser Gly Leu Ala Ala Leu Ile Thr Asp Gly Pro Gly
                420                     425                     430

Gly Ser Lys Trp Met Tyr Val Gly Lys Lys His Ala Gly Lys Val Phe
                435                     440                     445

Tyr Asp Leu Thr Gly Asn Arg Ser Asp Thr Val Thr Ile Asn Ala Asp
        450                     455                     460

Gly Trp Gly Glu Phe Lys Val Asn Gly Gly Ser Val Ser Ile Trp Val
465                     470                     475                     480

Ala Lys
```

<210> SEQ ID NO 151
<211> LENGTH: 1446

-continued

<212> TYPE: DNA
<213> ORGANISM: Artificial Sequence
<220> FEATURE:
<223> OTHER INFORMATION: Synthetically generated

<400> SEQUENCE: 151

```
aatactgcac ctacgaacga aacaatgatg caatattttg aatgggattt accgaacgat       60
ggaacccttt ggaatagact ccataataat gcgcaaaacc ttaagaatgc aggtattaca      120
gcgttatggc ttcctccagc gtataaagga acaagtcaaa gcgatgtcgg atacggcgtg      180
tacgatttat atgaccttgg ggaatttaat caaaaaggaa cgattcgaac aaaatacgga      240
acaaaaacac aactggaacg cgcaattaga tccttaaaag ctaacggaat ccaagtatat      300
gcagatgttg tctttaatca taaggcggga gctgacggca cagaatttgt cgatgcggtt      360
gaggtagacc cttctaatcg aaatcaagaa gtgagcggaa cgtatcaaat tgaagcatgg      420
acaaaatttg attttcccgg tcgggggaac acatactcga gttttaaatg gcgttggtat      480
cattttgacg gtaccgattg ggatgaaagc cgaaaattaa atcggattta caaattccgc      540
ggaaaagcat gggactggga agtcgataca gaaaacggaa actatgatta tttaatgttc      600
gctgatttag atatggatca ccctgaggtt gtgacagaat taaaaaactg gggaacgtgg      660
tacgtcaata ctacaaatat cgatggattc cgcttagatg ccgtaaaaca tattaaattt      720
agttttatgc gggactggct aacatatgta cgtaatcaaa caggaaaaaa tttatttgcc      780
gttggggaat tttggaaaaa tgatttgggc gcgctcgaga attacattac aaaaacaaat      840
ggatcgatgt cattatttga tgcacctttg cataacaact tttataccgc ttccaaatcg      900
agtggatatt ttgacatgcg taatttgctg aacggaacgc ttgtccaacg acacccttct      960
cacgctgtga cacttgtcga taaccacgac acgcaaccag ggcaatcttt acagtcatgg     1020
gtcgaacctt ggtttaaacc acttgcttac gcctttattt taacgagaca agagggatat     1080
ccttgcgtat tttacggtga ctattatgga atcccgaaat acaatattcc aggattaaaa     1140
agcaaaatcg acccgctttt aattgctcgt caggactatg cctatggaac acaacgtgat     1200
tacattgacc atcaagacat tattggatgg acacgcgaag cgatagcag ccatccaaac      1260 tctggactgg cggctttaat taccgacggc cctggcggaa gcaaatggat gtatgtcggt     1320
aaaaaacatg ctggaaaagt attttatgat ttaaccggaa accgaagtga cacagtaacg     1380
attaatgcgg atggttgggg agaatttaaa gtaaacggag ctccgtttc gatttgggtg      1440 gctaaa                                                                1446
```

<210> SEQ ID NO 152
<211> LENGTH: 482
<212> TYPE: PRT
<213> ORGANISM: Artificial Sequence
<220> FEATURE:
<223> OTHER INFORMATION: Synthetically generated

<400> SEQUENCE: 152

```
Asn Thr Ala Pro Thr Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60
```

-continued

```
Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
                100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Lys Asn Asp Leu Gly Ala Leu
            260                 265                 270

Glu Asn Tyr Ile Thr Lys Thr Asn Gly Ser Met Ser Leu Phe Asp Ala
            275                 280                 285

Pro Leu His Asn Asn Phe Tyr Thr Ala Ser Lys Ser Ser Gly Tyr Phe
    290                 295                 300

Asp Met Arg Asn Leu Leu Asn Gly Thr Leu Val Gln Arg His Pro Ser
305                 310                 315                 320

His Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Asp Ser
                405                 410                 415

Ser His Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys
```

```
<210> SEQ ID NO 153
<211> LENGTH: 1446
<212> TYPE: DNA
<213> ORGANISM: Artificial Sequence
<220> FEATURE:
<223> OTHER INFORMATION: Synthetically generated

<400> SEQUENCE: 153
aatactgcac ctacgaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggaaaaa tgatttgggc gcgctcgaga attacattac aaaaacaaat     840
ggatcgatgt cattatttga tgcacctttg cataacaact tttataccgc ttccaaatcg     900
agtggatatt ttgacatgcg taatttgctg aacggaacgc ttgtccaacg acacccttct     960
cacgctgtga cacttgtcga taaccacgac acgcaaccag gcaatcttt acagtcatgg    1020 gtcgaacctt ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcgatagcag ccatccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaa                                                              1446

<210> SEQ ID NO 154
<211> LENGTH: 482
<212> TYPE: PRT
<213> ORGANISM: Artificial Sequence
<220> FEATURE:
<223> OTHER INFORMATION: Synthetically generated

<400> SEQUENCE: 154

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45
```

-continued

```
Lys Gly Thr Ser Gln Ser Asp Val Gly Tyr Gly Val Tyr Asp Leu Tyr
    50              55              60

Asp Leu Gly Glu Phe Asn Gln Lys Gly Thr Ile Arg Thr Lys Tyr Gly
65              70              75              80

Thr Lys Thr Gln Tyr Ile Gln Ala Ile Gln Ala Ala Lys Ala Ala Gly
                85              90              95

Met Gln Val Tyr Ala Asp Val Val Phe Asn His Lys Ala Gly Ala Asp
            100             105             110

Gly Thr Glu Phe Val Asp Ala Val Glu Val Asp Pro Ser Asn Arg Asn
        115             120             125

Gln Glu Thr Ser Gly Thr Tyr Gln Ile Gln Ala Trp Thr Lys Phe Asp
    130             135             140

Phe Pro Gly Arg Gly Asn Thr Tyr Ser Ser Phe Lys Trp Arg Trp Tyr
145             150             155             160

His Phe Asp Gly Thr Asp Trp Asp Glu Ser Arg Lys Leu Asn Arg Ile
            165             170             175

Tyr Lys Phe Arg Gly Lys Ala Trp Asp Trp Glu Val Asp Thr Glu Asn
            180             185             190

Gly Asn Tyr Asp Tyr Leu Met Phe Ala Asp Leu Asp Met Asp His Pro
        195             200             205

Glu Val Val Thr Glu Leu Lys Asn Trp Gly Thr Trp Tyr Val Asn Thr
    210             215             220

Thr Asn Ile Asp Gly Phe Arg Leu Asp Ala Val Lys His Ile Lys Tyr
225             230             235             240

Ser Phe Phe Arg Asp Trp Leu Thr Tyr Val Arg Asn Gln Thr Gly Lys
            245             250             255

Asn Leu Phe Ala Val Gly Glu Phe Trp Lys Tyr Asp Val Asn Ala Leu
            260             265             270

His Asn Tyr Ile Thr Lys Thr Asn Gly Ser Met Ser Leu Phe Asp Ala
        275             280             285

Pro Leu His Asn Asn Phe Tyr Thr Ala Ser Lys Ser Ser Gly Tyr Phe
    290             295             300

Asp Met Arg Tyr Leu Leu Asn Asn Thr Leu Met Lys Asp Gln Pro Ser
305             310             315             320

Leu Ala Val Thr Leu Val Asp Asn His Asp Thr Gln Pro Gly Gln Ser
            325             330             335

Leu Gln Ser Trp Val Glu Pro Trp Phe Lys Pro Leu Ala Tyr Ala Phe
            340             345             350

Ile Leu Thr Arg Gln Glu Gly Tyr Pro Cys Val Phe Tyr Gly Asp Tyr
        355             360             365

Tyr Gly Ile Pro Lys Tyr Asn Ile Pro Gly Leu Lys Ser Lys Ile Asp
    370             375             380

Pro Leu Leu Ile Ala Arg Arg Asp Tyr Ala Tyr Gly Thr Gln Arg Asp
385             390             395             400

Tyr Ile Asp His Gln Asp Ile Ile Gly Trp Thr Arg Glu Gly Ile Asp
            405             410             415

Thr Lys Pro Asn Ser Gly Leu Ala Ala Leu Ile Thr Asp Gly Pro Gly
            420             425             430

Gly Ser Lys Trp Met Tyr Val Gly Lys Lys His Ala Gly Lys Val Phe
        435             440             445

Tyr Asp Leu Thr Gly Asn Arg Ser Asp Thr Val Thr Ile Asn Ala Asp
    450             455             460
```

Gly Trp Gly Glu Phe Lys Val Asn Gly Gly Ser Val Ser Ile Trp Val
465                 470                 475                 480

Ala Lys

<210> SEQ ID NO 155
<211> LENGTH: 1446
<212> TYPE: DNA
<213> ORGANISM: Artificial Sequence
<220> FEATURE:
<223> OTHER INFORMATION: Synthetically generated

<400> SEQUENCE: 155
aatactgcac ctattaacga aacaatgatg caatattttg aatgggattt accgaacgat      60
ggaacccttt ggacaaaggt gaaaaatgaa gccgcaaatc tttcttcgct cggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aatatattca agccatccaa gctgccaaag ccgcagggat gcaagtatat     300
gcagatgttg tctttaatca taaggcggga gctgacggca cagaatttgt cgatgcggtt     360
gaggtagacc cttctaatcg aaatcaagaa acatctggaa catatcaaat tcaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaatac     720
agctttttcc gcgactggct aacatatgta cgtaatcaaa caggaaaaaa tttatttgcc     780
gttggggaat tttggaaata tgacgtcaat gcgctgcata attacattac aaaaacaaat     840
ggatcgatgt cattatttga tgcacctttg cataacaact tttataccgc ttccaaatcg     900
agtggatatt ttgacatgcg ttatttattg aataatacat taatgaaaga tcaaccttca     960
ctcgctgtga cacttgtcga taaccacgac acgcaaccag gcaatctttt acagtcatgg    1020
gtcgaacctt ggtttaaacc acttgcttac gcctttattt taacgagaca agagggatat    1080
ccttgcgtat tttacggtga ctattatgga atcccgaaat acaatattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag gctccgtttc gatttgggtg    1440
gctaaa                                                             1446

<210> SEQ ID NO 156
<211> LENGTH: 483
<212> TYPE: PRT
<213> ORGANISM: Artificial Sequence
<220> FEATURE:
<223> OTHER INFORMATION: Synthetically generated

<400> SEQUENCE: 156

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln

-continued

```
              20                25                30
Asn Leu Lys Asn Ala Gly Ile Thr Ala Leu Trp Leu Pro Pro Ala Tyr
          35                40                45
Lys Gly Thr Ser Gln Ser Asp Val Gly Tyr Gly Val Tyr Asp Leu Tyr
          50                55                60
Asp Leu Gly Glu Phe Asn Gln Lys Gly Thr Ile Arg Thr Lys Tyr Gly
65                70                75                80
Thr Lys Thr Gln Leu Glu Arg Ala Ile Arg Ser Leu Lys Ala Asn Gly
              85                90                95
Ile Gln Val Tyr Ala Asp Val Val Phe Asn His Lys Ala Gly Ala Asp
             100               105               110
Gly Thr Glu Phe Val Asp Ala Val Glu Val Asp Pro Ser Asn Arg Asn
             115               120               125
Gln Glu Val Ser Gly Thr Tyr Gln Ile Glu Ala Trp Thr Lys Phe Asp
         130               135               140
Phe Pro Gly Arg Gly Asn Thr Tyr Ser Ser Phe Lys Trp Arg Trp Tyr
145               150               155               160
His Phe Asp Gly Thr Asp Trp Asp Glu Ser Arg Ala Leu Gln Asn Arg
             165               170               175
Ile Tyr Lys Phe Arg Gly Lys Ala Trp Asp Trp Glu Val Asp Thr Glu
             180               185               190
Asn Gly Asn Tyr Asp Tyr Leu Met Phe Ala Asp Leu Asp Met Asp His
         195               200               205
Pro Glu Val Val Thr Glu Leu Gln His Trp Gly Thr Trp Tyr Val Asn
         210               215               220
Thr Thr Asn Ile Asp Gly Phe Arg Leu Asp Ala Val Lys His Ile Lys
225               230               235               240
Phe Ser Phe Met Arg Asp Trp Leu Thr Tyr Val Arg Asn Gln Thr Gly
             245               250               255
Lys Asn Leu Phe Ala Val Gly Glu Phe Trp Lys Asn Asp Leu Gly Ala
         260               265               270
Leu Glu Asn Tyr Ile Thr Lys Thr Asn Gly Ser Met Ser Leu Phe Asp
         275               280               285
Ala Pro Leu His Glu Asn Phe Tyr Thr Ala Ser Lys Ser Asn Gly Tyr
     290               295               300
Phe Asp Met Arg Asp Leu Leu Asn Gly Thr Leu Val Gln Arg His Pro
305               310               315               320
Ser His Ala Val Thr Phe Val Asp Asn His Asp Thr Asp Pro Glu Gln
             325               330               335
Ser Leu Asp Ser Trp Val Glu Glu Trp Phe Lys Pro Leu Ala Tyr Ala
         340               345               350
Phe Ile Leu Thr Arg Gln Glu Gly Tyr Pro Cys Val Phe Tyr Gly Asp
         355               360               365
Tyr Tyr Gly Ile Pro Lys Arg Asn Ile Pro Gly Leu Lys Ser Lys Ile
     370               375               380
Asp Pro Leu Leu Ile Ala Arg Arg Asp Tyr Ala Tyr Gly Thr Gln Arg
385               390               395               400
Asp Tyr Ile Asp His Gln Asp Ile Ile Gly Trp Thr Arg Glu Gly Ile
             405               410               415
Asp Thr Lys Pro Asn Ser Gly Leu Ala Ala Leu Ile Thr Asp Gly Pro
         420               425               430
Gly Gly Ser Lys Trp Met Tyr Val Gly Lys Lys His Ala Gly Lys Val
         435               440               445
```

-continued

```
Phe Tyr Asp Leu Thr Gly Asn Arg Ser Asp Thr Val Thr Ile Asn Ala
    450                 455                 460

Asp Gly Trp Gly Glu Phe Lys Val Asn Gly Gly Ser Val Ser Ile Trp
465                 470                 475                 480

Val Ala Lys

<210> SEQ ID NO 157
<211> LENGTH: 1449
<212> TYPE: DNA
<213> ORGANISM: Artificial Sequence
<220> FEATURE:
<223> OTHER INFORMATION: Synthetically generated

<400> SEQUENCE: 157
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgagcgttac agaatcggat ttacaaattc     540
cgcggaaaag catgggactg ggaagtcgat acagaaaacg gaaactatga ttatttaatg     600
ttcgctgatt tagatatgga tcaccctgag gttgtgacag aattacagca ttggggaacg     660
tggtacgtca atactacaaa tatcgatgga ttccgcttag atgccgtaaa acatattaaa     720
tttagtttta tgcgggactg gctaacatat gtacgtaatc aaacaggaaa aaatttattt     780
gccgttgggg aattttggaa aaatgatttg ggcgcgctcg agaattacat tacaaaaaca     840
aatggatcga tgtcattatt tgatgcacct ttgcatgaaa acttttatac cgcttccaaa     900
tcgaacggat attttgacat gcgtgatttg ctgaacggaa cgcttgtcca acgacaccct     960
tctcacgctg tgacatttgt cgataaccac gacacggatc cagaacaatc tttagattca    1020
tgggtcgaag aatggtttaa accacttgct tacgcctta ttttaacgag acaagaggga    1080
tatccttgcg tattttacgg tgactattat ggaatcccga aacgcaatat tccaggatta    1140
aaaagcaaaa tcgacccgct tttaattgct cgtcgggact atgcctatgg aacacaacgt    1200
gattacattg accatcaaga cattattgga tggacacgcg aaggcattga tacaaaacca    1260
aactctggac tggcggcttt aattaccgac ggccctggcg gaagcaaatg gatgtatgtc    1320
ggtaaaaaac atgctggaaa agtattttat gatttaaccg aaaccgaag tgacacagta    1380 acgattaatg cggatggttg gggagaattt aaagtaaacg gaggctccgt ttcgatttgg    1440
gtggctaaa                                                            1449

<210> SEQ ID NO 158
<211> LENGTH: 482
<212> TYPE: PRT
<213> ORGANISM: Artificial Sequence
<220> FEATURE:
<223> OTHER INFORMATION: Synthetically generated

<400> SEQUENCE: 158
```

-continued

```
Asn Thr Ala Pro Ile Asn Glu Thr Met Met Gln Tyr Phe Glu Trp Asp
1               5                   10                  15

Leu Pro Asp Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
            85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Ser Leu Asn Arg Ile
            165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Gln Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
            245                 250                 255

Asn Leu Phe Ala Val Gly Glu Phe Trp Lys Asp Asp Leu Gly Ala Leu
            260                 265                 270

Glu Asn Tyr Ile Thr Lys Thr Asn Gly Ser Met Ser Leu Phe Asp Ala
    275                 280                 285

Pro Leu His Asn Asn Phe Tyr Thr Ala Ser Lys Ser Asp Gly Tyr Phe
    290                 295                 300

Asp Met Arg Asn Leu Leu Asn Gly Thr Leu Val Glu Arg His Pro Ser
305                 310                 315                 320

His Ala Val Thr Leu Val Asp Glu His Asp Thr Gln Pro Gly Glu Ser
            325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asp Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
            405                 410                 415

Thr Lys Pro Asn Ser Gly Leu Ala Ala Leu Ile Thr Asp Gly Pro Gly
```

-continued

```
              420              425              430
Gly Ser Lys Trp Met Tyr Val Gly Lys Lys His Ala Gly Lys Val Phe
        435              440              445

Tyr Asp Leu Thr Gly Asn Arg Ser Asp Thr Val Thr Ile Asn Ala Asp
    450              455              460

Gly Trp Gly Glu Phe Lys Val Asn Gly Gly Ser Val Ser Ile Trp Val
465              470              475              480

Ala Lys
```

<210> SEQ ID NO 159
<211> LENGTH: 1446
<212> TYPE: DNA
<213> ORGANISM: Artificial Sequence
<220> FEATURE:
<223> OTHER INFORMATION: Synthetically generated

<400> SEQUENCE: 159

```
aatactgcac ctattaacga aacaatgatg caatattttg aatgggattt accggatgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaagcttaa atcggattta caaattccgc     540
ggaaaagcat gggactggga agtcgataca gaaaacggaa actatgatta tttaatgttc     600
gctgatttag atatggatca ccctgaggtt gtgacagaat tacagaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggaaaga tgatttgggc gcgctcgaga attacattac aaaaacaaat     840
ggatcgatgt cattatttga tgcacctttg cataacaact tttataccgc ttccaaatcg     900
gatggatatt ttgacatgcg taatttgctg aacggaacgc ttgtcgaacg acacccttct     960
cacgctgtga cacttgtcga tgaacacgac acgcaaccag gggaatcttt acagtcatgg    1020
gtcgaacctt ggtttaaacc acttgcttac gcctttattt taacgagaca agagggatat    1080
ccttgcgtat tttacggtga ctattatgga atcccgaaat acgatattcc aggattaaaa    1140
agcaaaatcg acccgctttt aattgctcgt cgggactatg cctatggaac aaacgtgat    1200 tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt attttatgat ttaaccggaa accgaagtga cacagtaacg    1380
attaatgcgg atggttgggg agaatttaaa gtaaacggag ctccgtttc gatttgggtg    1440 gctaaa                                                              1446
```

<210> SEQ ID NO 160
<211> LENGTH: 483
<212> TYPE: PRT
<213> ORGANISM: Artificial Sequence
<220> FEATURE:

<223> OTHER INFORMATION: Synthetically generated

<400> SEQUENCE: 160

```
Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Thr Leu Gln Asn Arg
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Phe Ala Asp Leu Asp Met Asp His
            195                 200                 205

Pro Glu Val Val Thr Glu Leu Gln Lys Trp Gly Thr Trp Tyr Val Asn
    210                 215                 220

Thr Thr Asn Ile Asp Gly Phe Arg Leu Asp Ala Val Lys His Ile Lys
225                 230                 235                 240

Phe Ser Phe Met Arg Asp Trp Leu Thr Tyr Val Arg Asn Gln Thr Gly
                245                 250                 255

Lys Asn Leu Phe Ala Val Gly Glu Phe Trp Lys Asn Asp Leu Gly Ala
                260                 265                 270

Leu Glu Asn Tyr Ile Thr Lys Thr Asn Gly Ser Met Ser Leu Phe Asp
        275                 280                 285

Ala Pro Leu His Asn Glu Phe Tyr Thr Ala Ser Lys Ser Asn Gly Tyr
    290                 295                 300

Phe Asp Met Arg Glu Leu Leu Glu Gly Thr Leu Val Gln Arg His Pro
305                 310                 315                 320

Ser His Ala Val Thr Tyr Val Asp Asn His Asp Thr Gln Pro Glu Gln
                325                 330                 335

Ser Leu Gln Ser Trp Val Glu Glu Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Lys Tyr Asn Ile Pro Gly Leu Lys Ser Lys Ile
    370                 375                 380

Asp Pro Leu Leu Ile Ala Arg Arg Asp Tyr Ala Tyr Gly Thr Gln Arg
385                 390                 395                 400
```

```
Asp Tyr Ile Asp His Gln Asp Ile Ile Gly Trp Thr Arg Glu Gly Ile
            405                 410                 415

Asp Thr Lys Pro Asn Ser Gly Leu Ala Ala Leu Ile Thr Asp Gly Pro
            420                 425                 430

Gly Gly Ser Lys Trp Met Tyr Val Gly Lys Lys His Ala Gly Lys Val
        435                 440                 445

Phe Tyr Asp Leu Thr Gly Asn Arg Ser Asp Thr Val Thr Ile Asn Ala
    450                 455                 460

Asp Gly Trp Gly Glu Phe Lys Val Asn Gly Gly Ser Val Ser Ile Trp
465                 470                 475                 480

Val Ala Lys
```

<210> SEQ ID NO 161
<211> LENGTH: 1449
<212> TYPE: DNA
<213> ORGANISM: Artificial Sequence
<220> FEATURE:
<223> OTHER INFORMATION: Synthetically generated

<400> SEQUENCE: 161

```
aatactgcac ctattaacga aacaatgatg caatattttg aatgggattt accgaacgat     60
ggaacccttt ggaatagact ccataataat gcgcaaaacc ttaagaatgc aggtattaca    120
gcgttatggc ttcctccagc gtataaagga acaagtcaaa gcgatgtcgg atacggcgtg    180
tacgatttat atgaccttgg ggaatttaat caaaaaggaa cgattcgaac aaaatacgga    240
acaaaaacac aactggaacg cgcaattaga tccttaaaag ctaacggaat ccaagtatat    300
gcagatgttg tctttaatca taaggcggga gctgacggca cagaatttgt cgatgcggtt    360
gaggtagacc cttctaatcg aaatcaagaa gtgagcggaa cgtatcaaat tgaagcatgg    420
acaaaatttg attttcccgg tcgggggaac acatactcga gttttaaatg gcgttggtat    480
cattttgacg gtaccgattg ggatgaaagc cgaacgttac agaatcggat ttacaaattc    540
cgcggaaaag catgggactg ggaagtcgat acagaaaacg gaaactatga ttatttaatg    600
ttcgctgatt tagatatgga tcaccctgag gttgtgacag aattacgaaa atggggaacg    660
tggtacgtca atactacaaa tatcgatgga ttccgcttag atgccgtaaa acatattaaa    720
tttagtttta tgcgggactg gctaacatat gtacgtaatc aaacaggaaa aaatttattt    780
gccgttgggg aattttggaa aaatgatttg ggcgcgctcg agaattacat tacaaaaaca    840
aatggatcga tgtcattatt tgatgcacct ttgcataacg aattttatac cgcttccaaa    900
tcgaacggat attttgacat gcgtgaattg ctggaaggaa cgcttgtcca acgacaccct    960
tctcacgctg tgacatatgt cgataaccac gacacgcaac cagaacaatc tttacagtca   1020
tgggtcgaag aatggtttaa accacttgct tacgccttta ttttaacgag acaagaggga   1080
tatccttgcg tattttacgg tgactattat ggaatcccga aatacaatat tccaggatta   1140
aaaagcaaaa tcgacccgct tttaattgct cgtcgggact atgcctatgg aacacaacgt   1200
gattacattg accatcaaga cattattgga tggacacgcg aaggcattga tacaaaacca   1260
aactctggac tggcggcttt aattaccgac ggccctggcg aagcaaatg gatgtatgtc    1320
ggtaaaaaac atgctggaaa agtattttat gatttaaccg aaaccgaag tgacacagta    1380
acgattaatg cggatggttg gggagaattt aaagtaaacg gaggctccgt ttcgatttgg    1440
gtggctaaa                                                           1449
```

<210> SEQ ID NO 162

```
<211> LENGTH: 483
<212> TYPE: PRT
<213> ORGANISM: Artificial Sequence
<220> FEATURE:
<223> OTHER INFORMATION: Synthetically generated

<400> SEQUENCE: 162

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
            85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Gln Asn Arg
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Phe Ala Asp Leu Asp Met Asp His
        195                 200                 205

Pro Glu Val Val Thr Glu Leu Lys Asn Trp Gly Thr Trp Tyr Val Asn
    210                 215                 220

Thr Thr Asn Ile Asp Gly Phe Arg Leu Asp Ala Val Lys His Ile Lys
225                 230                 235                 240

Phe Ser Phe Met Arg Asp Trp Leu Thr Tyr Val Arg Asn Gln Thr Gly
                245                 250                 255

Lys Asn Leu Phe Ala Val Gly Glu Phe Trp Lys Asp Asp Leu Gly Ala
            260                 265                 270

Leu Glu Asn Tyr Ile Thr Lys Thr Asn Gly Ser Met Ser Leu Phe Asp
        275                 280                 285

Ala Pro Leu His Asn Asn Phe Tyr Thr Ala Ser Lys Ser Ser Gly Tyr
    290                 295                 300

Phe Asp Met Arg Asn Leu Leu Asn Gly Thr Leu Val Gln Arg His Pro
305                 310                 315                 320

Ser His Ala Val Thr Leu Val Asp Asn His Asp Thr Asp Pro Gly Gln
                325                 330                 335

Ser Leu Glu Ser Trp Val Glu Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Lys Tyr Glu Ile Pro Gly Leu Lys Ser Lys Ile
    370                 375                 380
```

```
Asp Pro Leu Leu Ile Ala Arg Arg Asp Tyr Ala Tyr Gly Thr Gln Arg
385                 390                 395                 400

Asp Tyr Ile Asp His Gln Asp Ile Ile Gly Trp Thr Arg Glu Gly Ile
                    405                 410                 415

Asp Thr Lys Pro Asn Ser Gly Leu Ala Ala Leu Ile Thr Asp Gly Pro
                420                 425                 430

Gly Gly Ser Lys Trp Met Tyr Val Gly Lys Lys His Ala Gly Lys Val
            435                 440                 445

Phe Tyr Asp Leu Thr Gly Asn Arg Ser Asp Thr Val Thr Ile Asn Ala
        450                 455                 460

Asp Gly Trp Gly Glu Phe Lys Val Asn Gly Gly Ser Val Ser Ile Trp
465                 470                 475                 480

Val Ala Lys
```

```
<210> SEQ ID NO 163
<211> LENGTH: 1449
<212> TYPE: DNA
<213> ORGANISM: Artificial Sequence
<220> FEATURE:
<223> OTHER INFORMATION: Synthetically generated

<400> SEQUENCE: 163
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattac agaatcggat ttacaaattc     540
cgcggaaaag catgggactg ggaagtcgat acagaaaacg gaaactatga ttatttaatg     600
ttcgctgatt tagatatgga tcaccctgag gttgtgacag aattaaaaaa ctggggaacg     660
tggtacgtca atactacaaa tatcgatgga ttccgcttag atgccgtaaa acatattaaa     720
tttagtttta tgcgggactg gctaacatat gtacgtaatc aaacaggaaa aaatttattt     780
gccgttgggg aattttggaa agatgatttg ggcgcgctcg agaattacat tacaaaaaca     840
aatggatcga tgtcattatt tgatgcacct ttgcataaca acttttatac cgcttccaaa     900
tcgagtggat attttgacat gcgtaatttg ctgaacggaa cgcttgtcca acgacaccct     960
tctcacgctg tgacacttgt cgataaccac gacacggatc cagggcaatc tttagaatca    1020
tgggtcgaac cttggtttaa accacttgct tacgcctttg tttttaacgag acaagaggga    1080 tatccttgcg tattttacgg tgactattat ggaatcccga atacgaaaat tccaggatta    1140
aaaagcaaaa tcgacccgct ttttaattgct cgtcgggact atgcctatgg aacacaacgt    1200
gattacattg accatcaaga cattattgga tggacacgcg aaggcattga tacaaaacca    1260
aactctggac tggcggcttt aattaccgac ggccctggcg gaagcaaatg gatgtatgtc    1320
ggtaaaaaac atgctggaaa agtatttat gatttaaccg gaaaccgaag tgacacagta    1380
acgattaatg cggatggttg gggagaattt aaagtaaacg gaggctccgt ttcgatttgg    1440
```

-continued gtggctaaa                                                                    1449

<210> SEQ ID NO 164
<211> LENGTH: 482
<212> TYPE: PRT
<213> ORGANISM: Artificial Sequence
<220> FEATURE:
<223> OTHER INFORMATION: Synthetically generated

<400> SEQUENCE: 164

Asn Thr Ala Pro Ile Asn Glu Thr Met Met Gln Tyr Phe Glu Trp Asp
1               5                   10                  15

Leu Pro Glu Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Lys Glu Asp Leu Gly Ala Leu
            260                 265                 270

Glu Asn Tyr Ile Thr Lys Thr Asn Gly Ser Met Ser Leu Phe Asp Ala
            275                 280                 285

Pro Leu His Glu Asn Phe Tyr Thr Ala Ser Lys Ser Ser Gly Tyr Phe
    290                 295                 300

Asp Met Arg Glu Leu Leu Asn Gly Thr Leu Val Glu Arg His Pro Ser
305                 310                 315                 320

His Ala Val Thr Leu Val Asp Glu His Asp Thr Gln Pro Gly Gln Ser
                325                 330                 335

Leu Glu Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr

-continued

```
            355               360               365

Tyr Gly Ile Pro Lys Tyr Glu Ile Pro Gly Leu Lys Ser Lys Ile Asp
    370               375               380

Pro Leu Leu Ile Ala Arg Arg Asp Tyr Ala Tyr Gly Thr Gln Arg Asp
385               390               395               400

Tyr Ile Asp His Gln Asp Ile Ile Gly Trp Thr Arg Glu Gly Ile Asp
            405               410               415

Thr Lys Pro Asn Ser Gly Leu Ala Ala Leu Ile Thr Asp Gly Pro Gly
            420               425               430

Gly Ser Lys Trp Met Tyr Val Gly Lys Lys His Ala Gly Lys Val Phe
            435               440               445

Tyr Asp Leu Thr Gly Asn Arg Ser Asp Thr Val Thr Ile Asn Ala Asp
    450               455               460

Gly Trp Gly Glu Phe Lys Val Asn Gly Gly Ser Val Ser Ile Trp Val
465               470               475               480

Ala Lys
```

```
<210> SEQ ID NO 165
<211> LENGTH: 1446
<212> TYPE: DNA
<213> ORGANISM: Artificial Sequence
<220> FEATURE:
<223> OTHER INFORMATION: Synthetically generated

<400> SEQUENCE: 165
aatactgcac ctattaacga aacaatgatg caatattttg aatgggattt accggaagat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaaaactg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggaaaga agatttgggc gcgctcgaga attacattac aaaaacaaat     840
ggatcgatgt cattatttga tgcacctttg catgaaaact tttataccgc ttccaaatcg     900
agtggatatt ttgacatgcg tgaattgctg aacggaacgc ttgtcgaacg acacccttct     960
cacgctgtga cacttgtcga tgaacacgac acgcaaccag gcaatctttt agaatcatgg    1020
gtcgaacctt ggtttaaacc acttgcttac gcctttattt taacgagaca agagggatat    1080
ccttgcgtat tttacggtga ctattatgga atcccgaaat acgaaattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
```

-continued

```
aaaaaacatg ctggaaaagt attttatgat ttaaccggaa accgaagtga cacagtaacg     1380
attaatgcgg atggttgggg agaatttaaa gtaaacggag ctccgtttc gatttgggtg     1440 gctaaa                                                              1446
```

```
<210> SEQ ID NO 166
<211> LENGTH: 483
<212> TYPE: PRT
<213> ORGANISM: Artificial Sequence
<220> FEATURE:
<223> OTHER INFORMATION: Synthetically generated

<400> SEQUENCE: 166

Asn Thr Ala Pro Ile Asn Glu Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Ala Leu Gln Asn Arg
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Phe Ala Asp Leu Asp Met Asp His
            195                 200                 205

Pro Glu Val Val Thr Glu Leu Asn Arg Trp Gly Thr Trp Tyr Val Asn
        210                 215                 220

Thr Thr Asn Ile Asp Gly Phe Arg Leu Asp Ala Val Lys His Ile Lys
225                 230                 235                 240

Phe Ser Phe Met Arg Asp Trp Leu Thr Tyr Val Arg Asn Gln Thr Gly
                245                 250                 255

Lys Asn Leu Phe Ala Val Gly Glu Phe Trp Lys Asn Asp Leu Gly Ala
            260                 265                 270

Leu Glu Asn Tyr Ile Thr Lys Thr Asn Gly Ser Met Ser Leu Phe Asp
        275                 280                 285

Ala Pro Leu His Asn Asn Phe Tyr Thr Ala Ser Lys Ser Asp Gly Tyr
    290                 295                 300

Phe Asp Met Arg Asn Leu Leu Asn Gly Thr Leu Val Gln Arg His Pro
305                 310                 315                 320

Ser His Ala Val Thr Phe Val Asp Asn His Asp Thr Gln Pro Gly Gln
                325                 330                 335
```

-continued

```
Ser Leu Gln Ser Trp Val Glu Glu Trp Phe Lys Pro Leu Ala Tyr Ala
        340                 345                 350

Phe Ile Leu Thr Arg Gln Glu Gly Tyr Pro Cys Val Phe Tyr Gly Asp
        355                 360                 365

Tyr Tyr Gly Ile Pro Lys Tyr Asn Ile Pro Gly Leu Lys Ser Lys Ile
        370                 375                 380

Asp Pro Leu Leu Ile Ala Arg Arg Asp Tyr Ala Tyr Gly Thr Gln Arg
385                 390                 395                 400

Asp Tyr Ile Asp His Gln Asp Ile Ile Gly Trp Thr Arg Glu Gly Ile
                405                 410                 415

Asp Thr Lys Pro Asn Ser Gly Leu Ala Ala Leu Ile Thr Asp Gly Pro
                420                 425                 430

Gly Gly Ser Lys Trp Met Tyr Val Gly Lys Lys His Ala Gly Lys Val
        435                 440                 445

Phe Tyr Asp Leu Thr Gly Asn Arg Ser Asp Thr Val Thr Ile Asn Ala
        450                 455                 460

Asp Gly Trp Gly Glu Phe Lys Val Asn Gly Gly Ser Val Ser Ile Trp
465                 470                 475                 480

Val Ala Lys
```

```
<210> SEQ ID NO 167
<211> LENGTH: 1449
<212> TYPE: DNA
<213> ORGANISM: Artificial Sequence
<220> FEATURE:
<223> OTHER INFORMATION: Synthetically generated

<400> SEQUENCE: 167
aatactgcac ctattaacga aacaatgatg caatattttg aatgggattt accgaacgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgagcgttac agaatcggat ttacaaattc     540
cgcggaaaag catgggactg ggaagtcgat acagaaaacg gaaactatga ttatttaatg     600
ttcgctgatt tagatatgga tcaccctgag gttgtgacag aattaaaccg ctggggaacg     660
tggtacgtca atactacaaa tatcgatgga ttccgcttag atgccgtaaa acatattaaa     720
tttagtttta tgcgggactg gctaacatat gtacgtaatc aaacaggaaa aaatttattt     780
gccgttgggg aattttggaa aaatgatttg ggcgcgctcg agaattacat tacaaaaaca     840
aatggatcga tgtcattatt tgatgcacct ttgcataaca acttttatac cgcttccaaa     900
tcggatggat attttgacat gcgtaatttg ctgaacggaa cgcttgtcca acgacaccct     960
tctcacgctg tgacatttgt cgataaccac gacacgcaac cagggcaatc tttacagtca    1020
tgggtcgaag aatggtttaa accacttgct tacgccttta ttttaacgag acaagaggga    1080
tatccttgcg tattttacgg tgactattat ggaatcccga aatacaatat tccaggatta    1140
aaaagcaaaa tcgacccgct tttaattgct cgtcgggact atgcctatgg aacacaacgt    1200
```

-continued

```
gattacattg accatcaaga cattattgga tggacacgcg aaggcattga tacaaaacca    1260
aactctggac tggcggcttt aattaccgac ggccctggcg aagcaaatg gatgtatgtc     1320 ggtaaaaaac atgctggaaa agtattttat gatttaaccg aaaccgaag tgacacagta     1380 acgattaatg cggatggttg gggagaattt aaagtaaacg gaggctccgt ttcgatttgg     1440
gtggctaaa                                                             1449
```

<210> SEQ ID NO 168
<211> LENGTH: 482
<212> TYPE: PRT
<213> ORGANISM: Artificial Sequence
<220> FEATURE:
<223> OTHER INFORMATION: Synthetically generated

<400> SEQUENCE: 168

```
Asn Thr Ala Pro Ile Asn Glu Thr Met Met Gln Tyr Phe Glu Trp Asp
1               5                   10                  15

Leu Pro Asp Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Leu Glu Arg Ala Ile Arg Ser Leu Lys Ala Asn Gly
                85                  90                  95

Ile Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
            115                 120                 125

Gln Glu Val Ser Gly Thr Tyr Gln Ile Glu Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
            195                 200                 205

Glu Val Val Thr Glu Leu Asn Arg Trp Gly Thr Trp Tyr Val Asn Thr
        210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Lys Glu Asp Leu Gly Ala Leu
            260                 265                 270

Glu Asn Tyr Ile Thr Lys Thr Asn Gly Ser Met Ser Leu Phe Asp Ala
            275                 280                 285

Pro Leu His Glu Asn Phe Tyr Thr Ala Ser Lys Ser Ser Gly Tyr Phe
        290                 295                 300

Asp Met Arg Glu Leu Leu Asn Gly Thr Leu Val Gln Arg His Pro Ser
305                 310                 315                 320
```

-continued

```
His Ala Val Thr Leu Val Asp Glu His Asp Thr Gln Pro Gly Gln Ser
            325                 330                 335

Leu Glu Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
            355                 360                 365

Tyr Gly Ile Pro Lys Tyr Glu Ile Pro Gly Leu Lys Ser Lys Ile Asp
        370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
            435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Ala Lys

<210> SEQ ID NO 169
<211> LENGTH: 1446
<212> TYPE: DNA
<213> ORGANISM: Artificial Sequence
<220> FEATURE:
<223> OTHER INFORMATION: Synthetically generated

<400> SEQUENCE: 169
aatactgcac ctattaacga aacaatgatg caatattttg aatgggattt accggatgat      60
ggaacccttt ggaatagact ccataataat gcgcaaaacc ttaagaatgc aggtattaca     120
gcgttatggc ttcctccagc gtataaagga acaagtcaaa gcgatgtcgg atacggcgtg     180
tacgatttat atgaccttgg ggaatttaat caaaaaggaa cgattcgaac aaaatacgga     240
acaaaaacac aactggaacg cgcaattaga tccttaaaag ctaacggaat ccaagtatat     300
gcagatgttg tctttaatca taaggcggga gctgacggca cagaatttgt cgatgcggtt     360
gaggtagacc cttctaatcg aaatcaagaa gtgagcggaa cgtatcaaat tgaagcatgg     420
acaaaatttg attttcccgg tcgggggaac acatactcga gttttaaatg gcgttggtat     480
cattttgacg gtaccgattg ggatgaaagc cgaaaattaa atcggattta caaattccgc     540
ggaaaagcat gggactggga agtcgataca gaaaacggaa actatgatta tttaatgttc     600
gctgatttag atatggatca ccctgaggtt gtgacagaat taaaccgctg gggaacgtgg     660
tacgtcaata ctacaaatat cgatggattc cgcttagatg ccgtaaaaca tattaaattt     720
agttttatgc gggactggct aacatatgta cgtaatcaaa caggaaaaaa tttatttgcc     780
gttggggaat tttggaaaga agatttgggc gcgctcgaga attacattac aaaaacaaat     840
ggatcgatgt cattatttga tgcacctttg catgaaaact tttataccgc ttccaaatcg     900
agtggatatt ttgacatgcg tgaattgctg aacggaacgc ttgtccaacg acaccccttct   960 cacgctgtga cacttgtcga tgaacacgac acgcaaccag ggcaatcttt agaatcatgg    1020
gtcgaacctt ggtttaaacc acttgcttac gcctttattt taacgagaca agagggtatt   1080
```

```
ccttgcgtat tttacggtga ctattatgga atcccgaaat acgaaattcc aggattaaaa    1140
agcaaaatcg acccgctttt aattgctcgt cgggactatg cctatggaac acaacgtgat    1200
tacattgacc atcaagacat tattggatgg acacgcgaag gcattgatac aaaaccaaac    1260
tctggactgg cggctttaat taccgacggc cctggcggaa gcaaatggat gtatgtcggt    1320
aaaaaacatg ctggaaaagt atttatgat ttaaccggaa accgaagtga cacagtaacg    1380
attaatgcgg atggttgggg agaatttaaa gtaaacggag ctccgtttc gatttgggtg     1440 gctaaa                                                               1446
```

<210> SEQ ID NO 170
<211> LENGTH: 482
<212> TYPE: PRT
<213> ORGANISM: Artificial Sequence
<220> FEATURE:
<223> OTHER INFORMATION: Synthetically generated

<400> SEQUENCE: 170

```
His His Asn Gly Thr Asn Gly Thr Met Met Gln Tyr Phe Glu Trp Asp
1               5                   10                  15

Leu Pro Asn Asp Gly Thr Leu Trp Asn Arg Leu His Asn Asn Ala Gln
            20                  25                  30

Asn Leu Lys Asn Ala Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gln Thr Glu Phe Val Asp Ala Val Glu Val Asp Pro Ser Asn Arg Asn
        115                 120                 125

Gln Glu Val Ser Gly Thr Tyr Gln Ile Glu Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Phe
225                 230                 235                 240

Ser Phe Met Arg Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Asn Phe
```

-continued

```
          290              295              300

Asp Met Arg Asn Leu Leu Asn Gly Thr Leu Val Gln Arg His Pro Ser
305             310              315              320

His Ala Val Thr Leu Val Asp Asn His Asp Thr Gln Pro Gly Gln Ser
            325              330              335

Leu Gln Ser Trp Val Glu Pro Trp Phe Lys Pro Leu Ala Tyr Ala Phe
            340              345              350

Ile Leu Thr Arg Gln Glu Gly Tyr Pro Cys Val Phe Tyr Gly Asp Tyr
            355              360              365

Tyr Gly Ile Pro Ser Asp Gly Val Pro Gly Leu Lys Ser Lys Ile Asp
        370              375              380

Pro Leu Leu Ile Ala Arg Arg Asp Tyr Ala Tyr Gly Thr Gln Arg Asp
385              390              395              400

Tyr Ile Asp His Gln Asp Ile Ile Gly Trp Thr Arg Glu Gly Ile Asp
                405              410              415

Thr Lys Pro Asn Ser Gly Leu Ala Ala Leu Ile Thr Asp Gly Pro Gly
            420              425              430

Gly Ser Lys Trp Met Tyr Val Gly Lys Lys His Ala Gly Lys Val Phe
            435              440              445

Tyr Asp Leu Thr Gly Asn Arg Ser Asp Thr Val Thr Ile Asn Ala Asp
        450              455              460

Gly Trp Gly Glu Phe Lys Val Asn Gly Gly Ser Val Ser Ile Trp Val
465              470              475              480

Ala Lys

<210> SEQ ID NO 171
<211> LENGTH: 482
<212> TYPE: PRT
<213> ORGANISM: Artificial Sequence
<220> FEATURE:
<223> OTHER INFORMATION: Synthetically generated

<400> SEQUENCE: 171

His His Asn Gly Thr Asn Gly Thr Met Met Gln Tyr Phe Glu Trp Asp
1               5               10              15

Leu Pro Asn Asp Gly Thr Leu Trp Asn Arg Leu His Asn Asn Ala Gln
            20              25              30

Asn Leu Lys Asn Ala Gly Ile Thr Ala Leu Trp Leu Pro Pro Ala Tyr
            35              40              45

Lys Gly Thr Ser Gln Ser Asp Val Gly Tyr Gly Val Tyr Asp Leu Tyr
        50              55              60

Asp Leu Gly Glu Phe Asn Gln Lys Gly Thr Ile Arg Thr Lys Tyr Gly
65              70              75              80

Thr Lys Thr Gln Leu Glu Arg Ala Ile Arg Ser Leu Lys Ala Asn Gly
                85              90              95

Ile Gln Val Tyr Ala Asp Val Val Phe Asn His Lys Ala Gly Ala Asp
            100             105             110

Gly Thr Glu Phe Val Asp Ala Val Glu Val Asp Pro Ser Asn Arg Asn
            115             120             125

Gln Glu Val Ser Gly Thr Tyr Gln Ile Glu Ala Trp Thr Lys Phe Asp
        130             135             140

Phe Pro Gly Arg Gly Asn Thr Tyr Ser Ser Phe Lys Trp Arg Trp Tyr
145             150             155             160

His Phe Asp Gly Thr Asp Trp Asp Glu Ser Arg Lys Leu Asn Arg Ile
                165             170             175
```

-continued

```
Tyr Lys Phe Arg Gly Lys Ala Trp Asp Trp Glu Val Asp Thr Glu Asn
            180             185             190

Gly Asn Tyr Asp Tyr Leu Met Phe Ala Asp Leu Asp Met Asp His Pro
            195             200             205

Glu Val Val Thr Glu Leu Lys Asn Trp Gly Thr Trp Tyr Val Asn Thr
    210             215             220

Thr Asn Ile Asp Gly Phe Arg Leu Asp Ala Val Lys His Ile Lys Phe
225             230             235             240

Ser Phe Met Arg Asp Trp Leu Thr Tyr Val Arg Asn Gln Thr Gly Lys
            245             250             255

Asn Leu Phe Ala Val Gly Glu Phe Trp Lys Asn Asp Leu Gly Ala Leu
            260             265             270

Glu Asn Tyr Ile Thr Lys Thr Asn Gly Ser Met Ser Leu Phe Asp Ala
            275             280             285

Pro Leu His Asn Asn Phe Tyr Thr Ala Ser Lys Ser Ser Gly Asn Phe
    290             295             300

Asp Met Arg Asn Leu Leu Asn Gly Thr Leu Val Gln Arg His Pro Ser
305             310             315             320

His Ala Val Thr Leu Val Asp Asn His Asp Thr Gln Pro Gly Gln Ser
            325             330             335

Leu Gln Ser Trp Val Glu Pro Trp Phe Lys Pro Leu Ala Tyr Ala Phe
            340             345             350

Ile Leu Thr Arg Gln Glu Gly Tyr Pro Cys Val Phe Tyr Gly Asp Tyr
            355             360             365

Tyr Gly Ile Pro Lys Tyr Asn Ile Pro Gly Leu Lys Ser Lys Ile Asp
    370             375             380

Pro Leu Leu Ile Ala Arg Arg Asp Tyr Ala Tyr Gly Thr Gln Arg Asp
385             390             395             400

Tyr Ile Asp His Gln Asp Ile Ile Gly Trp Thr Arg Glu Gly Ile Asp
            405             410             415

Thr Lys Pro Asn Ser Gly Leu Ala Ala Leu Ile Thr Asp Gly Pro Gly
            420             425             430

Gly Ser Lys Trp Met Tyr Val Gly Lys Lys His Ala Gly Lys Val Phe
            435             440             445

Tyr Asp Leu Thr Gly Asn Arg Ser Asp Thr Val Thr Ile Asn Ala Asp
    450             455             460

Gly Trp Gly Glu Phe Lys Val Lys Gly Gly Ser Val Ser Ile Trp Val
465             470             475             480

Ala Lys
```

AMYLASE ENZYMES

CROSS-REFERENCE TO RELATED APPLICATIONS

This is the U.S. national phase of International Application No. PCT/EP2020/058129, filed Mar. 24, 2020, which claims priority to U.S. Patent Application No. 62/823,538, filed Mar. 25, 2019, and U.S. Patent Application No. 62/890,325, filed Aug. 22, 2019.

SEQUENCE LISTING

Incorporation by Reference of Material Submitted Electronically

The Sequence Listing, which is a part of the present disclosure, is submitted concurrently with the specification as a text file. The name of the text file containing the Sequence Listing is "190286_Seqlisting.txt", which was created on Sep. 15, 2021 and is 447,722 bytes in size. The subject matter of the Sequence Listing is incorporated herein in its entirety by reference.

Technical Field

Genetically engineered amylase enzymes, compositions comprising the enzymes, and methods of using the enzymes or compositions comprising the enzymes. The genetically engineered amylase enzymes are useful in many different applications such as laundry detergents, dish washing detergents, and cleaning products for homes, industry, vehicle care, baking, animal feed, pulp and paper processing, starch processing, and ethanol production. Amylases have been employed in the removal of starch stains and have been added to various compositions such as cleaning products. Current cleaning and/or fabric care compositions comprise formulations of many active ingredients that impact with the ability of amylases to remove starch stains; however, many of these amylases do not retain activity especially at high temperatures such as 80 degrees C. or 90 degrees C. In addition, many of the enzymes do not retain activity in detergent formulations. These decreases in activity because of high temperatures or other formulations can negatively impact the amylase performance in washing. Thus, the need exists for genetically engineered amylase enzymes that can function in the harsh environment of compositions used for cleaning, high temperatures, and still have an effective performance of removing starch stains in a washing application.

SUMMARY OF THE INVENTION

An amylase comprising an amino acid sequence that is at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171.

An amylase comprising an amino acid sequence that is at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, or SEQ ID NO:9.

An amylase comprising an amino acid sequence that is at least 95%, at least 96%, at least 97%, at least 98%, at least 98.5%, at least 99%, at least 99.5%, or 100% identical to the full length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, or SEQ ID NO:21.

An amylase comprising an amino acid sequence that is at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, or SEQ ID NO:43.

An amylase comprising an amino acid sequence that is at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, or SEQ ID NO:71.

An amylase comprising an amino acid sequence that is at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, or SEQ ID NO:91.

An amylase comprising an amino acid sequence that is at least 99% or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, or SEQ ID NO: 99.

An amylase comprising an amino acid sequence that is 99.5% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171.

An amylase comprising an amino acid sequence that is 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171.

In a preferred embodiment, the amylase comprises an amino acid sequence that is at least 94%, at least 95%, at least 96%, at least 97%, at least 98%, at least 98.5%, at least 99%, at least 99.5%, or 100% identical to the full-length amino acid sequence of: SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171.

In a further preferred embodiment, the amylase comprises an amino acid sequence that is at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:11, SEQ ID NO:15, SEQ ID NO:146, SEQ ID NO:148, SEQ ID NO: 152, SEQ ID NO: 154; SEQ ID NO: 170, or SEQ ID NO:171.

In a another preferred embodiment, the amylase comprises an amino acid sequence that is at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:15, SEQ ID NO:146, SEQ ID NO:148, SEQ ID NO: 152, SEQ ID NO: 154, SEQ ID NO: 170, or SEQ ID NO:171.

In a another preferred embodiment, the amylase comprises an amino acid sequence that is at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:15, SEQ ID NO:146, SEQ ID NO:148, SEQ ID NO: 152, SEQ ID NO: 170, or SEQ ID NO:171.

In another preferred embodiment, the amylase comprises an amino acid sequence that is at least 94%, at least 95%, at least 96%, at least 97%, at least 98%, at least 98.5%, at least 99%, at least 99.5%, or 100% identical to the full-length amino acid sequence of: SEQ ID NO:11.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, and comprising a deletion of one or more, preferably two or three, most preferred two amino acid residues, at amino acid positions 180-183, preferably 180-182, according to the numbering of SEQ ID NO: 133.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, and comprising a deletion of one or more, preferably two or three, most preferred two amino acid residues, at amino acid positions 180-183, preferably 180-182, according to the numbering of SEQ ID NO: 133.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:11, SEQ ID NO:15, SEQ ID NO:146, SEQ ID NO:148, SEQ ID NO: 152, SEQ ID NO: 154; SEQ ID NO: 170, or SEQ ID NO:171, and comprising a deletion of one or more, preferably two or three, most preferred two amino acid residues, at amino acid positions 180-183, preferably 180-182, according to the numbering of SEQ ID NO: 133.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, and comprising at least one, at least two, or at least three, most preferred two, deletions of amino acid residues selected from the group consisting of R180, S181, T182 and G183, preferably selected from the group consisting of R180, S181, and T182, according to the numbering of SEQ ID NO: 133.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, and comprising at least one, at least two, or at least three, most preferred two, deletions of amino acid residues selected from the group consisting of R180, S181, T182 and G183, preferably selected from the group consisting of R180, S181, and T182, according to the numbering of SEQ ID NO: 133.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:11, SEQ ID NO:15, SEQ ID NO:146, SEQ ID NO:148, SEQ ID NO: 152, SEQ ID NO: 154; SEQ ID NO: 170, or SEQ ID NO:171, and comprising at least one, at least two, or at least three, most preferred two, deletions of amino acid residues selected from the group consisting of R180, S181, T182 and G183, preferably selected from the group consisting of R180, S181, and T182, according to the numbering of SEQ ID NO: 133.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, and at least one polypeptide fragment selected from each of the following regions: Region 1, Region 2, Region 3, and Region 4. Herein, region 1 corresponds to the region of the amylase amino acid sequence defined by amino acid residues 1-76 according to the numbering of SEQ ID NO: 133; region 2 corresponds to the region of the amylase amino acid sequence defined by amino acid residues 77-210 according to the numbering of SEQ ID NO: 133; region 3 corresponds to the region of the amylase amino acid sequence defined by amino acid residues 211-302 according to the numbering of SEQ ID NO: 133, and region 4 corresponds to the region of the amylase amino acid sequence defined by amino acid residues 303-484 according to the numbering of SEQ ID NO: 133.

An amylase comprising at least one fragment of SEQ ID NO:101 and at least one fragment of SEQ ID NO:131, wherein the amino acid sequence of the at least one fragment of SEQ ID NO:101 differs from the corresponding fragment in SEQ ID NO:131 and wherein the amino acid sequence of the at least one fragment of SEQ ID NO:131 differs from the corresponding fragment in SEQ ID NO:101 and wherein the amylase comprises an amino acid sequence that is at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full length amino acid sequence of: SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, or SEQ ID NO:130.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, and at least one polypeptide fragment selected from each of the following regions: Region 1, Region 2, Region 3, and Region 4; wherein the polypeptide fragment from Region 1 is an amino acid sequence having at least 75% identical, 76% identical, at least 77% identical, at least 78% identical, at least 79% identical, at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to an amino acid sequence selected from: SEQ ID NO:103, and SEQ ID NO:104.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, and at least one polypeptide fragment selected from each of the following regions: Region 1, Region 2, Region 3, and Region 4; wherein the polypeptide fragment from Region 2 is an amino acid sequence having at least 75% identical, 76% identical, at least 77% identical, at least 78% identical, at least 79% identical, at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to an amino acid sequence selected from: SEQ ID NO:105, SEQ ID NO:106, SEQ ID NO:107, SEQ ID NO:108, SEQ ID NO:109, SEQ ID NO:110, SEQ ID NO:111, and SEQ ID NO:112.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, and at least one polypeptide fragment selected from each of the following regions: Region 1, Region 2, Region 3, and Region 4; wherein the polypeptide fragment from Region 3 is an amino acid sequence having at least 75% identical, 76% identical, at least 77% identical, at least 78% identical, at least 79% identical, at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to an amino acid sequence selected from: SEQ ID NO:113, SEQ ID NO:114, SEQ ID NO:115, SEQ ID NO:116, SEQ ID NO:117, SEQ ID NO:118, SEQ ID NO:119, and SEQ ID NO:120.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, and at least one polypeptide fragment selected from each of the following regions: Region 1, Region 2, Region 3, and Region 4; wherein the polypeptide fragment from Region 4 is an amino acid sequence is at least 75% identical, 76% identical, at least 77% identical, at least 78% identical, at least 79% identical, at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to an amino acid sequence selected from: SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, and SEQ ID NO:130.

An amylase comprising one or more amino acid residue insertions, deletions, substitutions, or any combinations thereof to the amino acid sequence of: SEQ ID NO: 1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171.

An amylase comprising one or more amino acid residue substitution to the amino acid sequence of: SEQ ID NO: 1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171.

An amylase wherein the amino acid sequence is encoded by a polynucleotide having a nucleic acid sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full length polynucleotide sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:68, SEQ ID NO:70, SEQ ID NO:72, SEQ ID NO:74, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, or SEQ ID NO:169.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the amylase has an increase in expression; activity; thermostability; stability; performance in laundry; or any combination thereof.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the increase in expression is from 1.01 to 1.27.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the increase in enzyme activity is from 12% to 121%.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the increase in enzyme activity is from 50% to 121%.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171; wherein the increase in thermostability is after a heat challenge at a temperature from 75 degrees C. to 95 degrees C.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the increase in thermostability is after a heat challenge at a temperature of: 80 degrees C., 81 degrees C., 82 degrees C., 83 degrees C., 84 degrees C., 85 degrees C., 86 degrees C., 87 degrees C., 88 degrees C., 89 degrees C., or 90 degrees C.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the increase in thermostability is after a heat challenge at a temperature of: 80 degrees C.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the increase in thermostability is after a heat challenge at a temperature of: 90 degrees C.

Preferably, the present invention is directed to an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171; wherein the amylase has increased stability, preferably in a laundry detergent.

Preferably, the present invention is directed to an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO: 134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171; wherein the amylase has increased stability, preferably in a laundry detergent.

Preferably, the present invention is directed to an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:11, SEQ ID NO:15, SEQ ID NO:146, SEQ ID NO:148, SEQ ID NO: 152, SEQ ID NO: 154; SEQ ID NO: 170, or SEQ ID NO:171; wherein the amylase has increased stability, preferably in a laundry detergent.

Preferably, the present invention is directed to an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:15, SEQ ID NO:146, SEQ ID NO:148, SEQ ID NO: 152, SEQ ID NO: 170, or SEQ ID NO:171; wherein the amylase has increased stability, preferably in a laundry detergent.

Preferably, the present invention is directed to an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:15, SEQ ID NO:148, SEQ ID NO: 170, or SEQ ID NO:171; wherein the amylase has increased stability, preferably in a laundry detergent.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171; wherein the increase in stability is from 0.8% to 70%.

Preferably, an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of SEQ ID NO: 134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171; wherein the increase in stability is from 0.8% to 70%.

Preferably, an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of SEQ ID NO:1, SEQ ID NO:11, SEQ ID NO:15, SEQ ID NO:146, SEQ ID NO:148, SEQ ID NO: 152, SEQ ID NO: 154; SEQ ID NO: 170, or SEQ ID NO:171; wherein the increase in stability is from 0.8% to 70%.

Preferably, an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of SEQ ID NO:1, SEQ ID NO:15, SEQ ID NO:146, SEQ ID NO:148, SEQ ID NO: 152, SEQ ID NO: 170, or SEQ ID NO:171; wherein the increase in stability is from 0.8% to 70%.

Preferably, an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of SEQ ID NO:1, SEQ ID NO:15, SEQ ID NO:148, SEQ ID NO: 170, or SEQ ID NO:171; wherein the increase in stability is from 0.8% to 70%.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the increase in stability is from 1.8% to 69.5%.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the increase in stability is from 1.7% to 49.3%.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the increase in stability is 0.8% to 21.6%.

In a preferred embodiment, the present invention is directed to an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the amylase has increased in performance in laundry.

In a preferred embodiment, the present invention is directed to an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO: 134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the amylase has increased in performance in laundry.

In a preferred embodiment, the present invention is directed to an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:11, SEQ ID NO:15, SEQ ID NO:146, SEQ ID NO:148, SEQ ID NO: 152, SEQ ID NO: 154; SEQ ID NO: 170, or SEQ ID NO:171, wherein the amylase has increased in performance in laundry.

In a preferred embodiment, the present invention is directed to an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:15, SEQ ID NO:146, SEQ ID NO:148, SEQ ID NO: 152, SEQ ID NO: 154; SEQ ID NO: 170, or SEQ ID NO:171, wherein the amylase has increased in performance in laundry.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the increase in performance in laundry is from 1.07 to 1.8 RGB.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO: 134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, wherein the increase in performance in laundry is from 1.07 to 1.8 RGB.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:11, SEQ ID NO:15, SEQ ID NO:146, SEQ ID NO:148, SEQ ID NO: 152, SEQ ID NO: 154; SEQ ID NO: 170, or SEQ ID NO:171, wherein the increase in performance in laundry is from 1.07 to 1.8 RGB.

An amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:15, SEQ ID NO:146, SEQ ID NO:148, SEQ ID NO: 152, SEQ ID NO: 154; SEQ ID NO: 170, or SEQ ID NO:171, wherein the increase in perfor-mance in laundry is from 1.07 to 1.8 RGB.

A compositions comprising an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171. In another embodiment, the composition further comprises a second enzyme selected from the group consisting of: a second amylase, a lipase, a protease, a cellulase, a laccase, a mannanase, a pectinase, a nuclease, and any combination thereof. In preferred embodiment, the composition further comprises a second enzyme and the second enzyme is a different amylase. In another preferred embodiment, the composition further comprises a second enzyme and the second enzyme is a protease.

A method of making the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171; comprising: providing a nucleic acid sequence comprising: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:68, SEQ ID NO:70, SEQ ID NO:72, SEQ ID NO:74, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, or SEQ ID NO:169; transforming the nucleic acid sequence into an expression host, cultivating the expression host to produce the amylase, and purifying the amylase.

The method of making the amylase wherein the expression host is selected from the group consisting of: a bacterial expression system, a yeast expression system, a fungal expression system, and a synthetic expression system.

The method of making the amylase wherein the bacterial expression system is selected from an *E. coli*, a *Bacillus*, a *Pseudomonas*, and a *Streptomyces*, wherein the yeast expression system is selected from a *Candida*, a *Pichia*, a *Saccharomyces*, a *Schizosaccharomyces* or, wherein the fungal expression system is selected from a *Penicillium*, an *Aspergillus*, a *Fusarium*, a *Myceliopthora*, a *Themothelomyces*, a *Rhizomucor*, a *Rhizopus*, a *Thermomyces*, and a *Trichoderma*.

A method of making the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171; wherein the expression host is a *Bacillus* host cell.

A method of preparing a dough or a baked product prepared from the dough, the method comprising adding the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, to the dough and baking it.

A method of use of the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, for processing starch, for cleaning or washing textiles, hard surfaces, or dishes, for making ethanol, for processing pulp or paper, or for feeding an animal.

A method of use of the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, for cleaning or washing textiles, hard surfaces, or dishes.

A method of use of the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171, for cleaning or washing textiles.

A method for making a hybrid amylase comprising: (a) providing an amylase having at least 80% identical to the full-length amino acid sequence of SEQ ID NO:101, SEQ ID NO:131, SEQ ID NO:132, or SEQ ID NO:133; (b) providing a polypeptide fragment having at least 75% sequence identity to an amino acid sequence selected from the amino acid sequence of: SEQ ID NO: 103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, and SEQ ID NO:130; (c) aligning the polypeptide fragments of (b) with the amino acid sequence of the amylase of (a) and identifying regions in the amylase of (a) that can be replaced by the fragments of (b); (d) substituting the regions in the amylase of (a) with the fragments of (b) to generate the hybrid amylase.

DETAILED DESCRIPTION OF THE INVENTION

An enzyme is a biological molecule (polypeptide) comprising a sequence of amino acid residues, wherein the enzyme can catalyze a reaction. Hence, enzymes are catalytically active proteins or polypeptides. Enzyme names are determined based on the recommendations of the Nomenclature Committee of the International Union of Biochemistry and Molecular Biology (IUBMB). Enzymes are defined by an EC (Enzyme Commission) number, recommended name, alternative names (if any), catalytic activity, and other factors. Enzymes herein may be identified by polypeptide sequences (also called amino acid sequences herein). The polypeptide sequence specifies the three-dimensional structure including the "active site" of an enzyme which in turn determines the catalytic activity of the same. Polypeptide sequences may be identified by a SEQ ID NO.

Enzymes are obtained from or derived from many different sources including: plants; animals; bacteria, archaea, fungi, yeast, environmental samples containing DNA that encodes an enzyme, or enzymes can be synthetic generated in a laboratory. For example, bacterial sources of enzymes include enzymes derived from *Bacillus, Streptomyces, E. coli* and *Pseudomonas*; fungal sources of enzymes include enzymes derived from *Aspergillus, Fusarium, Thermomyces* and *Trichoderma*; yeast sources of enzymes include enzymes derived from *Pichia*, and *Saccharomyces*.

Different classes of enzymes are known to be useful in detergents and cleaning products including: lipase, amylase, protease, cellulase, mannanase, pectate lyase, and nuclease; however, there is a need in the industry to provide an amylase that has more activity, temperature profile, pH profile, has improved performance (stain removal), stability in presence of protease, or a combination thereof. The amylase enzymes of the invention address the industrial needs.

The World Intellectual Property Office (WIPO) Standard ST.25 (1998) provides that the amino acid residues should be represented in the sequence listing using the following three-letter symbols with the first letter as a capital. The table below provides an overview of the amino acid identifiers as well as the corresponding DNA codons that encode the amino acid using the standard genetic standard. The DNA codons that encode amino acid residues can be different depending organism that is used and slightly different tables for translation of the genetic code may apply. A compilation of such non-standard code translation tables is maintained at the NCBI.

A "parent" polypeptide amino acid sequence is the starting sequence for introduction of mutations (e.g. by introducing one or more (fragments) amino acid substitutions, insertions, deletions, or a combination thereof) to the sequence, resulting in "variants" of the parent polypeptide amino acid sequences. A parent includes: A wild-type polypeptide amino acid sequence or synthetically generated polypeptide amino acid sequence that is used as starting sequence for introduction of (further) changes.

A "variant polypeptide" refers to an enzyme that differs from its parent in its amino acid sequence. The differences between the parent polypeptide and variant polypeptide can be one single amino acid residue, or more than one amino acid residue. The more than one amino acid residue and be consecutive amino acid residues or non-consecutive amino acid residues. The consecutive amino acid residues can be four consecutive amino acid residues; five consecutive amino acid residues; eight consecutive amino acid residues; nine consecutive amino acid residues; eleven consecutive amino acid residues; thirteen consecutive amino acid residues; or fourteen consecutive amino acid residues. While the definition below describes variants in the context of amino acid changes, nucleic acids may be similarly modified, e.g. by substitutions.

A "mature polypeptide" means an enzyme in its final form including any post-translational modifications, glycosylation, phosphorylation, truncation, N-terminal modifications, C-terminal modifications, signal sequence deletion. A mature polypeptide can vary depending upon the expression system, vector, promoter, and/or production process.

A "synthetic" or "artificial" compound is produced by in vitro chemical or enzymatic synthesis.

The term "non-naturally occurring" refers to a (poly) nucleotide, amino acid, (poly)peptide, enzyme, protein, cell, organism, or other material that is not present in its original naturally occurring environment or source. Preferably, the amylase of the present invention is a non-naturally occurring amylase.

Variant polynucleotide and variant polypeptide sequences may be defined by their sequence identity when compared to a parent sequence. Sequence identity usually is provided as "% sequence identity" or "% identity". For calculation of sequence identities, in a first step a sequence alignment is produced. According to this invention, a pairwise global alignment is produced, meaning that two sequences are aligned over their complete length, which is usually produced by using a mathematical approach, called alignment algorithm.

According to the invention, the alignment is generated by using the algorithm of Needleman and Wunsch (J. Mol. Biol. (1979) 48, p. 443-453). Preferably, the program "NEEDLE" (The European Molecular Biology Open Software Suite (EMBOSS)) is used for the purposes of the current invention, with using the programs default parameter (polynucleotides: gap open=10.0, gap extend=0.5 and matrix=EDNAFULL; polypeptides: gap open=10.0, gap extend=0.5 and matrix=EBLOSUM62).

After aligning two sequences, in a second step, an identity value is determined from the alignment produced.

For this purpose, the %-identity is calculated by dividing the number of identical residues by the length of the alignment region which is showing the respective sequence of the present invention over its complete length multiplied with 100: %–identity=(identical residues/length of the alignment region which is showing the respective sequence of the present invention over its complete length)*100.

For calculating the percent identity of two nucleic acid sequences the same applies as for the calculation of percent identity of two amino acid sequences with some specifications. For nucleic acid sequences encoding for a protein the pairwise alignment shall be made over the complete length of the coding region of the sequence of this invention from start to stop codon excluding introns. Introns present in the other sequence, to which the sequence of this invention is compared, may also be removed for the pairwise alignment. Percent identity is then calculated by %-identity=(identical residues/length of the alignment region which is showing the sequence of the invention from start to stop codon excluding introns over their complete length)*100. After aligning two sequences, in a second step, an identity value is determined from the alignment produced.

Moreover, the preferred alignment program for nucleic acid sequences implementing the Needleman and Wunsch algorithm (J. Mol. Biol. (1979) 48, p. 443-453) is "NEEDLE" (The European Molecular Biology Open Software Suite (EMBOSS)) with the programs default parameters (gapopen=10.0, gapextend=0.5 and matrix=EDNAFULL).

Sequences, having identical or similar regions with a sequence of this invention, and which shall be compared with a sequence of this invention to determine % identity, can easily be identified by various ways that are within the skill in the art, for instance, using publicly available computer methods and programs such as BLAST, BLAST-2, available for example at NCBI.

Variant polypeptides may be defined by their sequence similarity when compared to a parent sequence. Sequence similarity usually is provided as "% sequence similarity" or "%-similarity". % sequence similarity takes into account that defined sets of amino acids share similar properties, e.g. by their size, by their hydrophobicity, by their charge, or by other characteristics. Herein, the exchange of one amino acid with a similar amino acid may be called "conservative mutation". Similar amino acids according to the invention are defined as follows, which shall also apply for determination of %-similarity according to this invention, which is also in accordance with the BLOSUM62 matrix as for example used by program "NEEDLE", which is one of the most used amino acids similarity matrix for database searching and sequence alignments:

Amino acid A is similar to amino acids S
Amino acid D is similar to amino acids E; N
Amino acid E is similar to amino acids D; K; Q
Amino acid F is similar to amino acids W; Y
Amino acid H is similar to amino acids N; Y
Amino acid I is similar to amino acids L; M; V
Amino acid K is similar to amino acids E; Q; R
Amino acid L is similar to amino acids I; M; V
Amino acid M is similar to amino acids I; L; V
Amino acid N is similar to amino acids D; H; S
Amino acid Q is similar to amino acids E; K; R
Amino acid R is similar to amino acids K; Q
Amino acid S is similar to amino acids A; N; T
Amino acid T is similar to amino acids S
Amino acid V is similar to amino acids I; L; M
Amino acid W is similar to amino acids F; Y
Amino acid Y is similar to amino acids F; H; W Conservative amino acid substitutions may occur over the full length of the sequence of a polypeptide sequence of a functional protein such as an enzyme. In one embodiment, such mutations are not pertaining the functional domains of an enzyme. In one embodiment, conservative mutations are not pertaining the catalytic centers of an enzyme.

For calculation of sequence similarity, in a first step a sequence alignment is produced as described above. After aligning two sequences, in a second step, a similarity value is determined from the alignment produced.

For this purpose, the %-similarity is calculated by dividing the number of identical residues plus the number of similar residues by the length of the alignment region which is showing the sequence of the invention over its complete length multiplied with 100: %-similarity=[(identical residues+similar residues)/length of the alignment region which is showing the sequence of the invention over its complete length]*100.

The invention relates to a polypeptide having amylase activity comprising an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to any one of the full length amino acid sequence of: SEQ ID NO:1, SEQ ID NO:3, SEQ ID NO:5, SEQ ID NO:7, SEQ ID NO:9, SEQ ID NO:11, SEQ ID NO:12, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171.

The invention relates to a polypeptide having amylase activity comprising an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to any one of the full length amino acid sequence of SEQ ID NO: 134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:166, SEQ ID NO:168, SEQ ID NO:170, or SEQ ID NO:171.

The invention relates to a polypeptide having amylase activity comprising an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to any one of the full length amino acid sequence of SEQ ID NO:1, SEQ ID NO:11, SEQ ID NO:15, SEQ ID NO:146, SEQ ID NO:148, SEQ ID NO: 152, SEQ ID NO: 154; SEQ ID NO: 170, or SEQ ID NO:171.

The invention relates to a polypeptide having amylase activity comprising an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to any one of the full length amino acid sequence of SEQ ID NO:11.

The invention relates to a polypeptide having amylase activity comprising an amino acid sequence that is at least 75% identical, 76% identical, at least 77% identical, at least 78% identical, at least 79% identical, at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to any of the full length amino acid sequence of SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, or SEQ ID NO:130.

The invention further relates to a polynucleotide encoding a variant polypeptide of the invention. The terms "poly-nucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length. A "gene" is a DNA segment carrying a certain genetic information.

A "parent" polynucleotide acid sequence is the starting sequence for introduction of mutations to the sequence, resulting in "variants" of said parent polynucleotide sequence. A "variant polynucleotide" refers to a polynucle-otide that encodes an enzyme and the variant polynucleotide differs from its parent polynucleotide in its nucleic acid sequence.

The polynucleotide of the invention in one aspect has a nucleic acid sequence which is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical when compared to any one of the full length polynucleotide sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:68, SEQ ID NO:70, SEQ ID NO:72, SEQ ID NO:74, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, or SEQ ID NO:169. The poly-nucleotide of the invention in one aspect has a nucleic acid sequence which is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical when compared to any one of the full length polynucleotide sequence of SEQ ID NO:2, SEQ ID NO: 12, SEQ ID NO:16, SEQ ID NO:147, SEQ ID NO:149, SEQ ID NO: 155, or SEQ ID NO: 153. In one embodiment, the invention relates to a polypeptide having amylase activity which is encoded by a polynucleotide having a nucleic acid sequence at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to any one of the full length polynucleotide sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:68, SEQ ID NO:70, SEQ ID NO:72, SEQ ID NO:74, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:167, or SEQ ID NO:169.

Preferably, the polynucleotide is a codon-optimized poly-nucleotide for improving expression in a specific host cell.

"Substitutions" are described by providing the original amino acid followed by the number of the position within the amino acid sequence, followed by the substituted amino acid. A specific amino acid residue may be substituted with any of the 19 amino acid residues different from the original one. For example, the substitution of histidine at position 120 with alanine is designated as "His120Ala" or "H120A". Alternative substitutions at an amino acid position are indicated as follows "His120Ala,Leu" or "H120A,L". It is understood herein that instead of the indicated specific substitutions alternative substitutions using conservative amino acid alternatives can be used.

Amino acid deletions are described by providing the original amino acid of the parent enzyme followed by the number of the position within the amino acid sequence, followed by *. Accordingly, the deletion of glycine at position 150 is designated as "Gly150*" or G150*". Alter-natively, deletions are indicated by e.g. "deletion of D183 and G184".

Preferably, the amino acid sequence of the amylase of the present invention comprises a deletion of one or more, preferably two or three, most preferred two amino acid residues, at amino acid positions 180-183, preferably 180-182, according to the numbering of SEQ ID NO: 133. Preferably, the amylase variants of the invention comprise at least one, at least two, or at least three, most preferred two, deletions of amino acid residues selected from the group consisting of R180, S181, T182 and G183, preferably selected from the group consisting of R180, S181, and T182, SEQ according to the numbering of SEQ ID NO: 133. These deletions provide improved stability to the amylases.

Amino acid insertions are described by providing the original amino acid of the parent enzyme followed by the number of the position within the amino acid sequence, followed by the original amino acid and the additional amino acid. For example, an insertion at position 180 of lysine next to glycine is designated as "Gly180GlyLys" or "G180GK". When more than one amino acid residue is inserted, such as e.g. a Lys and Ala after Gly180 this may be indicated as: Gly180GlyLysAla or G195GKA.

In cases where a substitution and an insertion occur at the same position, this may be indicated as S99SD+S99A or in short S99AD.

The one or more amino acid substitution of the variant polypeptides can be one or more conservative amino acid substitution. A "conservative amino acid substitution" or "related amino acid" means replacement of one amino acid residue in an amino acid sequence with a different amino acid residue having a similar property at the same position compared to the parent amino acid sequence. Some examples of a conservative amino acid substitution include but are not limited to replacing a positively charged amino acid residue with a different positively charged amino acid residue; replacing a polar amino acid residue with a different polar amino acid residue; replacing a non-polar amino acid residue with a different non-polar amino acid residue, replacing a basic amino acid residue with a different basic amino acid residue, or replacing an aromatic amino acid residue with a different aromatic amino acid residue.

"Enzymatic activity" means at least one catalytic effect exerted by an enzyme. Enzymatic activity is expressed as units per milligram of enzyme (specific activity) or molecules of substrate transformed per minute per molecule of enzyme (molecular activity). Enzymatic activity can be specified by the enzymes actual function, e.g. proteases exerting proteolytic activity by catalyzing hydrolytic cleavage of peptide bonds, lipases exerting lipolytic activity by hydrolytic cleavage of ester bonds, amylases activity involves (endo)hydrolysis of glucosidic linkages in polysaccharides, etc.

Enzymatic activity may change during storage or operational use of the enzyme. The term "enzyme stability" relates to the retention of enzymatic activity as a function of time during storage or operation. The term "storage" herein means to indicate the fact of products or compositions or formulations being stored from the time of being manufactured to the point in time of being used in final application. Retention of enzymatic activity as a function of time during storage may be called "storage stability" herein.

To determine and quantify changes in catalytic activity of enzymes stored or used under certain conditions over time, the "initial enzymatic activity" is measured under defined conditions at time zero (100%) and at a certain point in time later (x %). By comparison of the values measured, a potential loss of enzymatic activity can be determined in its extent. The extent of enzymatic activity loss determines an enzymes stability or non-stability.

Parameters influencing the enzymatic activity of an enzyme and/or storage stability and/or operational stability are for example pH, temperature, chelators, and presence of oxidative substances.

A variant polypeptide may be active over a broad pH at any single point within the range from about pH 4.0 to about pH 12.0. The variant polypeptides enzyme may be active over a range of pH 5.0 to pH 11.0, pH 6.0 to pH 10.0, and pH 7.0 to pH 9.0. In another embodiment, the variant polypeptides enzyme may be active over a pH 7.1 to pH 8.9, pH 7.2 to pH 8.8, pH 7.3 to pH 8.7, pH 7.4 to pH 8.6, pH 7.5 to pH 8.5. The variant polypeptides may be active at pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6 pH 8.7, pH 8.8 pH 8.9, pH 9.0, pH 9.1, pH 9.2, pH 9.3, pH 9.4, pH 9.5, pH 9.6, pH 9.7, pH 9.8, pH 9.9, pH 10.0, pH 10.1, pH 10.2, pH 10.3, pH 10.4, pH 10.5, pH 10.6, pH 10.7, pH 10.8, pH 10.9, pH 11.0, pH 11.1, pH 11.2, pH 11.3, pH 11.4, pH 11.5, pH 11.6, pH 11.7, pH 11.8, pH 11.9, pH 12.0, pH 12.1, pH 12.2, pH 12.3, pH 12.4, and pH 12.5, pH 12.6, pH 12.7, pH 12.8, pH 12.9, or higher.

A "pH stability", refers to the ability of an enzyme to exert enzymatic activity at a specific pH range.

The variant polypeptides may be active over a broad temperature, wherein the temperature is any point in the range from about 10° C. to about 95° C. The variant polypeptides may be active at a temperature range from 10° C. to 55° C., 10° C. to 50° C., 10° C. to 45° C., 10° C. to 40° C., 10° C. to 35° C., 10° C. to 30° C., or 10° C. to 25° C. The variant polypeptides may be active at a temperature range from 20° C. to 55° C., 20° C. to 50° C., 20° C. to 45° C., 20° C. to 40° C., 20° C. to 35° C., 20° C. to 30° C., or 20° C. to 25° C. The variant polypeptides are active at a temperature of at least 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., or higher temperatures.

The terms "thermal stability" and "thermostability" refer to the ability of a protein to exert catalytic activity at a specific temperature range. Enzymes thermostability may be characterized by what is known as the T50 value (also called half-life, see above). The T50 indicates the temperature at which 50% residual enzymatic activity is still present after thermal inactivation for a certain time when compared with a reference sample which has not undergone thermal treatment.

In one embodiment, the variant polypeptides improve the thermostability compared to the parent molecule. In another embodiment the variant polypeptides improve the thermostability by 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., or more degrees C. when compared to the parent polypeptide. In another embodiment, the thermostability increase is measured at a temperature between 70° C. and 100° C. The thermostability increase can be measured at 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., and/or 100° C. In another embodiment, the thermostability increase is measured at a temperature of 80° C. In another embodiment, the thermostability increase is measured a temperature of 90° C.

In one embodiment, the variant polypeptide is a fragment of the full-length amino acid sequence and the fragment has amylase activity.

A "Fragment", or "subsequence" as used herein are a portion of a polynucleotide or an amino acid sequence.

The term "functional fragment" refers to any nucleic acid or amino acid sequence which comprises merely a part of the full-length amino acid sequence, respectively, but still has the same or similar activity and/or function. Preferably, the functional fragment is at least 75% identical, at least 76% identical, at least 77% identical, at least 78% identical, at least 79% identical, at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, or at least 99.5% identical to the full length amino acid sequence original sequence. The functional fragment comprises contiguous nucleic acids or amino acids compared to the original nucleic acid or original amino acid sequence, respectively.

The polypeptide variants can be a hybrid of more than one amylase enzymes. In one embodiment, the polypeptide variant can be a hybrid of the polypeptide variant and at least one additional enzyme selected from the group consisting of: a second amylase, a lipase, a protease, a cellulase, a laccase, a pectinase, and a nuclease, wherein the hybrid has amylase activity and enzymatic activity of the second enzyme.

In one embodiment, the present invention refers to a polypeptide comprising a hybrid of at least one polypeptide as described herein and a second polypeptide having an activity selected from the group consisting of amylase activity, wherein the hybrid also has amylase activity.

In on embodiment the variant polypeptide comprises a hybrid of at least one variant polypeptide as described herein, and a second polypeptide having amylase activity, wherein the hybrid has amylase activity.

A "hybrid" or "chimeric" or "fusion protein" means that a fragment of the amino acid sequence of a first enzyme is combined with a fragment of the amino acid sequence of a second enzyme to form a hybrid enzyme wherein the hybrid has an enzyme activity.

The hybrid enzymes can be engineered with fragments from amino acid sequences of more than two enzymes. The domain of an amylase of this invention may be combined with a domain of a commercially available amylase such as: Duramyl™, Termamyl™, Termamyl SC™, Termamyl Ultra™, Fungamyl™, Stainzyme™, Stainzyme Plus™, Natalase™, Liquozyme X, Supramyl™ Amplify™, Amplify Prime™ and BAN™ (from Novozymes A/S), and Rapidase™, Purastar™ Purastar OxAm™ Powerase™, Effectenz™ (M100 from DuPont), Preferenz™ (S1000, S110 and F1000; from DuPont), PrimaGreen™ (ALL; DuPont), Optisize™ (DuPont) and Kam™ (Kao) and Kemzyme™ (Biozym), to form a hybrid enzyme and the hybrid has amylase activity.

In another aspect the present invention refers to a composition comprising the polypeptide described herein. A composition may comprise combinations of the polypeptides with another enzyme. The combination of enzymes can be of the same class, for example a composition comprising a first amylase and a second amylase. Combinations of enzymes can be from a different class of enzymes, for example, a composition comprising a lipase and an amylase. Combinations of enzymes can be compositions comprising at least one amylase of the invention and one or more second enzymes. In one embodiment, the composition comprises one second enzyme, two second enzymes, three second enzymes, four second enzymes, or more than four second enzymes. In an embodiment, the second enzyme is selected from the group consisting of: a second amylase, a lipase, a protease, a cellulase, a laccase, a pectinase, and a nuclease, or any combination thereof.

Additional enzymes suitable for the hybrid or the composition of the present invention are further described below. In one embodiment, suitable enzymes include enzyme variants having enzymatic activity which are at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% identical when compared to the full length polypeptide sequence of the parent enzyme as disclosed below.

Amylase

Alpha-amylase (E.C. 3.2.1.1) enzymes may perform endohydrolysis of (1->4)-alpha-D-glucosidic linkages in polysaccharides containing three or more (1->4)-alpha-linked D-glucose units. Amylase enzymes act on starch, glycogen and related polysaccharides and oligosaccharides in a random manner; reducing groups are liberated in the alpha-configuration. Other examples of amylase enzymes include: Beta-amylase (E.C. 3.2.1.2), Glucan 1,4-alpha-maltotetraohydrolase (E.C. 3.2.1.60), Isoamylase (E.C. 3.2.1.68), Glucan 1,4-alpha-maltohexaosidase (E.C. 3.2.1.98), and Glucan 1,4-alpha-maltohydrolase (E.C. 3.2.1.133).

Many amylase enzymes have been described in patents and published patent applications including, but not limited to: WO 2002/068589, WO 2002/068597, WO 2003/083054, WO 2004/091544, and WO 2008/080093.

Amylases are known to be derived from Bacillus licheniformis having SEQ ID NO:2 as described in WO 95/10603. Suitable variants are those which are at least 90% identical to SEQ ID NO: 2 as described in WO 95/10603 and/or comprising one or more substitutions in the following positions: 15, 23, 105, 106, 124, 128, 133, 154, 156, 178, 179, 181, 188, 190, 197, 201, 202, 207, 208, 209, 211, 243, 264, 304, 305, 391, 408, and 444 which have amylolytic activity. Such variants are described in WO 94/02597, WO 94/018314, WO 97/043424 and SEQ ID NO:4 of WO 99/019467.

Amylases are known to be derived from B. stearothermophilus having SEQ ID NO:6 as described in WO 02/10355 or an amylase which is at least 90% identical thereto having amylolytic activity with optionally having a C-terminal truncation over the wildtype sequence. Suitable variants of SEQ ID NO:6 include those which is at least 90% identical thereto and/or further comprise a deletion in positions 181 and/or 182 and/or a substitution in position 193.

Amylases are known to be derived from Bacillus sp. 707 having SEQ ID NO:6 as disclosed in WO 99/19467 or an amylase which is at least 90% identical thereto having amylolytic activity. Amylases are known from Bacillus halmapalus having SEQ ID NO:2 or SEQ ID NO:7 as described in WO 96/23872, also described as SP-722, or an amylase which is at least 90% identical to one of the sequences which has amylolytic activity.

Amylases are known to be derived from Bacillus sp. DSM 12649 having SEQ ID NO:4 as disclosed in WO 00/22103 or an amylase which is at least 90% identical thereto having amylolytic activity.

Amylases are known from Bacillus strain TS-23 having SEQ ID NO:2 as disclosed in WO 2009/061380 or an amylase which is at least 90% identical thereto having amylolytic activity. Amylases are known from Cytophaga sp. having SEQ ID NO:1 as disclosed in WO 2013/184577 or an amylase which is at least 90% identical thereto having amylolytic activity.

Amylases are known from Bacillus megaterium DSM 90 having SEQ ID NO:1 as disclosed in WO 2010/104675 or an amylase which is at least 90% identical thereto having amylolytic activity.

Amylases are known having amino acids 1 to 485 of SEQ ID NO:2 as described in WO 00/60060 or amylases comprising an amino acid sequence which is at least 96% identical with amino acids 1 to 485 of SEQ ID NO:2 which have amylolytic activity.

Amylases are also known having SEQ ID NO: 12 as described in WO 2006/002643 or amylases having at least 80% identity thereto and have amylolytic activity. Suitable amylases include those having at least 80% identity compared to SEQ ID NO:12 and/or comprising the substitutions at positions Y295F and M202LITV and have amylolytic activity.

Amylases are also known having SEQ ID NO:6 as described in WO 2011/098531 or amylases having at least 80% identity thereto having amylolytic activity. Suitable amylases include those having at least 80% identity compared to SEQ ID NO:6 and/or comprising a substitution at one or more positions selected from the group consisting of 193 [G,A,S,T or M], 195 [F,W,Y,L,I or V], 197 [F,W,Y,L,I or V], 198 [Q or N], 200 [F,W,Y,L,I or V], 203 [F,W,Y,L,I or V], 206 [F,W,Y,N,L,I,V,H,Q,D or E], 210 [F,W,Y,L,I or V], 212 [F,W,Y,L,I or V], 213 [G,A,S,T or M] and 243 [F,W,Y, L,I or V] and have amylolytic activity.

Amylases are known having SEQ ID NO:1 as described in WO 2013/001078 or amylases having at least 85% identity thereto having amylolytic activity. Suitable amylases include those having at least 85% identity compared to SEQ ID NO:1 and/or comprising an alteration at two or more (several) positions corresponding to positions G304, W140, W189, D134, E260, F262, W284, W347, W439, W469, G476, and G477 and having amylolytic activity.

Amylases are known having SEQ ID NO:2 as described in WO 2013/001087 or amylases having at least 85% identity thereto and having amylolytic activity. Suitable amylases include those having at least 85% identity compared to SEQ ID NO:2 and/or comprising a deletion of positions 181+182, or 182+183, or 183+184 according to the numbering of SEQ ID NO: 2 as described in WO 2013/001087, which have amylolytic activity. Suitable amylases include those having at least 85% identity compared to SEQ ID NO:2 and/or comprising a deletion of positions 181+182, or 182+183, or 183+184 according to the numbering of SEQ ID NO: 2 as described in WO 2013/001087, which comprise one or two or more modifications in any of positions corresponding to W140, W159, W167, Q169, W189, E194, N260, F262, W284, F289, G304, G305, 8320, W347, W439, W469, G476 and G477 and have amylolytic activity.

Amylases also include hybrid α-amylase from above mentioned amylases as for example as described in WO 2006/066594.

Commercially available amylase enzymes include: Duramyl™, Termamyl™, Termamyl SC™, Termamyl Ultra™, Fungamyl™, Stainzyme™, Stainzyme Plus™, Natalase™, Liquozyme X, Supramyl™ Amplify™, Amplify Prime™ and BAN™ (from Novozymes A/S), and Rapidase™ Purastar™, Purastar OxAm™ Powerase™, Effectenz™ (M100 from DuPont), Preferenz™ (S1000, S110 and F1000; from DuPont), PrimaGreen™ (ALL; DuPont), Optisize™ (DuPont) and Kam™ (Kao) and Kemzyme™ (Biozym).

Lipase

"Lipases", "lipolytic enzyme", "lipid esterase", all refer to an enzyme of EC class 3.1.1 ("carboxylic ester hydrolase"). Lipases (E.C. 3.1.1.3, Triacylglycerol lipase) may hydrolyze triglycerides to more hydrophilic mono- and diglycerides, free fatty acids, and glycerol. Lipase enzymes usually includes also enzymes which are active on substrates different from triglycerides or cleave specific fatty acids, such as Phospholipase A (E.C. 3.1.1.4), Galactolipase (E.C. 3.1.1.26), cutinase (EC 3.1.1.74), and enzymes having sterol esterase activity (EC 3.1.1.13) and/or wax-ester hydrolase activity (EC 3.1.1.50).

Many lipase enzymes have been described in patents and published patent applications including, but not limited to: WO2000032758, WO2003/089620, WO2005/032496, WO2005/086900, WO200600976, WO2006/031699, WO2008/036863, WO2011/046812, and WO2014059360.

Lipases are used in detergent and cleaning products to remove grease, fat, oil, and dairy stains. Commercially available lipases include but are not limited to: Lipolase™, Lipex™, Lipolex™ and Lipoclean™ (Novozymes A/S), Lumafast (originally from Genencor) and Lipomax (Gist-Brocades/now DSM).

The methods for determining lipolytic activity are well-known in the literature (see e.g. Gupta et al. (2003), Biotechnol. Appl. Biochem. 37, p. 63-71). E.g. the lipase activity may be measured by ester bond hydrolysis in the substrate para-nitrophenyl palmitate (pNP-Palmitate, C:16) and releases pNP which is yellow and can be detected at 405 nm.

Protease

Enzymes having proteolytic activity are called "proteases" or "peptidases". Proteases are active proteins exerting "protease activity" or "proteolytic activity".

Proteases are members of class EC 3.4. Proteases include aminopeptidases (EC 3.4.11), dipeptidases (EC 3.4.13), dipeptidyl-peptidases and tripeptidyl-peptidases (EC 3.4.14), peptidyl-dipeptidases (EC 3.4.15), serine-type carboxypeptidases (EC 3.4.16), metallocarboxypeptidases (EC 3.4.17), cysteine-type carboxypeptidases (EC 3.4.18), omega peptidases (EC 3.4.19), serine endopeptidases (EC 3.4.21), cysteine endopeptidases (EC 3.4.22), aspartic endopeptidases (EC 3.4.23), metallo-endopeptidases (EC 3.4.24), threonine endopeptidases (EC 3.4.25), endopeptidases of unknown catalytic mechanism (EC 3.4.99).

Commercially available protease enzymes include but are not limited to Lavergy™ Pro (BASF); Alcalase®, Blaze®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect® Prime, Purafect MA®, Purafect Ox®, Purafect OxP®, Puramax®, Properase®, FN2®, FN3®, FN4®, Excellase®, Eraser®, Ultimase®, Opticlean®, Effectenz®, Preferenz® and Optimase® (Danisco/DuPont), Axapem™ (Gist-Brocases N.V.), Bacillus lentus Alkaline Protease, and KAP (Bacillus alkalophilus subtilisin) from Kao.

At least one protease may be selected from serine proteases (EC 3.4.21). Serine proteases or serine peptidases (EC 3.4.21) are characterized by having a serine in the catalytically active site, which forms a covalent adduct with the substrate during the catalytic reaction. A serine protease may be selected from the group consisting of chymotrypsin (e.g., EC 3.4.21.1), elastase (e.g., EC 3.4.21.36), elastase (e.g., EC 3.4.21.37 or EC 3.4.21.71), granzyme (e.g., EC 3.4.21.78 or EC 3.4.21.79), kallikrein (e.g., EC 3.4.21.34, EC 3.4.21.35, EC 3.4.21.118, or EC 3.4.21.119) plasmin (e.g., EC 3.4.21.7), trypsin (e.g., EC 3.4.21.4), thrombin (e.g., EC 3.4.21.5) and subtilisin (also known as subtilopeptidase, e.g., EC 3.4.21.62), the latter hereinafter also being referred to as "subtilisin".

Cellulase

"Cellulases", "cellulase enzymes" or "cellulolytic enzymes" are enzymes involved in hydrolysis of cellulose. Three major types of cellulases are known, namely endo-ss-1,4-glucanase (endo-1,4-P-D-glucan 4-glucanohydrolase, E.C. 3.2.1.4; hydrolyzing β-1,4-glucosidic bonds in cellulose), cellobiohydrolase (1,4-P-D-glucan cellobiohydrolase, EC 3.2.1.91), and ss-glucosidase (EC 3.2.1.21).

Cellulase enzymes have been described in patents and published patent applications including, but not limited to: WO1997/025417, WO1998/024799, WO2003/068910, WO2005/003319, and WO2009020459.

Commercially available cellulase enzymes include are Celluzyme™, Endolase™ Carezyme™, Cellusoft™, Renozyme™, Celluclean™ (from Novozymes A/S), Ecostone™, Biotouch™, Econase™, Ecopulp™ (from AB Enzymes Finland), Clazinase™, and Puradax HA™, Genencor detergent cellulase L, IndiAge™ Neutra (from Genencor International Inc./DuPont), Revitalenz™ (2000 from DuPont), Primafast™ (DuPont) and KAC-500™ (from Kao Corporation).

Cellulases according to the invention have "cellulolytic activity" or "cellulase activity". Assays for measurement of cellulolytic activity are known to those skilled in the art. For example, cellulolytic activity may be determined by cellulase hydrolyses carboxymethyl cellulose to reducing carbohydrates, the reducing ability of which is determined colorimetrically by means of the ferricyanide reaction, according to Hoffman, W. S., J. Biol. Chem. 120, 51 (1937).

Mannanase

Mannanase (E.C. 3.2.1.78) enzymes hydrolyze internal β-1,4 beta-D-mannosidic linkages in mannans, galactomannans and glucomannans. "Mannanase" may be an alkaline mannanase of Family 5 or 26. Mannanase are useful components of washing and/or cleaning formulations since mannanase remove part of hemicellulose containing stains. Insufficient removal of these types of stains may e.g. result in fabric graying. The major constituents of hemicellulose are hetero-1,4-D-xylans and herto-1,4-beta-mannans. Mannans are polysaccharides with a backbone of β-1,4-linked D-mannopyranosyl residues, which can contain galactose or acetyl substitutions and may have glucose residues in the backbone. Mannanase enzymes are known to be derived from wild-type from *Bacillus* or *Humicola*, particularly *B. agaradhaerens, B. licheniformis, B. halodurans, B. clausii*, or *H. insolens*. Suitable mannanases are described in WO 99/064619.

Commercially available mannanase enzymes include: Mannaway® (Novozymes AIS).

Pectate Lyase

Pectate lyase (E.C. 4.2.2.2) enzymes eliminative cleavage of (1->4)-alpha-D-galacturonan to give oligosaccharides with 4-deoxy-alpha-D-galact-4-enuronosyl groups at their non-reducing ends.

Pectate lyase enzymes have been described in patents and published patent applications including, but not limited to: WO2004/090099. Pectate lyase are known to be derived from *Bacillus*, particularly *B. licheniformis* or *B. agaradhaerens*, or a variant derived of any of these, e.g. as described in U.S. Pat. No. 6,124,127, WO 99/027083, WO 99/027084, WO 2002/006442, WO 2002/092741, WO 2003/095638.

Commercially available pectate lyase enzymes include: Xpect™, Pectawash™ and Pectaway™ (Novozymes A/S); PrimaGreen™, EcoScour (DuPont).

Nuclease

Nuclease (EC 3.1.21.1) also known as Deoxyribonuclease I, or DNase preforms endonucleolytic cleavage to 5'-phosphodinucleotide and 5'-phosphooligonucleotide end-products.

Nuclease enzymes have described in patents and published patent applications including, but not limited to: U.S. Pat. No. 3,451,935, GB1300596, DE10304331, WO2015155350, WO2015155351, WO2015166075, WO2015181287, and WO2015181286.

In one aspect of the invention, at least one amylase variant of the invention is provided in combination with at least one protease. In one embodiment, an amylase variant of the invention is stable in the presence of at least one protease. In one embodiment, an amylase variant of the invention has increased protease stability when compared to the respective amylase parent. In one embodiment, at least one protease is selected from subtilisin 309 as disclosed as sequence a) in Table I of WO 89/06279 or a variant thereof which is at least 80% identical thereto and has proteolytic activity. In one embodiment, an amylase variant of the invention has increased protease stability in the presence of said subtilisin 309 or a variant thereof which is at least 80% identical thereto when compared to the amylase according to SEQ ID NO: 101.

The protease may itself be stabilized by a protease stabilizer or the protease may be non-stabilized. In one embodiment, an amylase variant of the invention has increased protease stability in the presence of a non-stabilized subtilisin 309 or a non-stabilized variant thereof which is at least 80% identical thereto, when compared to the amylase according to SEQ ID NO: 101.

Method of Making

In another embodiment, the present invention refers to a method of making the variant polypeptide as described herein, comprising: providing a nucleic acid sequence encoding the polypeptide described herein, transforming the nucleic acid sequence into a host cell, cultivating the host cell to produce the variant polypeptide, and optionally purifying the variant polypeptide from the host cell.

A polynucleotide encoding a polypeptide may be "expressed". The term "expression" or "gene expression" means the transcription of a specific gene or specific genes or specific nucleic acid construct. The term "expression" or "gene expression" means the transcription of a gene or genes or genetic construct into structural RNA (e.g., rRNA, tRNA) or mRNA with or without subsequent translation of the latter into a protein. The process includes transcription of DNA and processing of the resulting mRNA product.

Industrial production of enzymes usually is done by using expression systems. "Expression system" may mean a host microorganism, expression hosts, host cell, production organism, or production strain and each of these terms can be used interchangeably. In one embodiment, the expression host is selected from the group consisting of: a bacterial expression system, a yeast expression system, a fungal expression system, and a synthetic expression system. The expression host may be a wildtype cell or a recombinant cell. "Wild-type cells" herein means cells prior to a certain modification. The term "recombinant cell" (also called "genetically modified cell" herein) refers to a cell which has been genetically altered, modified or engineered such it that exhibits an altered, modified or different genotype as compared to the wild-type cell which it was derived from. The "recombinant cell" may comprise an exogenous polynucleotide encoding a certain protein or enzyme and therefore may express said protein or enzyme.

Thus, in one embodiment, the invention is directed to a genetic construct comprising a polynucleotide encoding the amylase as described herein.

In one embodiment, the invention is directed to a host cell comprising a polynucleotide encoding the amylase as described herein.

In yet another embodiment, the present invention is directed to a method of expressing a polynucleotide, comprising the steps of (a) providing a host cell comprising a heterologous nucleic acid construct comprising a polynucleotide encoding the amylase described herein by introducing the nucleic acid construct comprising the polynucleotide encoding the amylase as described herein into the host cell;

(b) cultivating the recombinant host cell of step (a) under conditions conductive for the expression of the polynucleotide; and (c) optionally, recovering a protein of interest encoded by the polynucleotide.

Examples of expression systems include but are not limited to: *Aspergillus niger, Aspergillus oryzae, Hansenula polymorpha, Thermomyces lanuginosus, Fusarium oxysporum, Fusarium heterosporum, Escherichia coli, Bacillus*, preferably *Bacillus subtilis*, or *Bacillus licheniformis, Pseudomonas*, preferably *Pseudomonas fluorescens, Pichia pastoris* (also known as *Komagataella phaffin, Myceliopthora thermophile* (C1), *Themothelomyces thermophila, Schizosaccharomyces pombe, Trichoderma*, preferably *Trichoderma reesei* and *Saccharomyces*, preferably *Saccharomyces cerevisiae*. The variant polypeptides may be produced using the expression system listed above.

In one embodiment, the bacterial expression system is selected from an *E. coli*, a *Bacillus*, a *Pseudomonas*, and a *Streptomyces*. In one embodiment, the yeast expression system is selected from a *Candida*, a *Pichia*, a *Saccharomyces*, and/or a *Schizosaccharomyces*. In one embodiment, the fungal expression system is selected from a *Penicillium*, an *Aspergillus*, a *Fusarium*, a *Myceliopthora*, a *Rhizomucor*, a *Rhizopus*, a *Thermomyces*, and a *Trichoderma*.

The term "heterologous" (or exogenous or foreign or recombinant) in the context of polynucleotides and polypeptides is defined herein as:

(a) not native to the host cell;

(b) native to the host cell but structural modifications, e.g., deletions, substitutions, and/or insertions, are included as a result of manipulation of the DNA of the host cell by recombinant DNA techniques to alter the native sequence; or (c) native to the host cell but expression is quantitatively altered, or expression is directed from a genomic location different from the native host cell as a result of manipulation of the DNA of the host cell by recombinant DNA techniques, e.g., a stronger promoter.

With respect to two or more polynucleotide sequences or two or more amino acid sequences, the term "heterologous" is used to characterize that the two or more polynucleotide sequences or two or more amino acid sequences do not occur naturally in the specific combination with each other.

"Genetic Construct" or "expression cassette" as used herein, is a DNA molecule composed of at least one sequence of interest to be expressed, operably linked to one or more control sequences (at least to a promoter) as described herein. Typically, the expression cassette comprises three elements: a promoter sequence, an open reading frame, and a 3' untranslated region that, in eukaryotes, usually contains a polyadenylation site. Additional regulatory elements may include transcriptional as well as translational enhancers. An intron sequence may also be added to the 5' untranslated region (UTR) or in the coding sequence to increase the amount of the mature message that accumulates in the cytosol. The expression cassette may be part of a vector or may be integrated into the genome of a host cell and replicated together with the genome of its host cell. The expression cassette usually is capable of increasing or decreasing expression.

The term "vector" as used herein comprises any kind of construct suitable to carry foreign polynucleotide sequences for transfer to another cell, or for stable or transient expression within a given cell. The term "vector" as used herein encompasses any kind of cloning vehicles, such as but not limited to plasmids, phagemids, viral vectors (e.g., phages), bacteriophage, baculoviruses, cosmids, fosmids, artificial chromosomes, or and any other vectors specific for specific hosts of interest. Low copy number or high copy number vectors are also included. Foreign polynucleotide sequences usually comprise a coding sequence which may be referred to herein as "gene of interest". The gene of interest may comprise introns and exons, depending on the kind of origin or destination of host cell.

A vector as used herein may provide segments for transcription and translation of a foreign polynucleotide upon transformation into a host cell or host cell organelles. Such additional segments may include regulatory nucleotide sequences, one or more origins of replication that is required for its maintenance and/or replication in a specific cell type, one or more selectable markers, a polyadenylation signal, a suitable site for the insertion of foreign coding sequences such as a multiple cloning site etc. One example is when a vector is required to be maintained in a bacterial cell as an episomal genetic element (e.g. plasmid or cosmid molecule). Non-limiting examples of suitable origins of replication include the fl-ori and colEl.

A vector may replicate without integrating into the genome of a host cell, e.g. as a plasmid in a bacterial host cell, or it may integrate part or all of its DNA into the genome of the host cell and thus lead to replication and expression of its DNA.

Foreign nucleic acid may be introduced into a vector by means of cloning. Cloning may mean that by cleavage of the vector (e.g. within the multiple cloning site) and the foreign polynucleotide by suitable means and methods (e.g., restriction enzymes), fitting structures within the individual nucleic acids may be created that enable the controlled fusion of said foreign nucleic acid and the vector.

Once introduced into the vector, the foreign nucleic acid comprising a coding sequence may be suitable to be introduced (transformed, transduced, transfected, etc.) into a host cell or host cell organelles. A cloning vector may be chosen suitable for expression of the foreign polynucleotide sequence in the host cell or host cell organelles.

The term "introduction" or "transformation" as referred to herein encompasses the transfer of an exogenous polynucleotide into a host cell, irrespective of the method used for transfer. That is, the term "transformation" as used herein is independent from vector, shuttle system, or host cell, and it not only relates to the polynucleotide transfer method of transformation as known in the art (cf., for example, Sambrook, J. et al. (1989) Molecular Cloning: A Laboratory Manual, 2nd Ed., Cold Spring Harbor Laboratory Press, Cold Spring Harbor, N.Y.), but it encompasses any further kind polynucleotide transfer methods such as, but not limited to, transduction or transfection. Plant tissue capable of subsequent clonal propagation, whether by organogenesis or embryogenesis, may be transformed with a genetic construct and a whole plant regenerated therefrom. The particular tissue chosen will vary depending on the clonal propagation systems available for, and best suited to, the particular species being transformed.

In one embodiment of the invention, a vector is used for transformation of a host cell.

The polynucleotide may be transiently or stably introduced into a host cell and may be maintained non-integrated, for example, as a plasmid. "Stable transformation" may mean that the transformed cell or cell organelle passes the nucleic acid comprising the foreign coding sequence on to the next generations of the cell or cell organelles. Usually stable transformation is due to integration of nucleic acid comprising a foreign coding sequence into the chromosomes or as an episome (separate piece of nuclear DNA).

"Transient transformation" may mean that the cell or cell organelle once transformed expresses the foreign nucleic acid sequence for a certain time—mostly within one generation. Usually transient transformation is due to nucleic acid comprising a foreign nucleic acid sequence is not integrated into the chromosomes or as an episome.

Alternatively, it may be integrated into the host genome. The resulting transformed plant cell may then be used to regenerate a transformed plant in a manner known to persons skilled in the art.

Recombinant cells may exhibit "increased" or "decreased" expression when compared to the respective wild-type cell.

The term "increased expression", "enhanced expression" or "overexpression" as used herein means any form of expression that is additional to the original wild-type expression level (which can be absence of expression or immeasurable expression as well). Reference herein to "increased expression", "enhanced expression" or "overexpression" is taken to mean an increase in gene expression and/or, as far as referring to polypeptides, increased polypeptide levels and/or increased polypeptide activity, relative to control organisms. The increase in expression may be in increasing order of preference at least 5%, at least 10%, at least 20%, at least 30%, at least 40%, at least 50%, at least 60%, at least 70%, at least 80%, at least 85%, at least 90%, or 100% or even more compared to that of control organisms.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to increase expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO 93/22443), or isolated promoters may be introduced into an organism in the proper orientation and distance from a gene of the present invention so as to control the expression of the gene.

An intron sequence may also be added to the 5' untranslated region (UTR) or the coding sequence of the partial coding sequence to increase the amount of the mature message that accumulates in the cytosol. Inclusion of a spliceable intron in the transcription unit in expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit.

To obtain increased expression or overexpression of a polypeptide most commonly the nucleic acid encoding this polypeptide is overexpressed in sense orientation with a polyadenylation signal. Introns or other enhancing elements may be used in addition to a promoter suitable for driving expression with the intended expression pattern.

Enzymes are generally produced commercially by using recombinant cells which express the desired enzyme by cultivation of the same under conditions suitable for expression of the desired enzyme.

Cultivation normally takes place in a suitable nutrient medium allowing the recombinant cells to grow (this process may be called fermentation) and express the desired protein. At the end of fermentation, fermentation broth is collected and may be further processed, wherein the fermentation broth comprises a liquid fraction and a solid fraction.

The enzyme of interest may be further purified from the fermentation broth. The term "purification" or "purifying" refers to a process in which at least one component, e.g., a protein of interest, is separated from at least another component, e.g., a particulate matter of a fermentation broth, and transferred into a different compartment or phase, wherein the different compartments or phases do not necessarily need to be separated by a physical barrier. Examples of such different compartments are two compartments separated by a filtration membrane or cloth, i.e., filtrate and retentate; examples of such different phases are pellet and supernatant or cake and filtrate, respectively. The resulting solution after purifying the enzyme of interest from the fermentation broth is called herein "purified enzyme solution".

The desired enzyme may be secreted (into the liquid fraction of the fermentation broth) or may not be secreted from the host cells (and therefore is comprised in the cells of the fermentation broth). Depending on this, the desired enzyme may be recovered from the liquid fraction of the fermentation broth or from cell lysates. Recovery of the desired enzyme uses methods known to those skilled in the art. Suitable methods for recovery of proteins or enzymes from fermentation broth include but are not limited to collection, centrifugation, filtration, extraction, and precipitation. If the enzyme of interest precipitates or crystallizes in the fermentation broth or binds at least in part to the particulate matter of the fermentation broth additional treatment steps might be needed to release the enzyme from the biomass or solubilize enzyme crystals and precipitates. U.S. Pat. No. 6,316,240B1 describes a method for recovering an enzyme, which precipitates and/or crystallizes during fermentation, from the fermentation broth. In case the desired enzyme is comprised in the cells of the fermentation broth release of the enzyme from the cells might be needed. Release from the cells can be achieved for instance, but not being limited thereto, by cell lysis with techniques well known to the skilled person.

The purified enzyme solution may be further processed to form an "enzyme formulation". "Enzyme formulation" means any non-complex formulation comprising a small number of ingredients, wherein the ingredients serve the purpose of stabilizing the enzymes comprised in the enzyme formulation and/or the stabilization of the enzyme formulation itself. The term "enzyme stability" relates to the retention of enzymatic activity as a function of time during storage or operation. The term "enzyme formulation stability" relates to the maintenance of physical appearance of the enzyme formulation during storage or operation as well as the avoidance of microbial contamination during storage or operation.

An "enzyme formulation" is a composition which is meant to be formulated into a complex formulation which itself may be determined for final use. An "enzyme formulation" according to the invention is not a complex formulation comprising several components, wherein the components are formulated into the complex formulation to exert each individually a specific action in a final application. A complex formulation may be without being limited thereto a detergent formulation, wherein individual detergent components are formulated in amounts effective in the washing performance of the detergent formulation.

In one aspect of the invention, at least one amylase variant of the invention is comprised in an enzyme formulation.

The enzyme formulation can be either solid or liquid. Enzyme formulations can be obtained by using techniques known in the art. For instance, without being limited thereto, solid enzyme formulations can be obtained by extrusion or granulation. Suitable extrusion and granulation techniques are known in the art and are described for instance in WO9419444A1 and WO9743482A1.

"Liquid" in the context of enzyme formulation is related to the physical appearance at 20° C. and 101.3 kPa.

Liquid enzyme formulations may comprise amounts of enzyme in the range of 0.1% to 40% by weight, or 0.5% to 30% by weight, or 1% to 25% by weight, or 3% to 10%, all relative to the total weight of the enzyme formulation.

The liquid enzyme formulation may comprise more than one type of enzyme. In one embodiment, the enzyme formulation comprises one or more amylases according to the present invention. In one embodiment, the enzyme formulation comprises one or more amylases according to the present invention and at least one additional enzyme selected from the group consisting of selected from the group consisting of: a second amylase, a lipase, a protease, a cellulase, a laccase, a pectinase, a nuclease, and any combination thereof.

Aqueous enzyme formulations of the invention may comprise water in amounts of more than about 50% by weight, more than about 60% by weight, more than about 70% by weight, or more than about 80% by weight, all relative to the total weight of the enzyme formulation.

Liquid enzyme formulations of the invention may comprise residual components such as salts originating from the fermentation medium, cell debris originating from the production host cells, metabolites produced by the production host cells during fermentation.

In one embodiment, residual components may be comprised in liquid enzyme formulations in amounts less than 30% by weight, less than 20% by weight less, than 10% by weight, or less than 5% by weight, all relative to the total weight of the aqueous enzyme formulation. In one embodiment, the enzyme formulation, in particular the liquid enzyme formulation, comprises in addition to the one or more enzymes one or more additional compounds selected from the group consisting of solvent, salt, pH regulator, preservative, stabilizer, chelators, and thickening agent. The preservative in a liquid enzyme formulation maybe a sorbitol, a benzoate, a proxel, or any combination therefore. The stabilizers in a liquid enzyme formulation maybe an MPG, a glycerol, an acetate, or any combination thereof. The chelators in a liquid enzyme formulation maybe a citrate.

In one embodiment, an enzyme formulation comprises at least one polypeptide variant of the invention and at least one preservative. Non-limiting examples of suitable preservatives include (quaternary) ammonium compounds, isothiazolinones, organic acids, and formaldehyde releasing agents. Non-limiting examples of suitable (quaternary) ammonium compounds include benzalkonium chlorides, polyhexamethylene biguanide (PHMB), Didecyldimethylammonium chloride (DDAC), and N-(3-aminopropyl)-N-dodecylpropane-1,3-diamine (Diamine). Non-limiting examples of suitable isothiazolinones include 1,2-benzisothiazolin-3-one (BIT), 2-methyl-2H-isothiazol-3-one (MIT), 5-chloro-2-methyl-2H-isothiazol-3-one (CIT), 2-octyl-2H-isothiazol-3-one (OIT), and 2-butyl-benzo[d]isothiazol-3-one (BBIT). Non-limiting examples of suitable organic acids include benzoic acid, sorbic acid, L-(+)-lactic acid, formic acid, and salicylic acid. Non-limiting examples of suitable formaldehyde releasing agent include N,N'-methylenebismorpholine (MBM), 2,2',2"-(hexahydro-1,3,5-triazine-1,3,5-triyl)triethanol (HHT), (ethylenedioxy)dimethanol, .alpha.,.alpha.',.alpha.".-trimethyl-1,3,5-triazine-1,3,5 (2H,4H,6H)-triethanol (HPT), 3,3'-methylenebis[5-methyloxazolidine] (MBO), and cis-1-(3-chloroallyl)-3,5,7-triaza-1-azoniaadamantane chloride (CTAC).

Further useful preservatives include iodopropynyl butyl-carbamate (IPBC), halogen releasing compounds such as dichloro-dimethyl-hydantoine (DCDMH), bromo-chloro-di-methyl-hydantoine (BCDMH), and dibromo-dimethyl-hydantoine (DBDMH); bromo-nitro compounds such as Bronopol (2-bromo-2-nitropropane-1,3-diol), 2,2-dibromo-2-cyanoacetamide (DBNPA); aldehydes such as glutaraldehyde; phenoxyethanol; Biphenyl-2-ol; and zinc or sodium pyrithione.

In one embodiment, an enzyme formulation comprises at least one polypeptide variant of the invention and at least one enzyme stabilizer. An enzyme stabilizer is selected from substances which are capable of reducing loss of enzymatic activity during storage of at least one enzyme comprised in a liquid enzyme formulation. Reduced loss of enzymatic activity within this invention may mean that the loss of enzymatic activity is reduced by at least 5%, by at least 10%, by at least 15%, by at least 20%, by at least 25%, by at least 30%, by at least 40%, by at least 50%, by least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% when compared to the initial enzymatic activity before storage. Preferred stabilizers are selected from the group consisting of salt (e.g., CaCl2), propanediol, polyethylene glycol, an MPG, a glycerol, an acetate, or any combination thereof.

Enzyme Applications

In another embodiment, the polypeptide variant as described herein may be used in foods, for example the enzyme can be an additive for baking. The enzymes can be used in feed, for example the enzyme is an animal feed additive. The enzyme can be used in the starch processing industry, for example the amylases are used in the conversion of starch to ethanol or sugars (high fructose corn syrup) and other byproducts such as oil, dry distiller's grains, etc. The polypeptide variants are used in in pulp and paper processing, for example, the enzymes can be used for improving paper strength. The enzymes can be used for mining and oil well services, for example cellulases can be used for breaking guar during oil well fracturing. In one embodiment, the polypeptide variant as described herein are used in detergent formulations or cleaning formulations.

In one embodiment, the present invention refers to a method of preparing a dough or a baked product prepared from the dough, the method comprising adding one of the variant polypeptides having amylase activity as described herein to the dough and baking it. In one embodiment, the present invention refers to a method of use of the variant polypeptide having amylase activity as described herein for processing starch. In one embodiment, the present invention refers to a method of use of the variant polypeptide having amylase activity as described herein for cleaning or washing textiles, hard surfaces, or dishes. In one embodiment, the present invention refers to a method of use of the variant polypeptide having amylase activity as described herein for making ethanol. In one embodiment, the present invention refers to a method of use of the variant polypeptide having amylase activity as described herein for processing pulp or paper. In one embodiment, the present invention refers to a method of use of the variant polypeptide having amylase activity as described herein for feeding an animal.

In one embodiment, the amylases of the present invention are used in detergent formulations or cleaning formulations.

"Detergent formulation" or "cleaning formulation" means compositions designated for cleaning soiled material. Cleaning includes laundering and hard surface cleaning. Soiled material according to the invention includes textiles and/or hard surfaces.

The term "laundering" relates to both household laundering and industrial laundering and means the process of treating textiles with a solution containing a detergent composition of the present invention. The laundering process may be carried out by using technical devices such as a household or an industrial washing machine. Alternatively, the laundering process may be done by hand.

The term "textile" means any textile material including yarns (thread made of natural or synthetic fibers used for knitting or weaving), yarn intermediates, fibers, non-woven materials, natural materials, synthetic materials, as well as fabrics (a textile made by weaving, knitting or felting fibers) made of these materials such as garments (any article of clothing made of textile), cloths and other articles.

The term "fibers" includes natural fibers, synthetic fibers, and mixtures thereof. Examples of natural fibers are of plant (such as flax, jute and cotton) or animal origin, comprising proteins like collagen, keratin and fibroin (e.g. silk, sheep wool, angora, mohair, cashmere). Examples for fibers of synthetic origin are polyurethane fibers such as Spandex® or Lycra®, polyester fibers, polyolefins such as elastofin, or polyamide fibers such as nylon. Fibers may be single fibers or parts of textiles such as knitwear, woven, or nonwovens.

The term "hard surface cleaning" is defined herein as cleaning of hard surfaces wherein hard surfaces may include any hard surfaces in the household, such as floors, furnishing, walls, sanitary ceramics, glass, metallic surfaces including cutlery or dishes.

The term "dish wash" refers to all forms of washing dishes, e.g. by hand or automatic dish wash. Dish washing includes, but is not limited to, the cleaning of all forms of crockery such as plates, cups, glasses, bowls, all forms of cutlery such as spoons, knives, forks and serving utensils as well as ceramics, plastics such as melamine, metals, china, glass and acrylics.

The detergent formulation of the invention comprises one or more detergent component(s). The component(s) chosen depend(s) on the desired cleaning application and/or physical form of a detergent composition.

The term "detergent component" is defined herein to mean any types of ingredient, which is suitable for detergent compositions, such as surfactants, building agents, polymers, bleaching systems. Any component(s) known in the art acknowledging their known characteristics are suitable detergent component(s) according to the invention. Detergent components in one embodiment means components which provide washing or cleaning performance, or which effectively aid the processing (maintain physical characteristics during processing, storage and use; e.g. rheology modifiers, hydrotropes, desiccants) when present in effective amounts.

Usually, a detergent composition is a complex formulation of more than two detergent components.

Detergent components may have more than one function in the final application of a detergent formulation, therefore any detergent component mentioned in the context of a specific function herein, may also have another function in the final application of a detergent formulation. The function of a specific detergent component in the final application of a detergent formulation usually depends on its amount within the detergent formulation, i.e. the effective amount of a detergent component.

The term "effective amount" includes amounts of certain components to provide effective stain removal and effective cleaning conditions (e.g. pH, quantity of foaming), amounts of certain components to effectively provide optical benefits (e.g. optical brightening, dye transfer inhibition), and amounts of certain components to effectively aid the processing (maintain physical characteristics during processing, storage and use; e.g. rheology modifiers, hydrotropes, desiccants).

In one embodiment, a detergent formulation is a formulation of more than two detergent components, wherein at least one component is effective in stain-removal, at least one component is effective in providing the optimal cleaning conditions, and at least one component is effective in maintaining the physical characteristics of the detergent.

Cleaning performance is evaluated under relevant cleaning conditions. The term "relevant cleaning conditions" herein refers to the conditions, particularly cleaning temperature, time, cleaning mechanics, suds concentration, type of detergent and water hardness, actually used in laundry machines, automatic dish washers or in manual cleaning processes.

Individual detergent components and usage in detergent compositions are known to those skilled in the art. Suitable detergent components comprise inter alia surfactants, builders, polymers, alkaline, bleaching systems, fluorescent whitening agents, suds suppressors and stabilizers, hydrotropes, and corrosion inhibitors. Further examples are described e.g. in "complete Technology Book on Detergents with Formulations (Detergent Cake, Dishwashing Detergents, Liquid & Paste Detergents, Enzyme Detergents, Cleaning Powder & Spray Dried Washing Powder)", Engineers India Research Institute (EIRI), $6^{th}$ edition (2015). Another reference book for those skilled in the art may be "Detergent Formulations Encyclopedia", Solverchem Publications, 2016.

Detergent components vary in type and/or amount in a detergent formulation depending on the desired application such as laundering white textiles, colored textiles, and wool. The component(s) chosen further depend(s) on physical form of a detergent formulation (liquid, solid, gel, provided in pouches or as a tablet, etc.). The component(s) chosen e.g. for laundering formulations further depend on regional conventions which themselves are related to aspects like washing temperatures used, mechanics of laundry machine (vertical vs. horizontal axis machines), water consumption per wash cycle etc. and geographical characteristics like average hardness of water.

For example: A low detergent concentration system includes laundering formulations where less than about 800 ppm of detergent components are present in the wash water. A medium detergent concentration includes laundering formulations where between about 800 ppm and about 2,000 ppm of detergent components are present in the wash water. A high detergent concentration includes laundering formulations where more than about 2,000 ppm of detergent components are present in the wash water.

The numeric ranges recited for the individual detergent components provide amounts comprised in detergent compositions. Such ranges have to be understood to be inclusive of the numbers defining the range and include each integer within the defined range.

If not described otherwise, "% by weight" or "% w/w" is meant to be related to total detergent composition. In this case "% by weight" or "% w/w" is calculated as follows: concentration of a substance as the weight of that substance divided by the total weight of the composition, multiplied by 100.

Detergent formulations of the invention may comprise one or more surfactant(s). "Surfactant" (synonymously used herein with "surface active agent") means an organic chemical that, when added to a liquid, changes the properties of that liquid at an interface. According to its ionic charge, a surfactant is called non-ionic, anionic, cationic, or ampho- teric.

Non-limiting examples of surfactants are disclosed McCutcheon's 2016 Detergents and Emulsifiers, and McCutcheon's 2016 Functional Materials, both North American and International Edition, MC Publishing Co, 2016 edition. Further useful examples are disclosed in earlier editions of the same publications which are known to those skilled in the art.

Non-ionic surfactant means a surfactant that contains neither positively nor negatively charged (i.e. ionic) func- tional groups. In contrast to anionic and cationic surfactants, non-ionic surfactants do not ionize in solution.

Example 1: Amylase Fragment Identification and Reassembly

The parent amino acid sequences of the amylases (Amy- lase 51, SEQ ID NO: 101) and SEQ ID NO: 131, were aligned in silico and divided into 4 regions spanning the aligned genes. Each of the four regions, (hereafter referred to as Region 1, Region 2, Region 3, and Region 4) was further divided into fragments as described in the table below. For example, Region 1 has fragment "a" (SEQ ID NO:103) or fragment "b" (SEQ ID NO:104). Altogether 28 unique fragments were designed having the amino acid sequences SEQ ID NO: 103 to 130. The fragments were synthetically generated by Integrated DNA Technologies, Inc. (IDT) (Illinois, USA) and reassembled in an ordered fashion to produce different combinations of fragments resulting in new hybrid amylase backbones (SEQ ID NOs: 1-100) that have different amino acid sequences when compared to the parent backbones. Each new hybrid amy- lase backbone was comprised of a single fragment from each of Region 1, Region 2, Region 3, and Region 4, respectively, from the beginning to the end of the mature gene coding sequence. The fragments were assembled using a sequential Golden Gate assembly approach as follows: Each of the 28 gene fragments were designed with flanking regions con- taining TypeIIs restriction enzyme recognition sites and specific nucleotides to generate compatible overhangs with the relevant adjacent fragments. All 28 fragments were PCR amplified and fragments from each region were pooled in an equimolar ratio. An *E. coli* vector backbone was then PCR amplified using primers to add terminal TypeIIs restriction enzyme recognition sites and specific nucleotides to create compatible overhangs for ligation with the 5' termini of Region 1 and the 3' terminus of Region 4. Golden Gate assembly was used to ligate the *E. coli* vector backbone and the pooled fragments from Region 1, Region 2, Region 3, and Region 4. The assembled constructs were subsequently transformed into an *E. coli* cloning host and plated onto selective agar plates. The resulting colonies were mixed together and plasmid DNA from the mixture was extracted, resulting in a library of fully assembled hybrid amylases. PCR was then used to amplify the full-length hybrid amy- lase variants from the extracted plasmid library and add appropriate restriction recognition sites and Golden Gate compatible overhangs on the termini. Similarly, a *Bacillus* expression vector was PCR amplified using primers to add terminal Golden Gate compatible sequences. The amplified *Bacillus* backbone and amplified library of hybrid amylases were then assembled using a second Golden Gate reaction and transformed into a *Bacillus subtilis* host and grown on selective agar plates. The resulting colonies were screened for correctly assembled full-length hybrid amylases via colony PCR and Sanger sequencing.

Full Length (Mature) Hybrid Amylase

| Enzyme Name | Amino Acid Sequence (SEQ ID NO: ) | DNA Sequence (SEQ ID NO: ) | Regions and fragments Amino Acid Sequence (SEQ ID NO: ) | | | |
|---|---|---|---|---|---|---|
| | | | Region 1 | Region 2 | Region 3 | Region 4 |
| Amylase_01 | 1 | 2 | b is SEQ ID NO: 104 | f is SEQ ID NO: 110 | f is SEQ ID NO: 118 | e is SEQ ID NO: 125 |
| Amylase_02 | 3 | 4 | b is SEQ ID NO: 104 | b is SEQ ID NO: 106 | h is SEQ ID NO: 120 | f is SEQ ID NO: 126 |
| Amylase_03 | 5 | 6 | b is SEQ ID NO: 104 | b is SEQ ID NO: 106 | f is SEQ ID NO: 118 | g is SEQ ID NO: 127 |
| Amylase_04 | 7 | 8 | b is SEQ ID NO: 104 | d is SEQ ID NO: 108 | f is SEQ ID NO: 118 | f is SEQ ID NO: 126 |
| Amylase_05 | 9 | 10 | a is SEQ ID NO: 103 | g is SEQ ID NO: 111 | e is SEQ ID NO: 117 | h is SEQ ID NO: 128 |
| Amylase_06 | 11 | 12 | a is SEQ ID NO: 103 | h is SEQ ID NO: 112 | e is SEQ ID NO: 117 | g is SEQ ID NO: 127 |
| Amylase_07 | 13 | 14 | b is SEQ ID NO: 104 | h is SEQ ID NO: 112 | e is SEQ ID NO: 117 | b is SEQ ID NO: 122 |
| Amylase_08 | 15 | 16 | b is SEQ ID NO: 104 | d is SEQ ID NO: 108 | e is SEQ ID NO: 117 | f is SEQ ID NO: 126 |
| Amylase_09 | 17 | 18 | a is SEQ ID NO: 103 | h is SEQ ID NO: 112 | e is SEQ ID NO: 117 | f is SEQ ID NO: 126 |
| Amylase_10 | 19 | 20 | b is SEQ ID NO: 104 | d is SEQ ID NO: 108 | e is SEQ ID NO: 117 | d is SEQ ID NO: 124 |
| Amylase_11 | 21 | 22 | a is SEQ ID NO: 103 | d is SEQ ID NO: 108 | f is SEQ ID NO: 118 | g is SEQ ID NO: 127 |
| Amylase_12 | 23 | 24 | b is SEQ ID NO: 104 | b is SEQ ID NO: 106 | b is SEQ ID NO: 114 | e is SEQ ID NO: 125 |
| Amylase_13 | 25 | 26 | b is SEQ ID NO: 104 | d is SEQ ID NO: 108 | e is SEQ ID NO: 117 | e is SEQ ID NO: 125 |
| Amylase_14 | 27 | 28 | b is SEQ ID NO: 104 | f is SEQ ID NO: 110 | e is SEQ ID NO: 117 | a is SEQ ID NO: 121 |
| Amylase_15 | 29 | 30 | a is SEQ ID NO: 103 | b is SEQ ID NO: 106 | e is SEQ ID NO: 117 | h is SEQ ID NO: 128 |
| Amylase_16 | 31 | 32 | a is SEQ ID NO: 103 | h is SEQ ID NO: 112 | g is SEQ ID NO: 119 | b is SEQ ID NO: 122 |
| Amylase_17 | 33 | 34 | a is SEQ ID NO: 103 | h is SEQ ID NO: 112 | e is SEQ ID NO: 117 | e is SEQ ID NO: 125 |
| Amylase_18 | 35 | 36 | b is SEQ ID NO: 104 | b is SEQ ID NO: 106 | e is SEQ ID NO: 117 | e is SEQ ID NO: 125 |
| Amylase_19 | 37 | 38 | b is SEQ ID NO: 104 | e is SEQ ID NO: 109 | e is SEQ ID NO: 117 | a is SEQ ID NO: 121 |
| Amylase_20 | 39 | 40 | a is SEQ ID NO: 103 | f is SEQ ID NO: 110 | e is SEQ ID NO: 117 | e is SEQ ID NO: 125 |
| Amylase_21 | 41 | 42 | a is SEQ ID NO: 103 | h is SEQ ID NO: 112 | e is SEQ ID NO: 117 | i is SEQ ID NO: 129 |

-continued

Full Length (Mature) Hybrid Amylase

| Enzyme<br>Name | Amino Acid<br>Sequence<br>(SEQ ID<br>NO: ) | DNA<br>Sequence<br>(SEQ ID<br>NO: ) | Regions and fragments Amino Acid Sequence (SEQ ID NO: ) | | | |
|---|---|---|---|---|---|---|
| | | | Region 1 | Region 2 | Region 3 | Region 4 |
| Amylase_22 | 43 | 44 | b is SEQ ID NO: 104 | b is SEQ ID NO: 106 | e is SEQ ID NO: 117 | c is SEQ ID NO: 123 |
| Amylase_23 | 45 | 46 | a is SEQ ID NO: 103 | f is SEQ ID NO: 110 | e is SEQ ID NO: 117 | c is SEQ ID NO: 123 |
| Amylase_24 | 47 | 48 | a is SEQ ID NO: 103 | f is SEQ ID NO: 110 | c is SEQ ID NO: 115 | c is SEQ ID NO: 123 |
| Amylase_25 | 49 | 50 | a is SEQ ID NO: 103 | d is SEQ ID NO: 108 | e is SEQ ID NO: 117 | g is SEQ ID NO: 127 |
| Amylase_26 | 51 | 52 | a is SEQ ID NO: 103 | d is SEQ ID NO: 108 | f is SEQ ID NO: 118 | e is SEQ ID NO: 125 |
| Amylase_27 | 53 | 54 | b is SEQ ID NO: 104 | d is SEQ ID NO: 108 | e is SEQ ID NO: 117 | b is SEQ ID NO: 122 |
| Amylase_28 | 55 | 56 | b is SEQ ID NO: 104 | d is SEQ ID NO: 108 | a is SEQ ID NO: 113 | c is SEQ ID NO: 123 |
| Amylase_29 | 57 | 58 | a is SEQ ID NO: 103 | d is SEQ ID NO: 108 | e is SEQ ID NO: 117 | f is SEQ ID NO: 126 |
| Amylase_30 | 59 | 60 | a is SEQ ID NO: 103 | f is SEQ ID NO: 110 | e is SEQ ID NO: 117 | b is SEQ ID NO: 122 |
| Amylase_31 | 61 | 62 | a is SEQ ID NO: 103 | b is SEQ ID NO: 106 | e is SEQ ID NO: 117 | f is SEQ ID NO: 126 |
| Amylase_32 | 63 | 64 | a is SEQ ID NO: 103 | f is SEQ ID NO: 110 | g is SEQ ID NO: 119 | a is SEQ ID NO: 121 |
| Amylase_33 | 65 | 66 | a is SEQ ID NO: 103 | d is SEQ ID NO: 108 | b is SEQ ID NO: 114 | e is SEQ ID NO: 125 |
| Amylase_34 | 67 | 68 | a is SEQ ID NO: 103 | d is SEQ ID NO: 108 | e is SEQ ID NO: 117 | d is SEQ ID NO: 124 |
| Amylase_35 | 69 | 70 | a is SEQ ID NO: 103 | d is SEQ ID NO: 108 | g is SEQ ID NO: 119 | c is SEQ ID NO: 123 |
| Amylase_36 | 71 | 72 | b is SEQ ID NO: 104 | d is SEQ ID NO: 108 | e is SEQ ID NO: 117 | a is SEQ ID NO: 121 |
| Amylase_37 | 73 | 74 | b is SEQ ID NO: 104 | b is SEQ ID NO: 106 | e is SEQ ID NO: 117 | a is SEQ ID NO: 121 |
| Amylase_38 | 75 | 76 | a is SEQ ID NO: 103 | f is SEQ ID NO: 110 | e is SEQ ID NO: 117 | a is SEQ ID NO: 121 |
| Amylase_39 | 77 | 78 | b is SEQ ID NO: 104 | c is SEQ ID NO: 107 | e is SEQ ID NO: 117 | a is SEQ ID NO: 121 |
| Amylase_40 | 79 | 80 | a is SEQ ID NO: 103 | d is SEQ ID NO: 108 | e is SEQ ID NO: 117 | e is SEQ ID NO: 125 |
| Amylase_41 | 81 | 82 | a is SEQ ID NO: 103 | b is SEQ ID NO: 106 | e is SEQ ID NO: 117 | e is SEQ ID NO: 125 |
| Amylase_42 | 83 | 84 | a is SEQ ID NO: 103 | d is SEQ ID NO: 108 | e is SEQ ID NO: 117 | j is SEQ ID NO: 130 |
| Amylase_43 | 85 | 86 | a is SEQ ID NO: 103 | b is SEQ ID NO: 106 | e is SEQ ID NO: 117 | c is SEQ ID NO: 123 |
| Amylase_44 | 87 | 88 | a is SEQ ID NO: 103 | e is SEQ ID NO: 109 | e is SEQ ID NO: 117 | a is SEQ ID NO: 121 |
| Amylase_45 | 89 | 90 | a is SEQ ID NO: 103 | d is SEQ ID NO: 108 | e is SEQ ID NO: 117 | b is SEQ ID NO: 122 |
| Amylase_46 | 91 | 92 | a is SEQ ID NO: 103 | c is SEQ ID NO: 107 | e is SEQ ID NO: 117 | c is SEQ ID NO: 123 |
| Amylase_47 | 93 | 94 | a is SEQ ID NO: 103 | b is SEQ ID NO: 106 | e is SEQ ID NO: 117 | b is SEQ ID NO: 122 |
| Amylase_48 | 95 | 96 | a is SEQ ID NO: 103 | d is SEQ ID NO: 108 | e is SEQ ID NO: 117 | a is SEQ ID NO: 121 |
| Amylase_49 | 97 | 98 | a is SEQ ID NO: 103 | b is SEQ ID NO: 106 | e is SEQ ID NO: 117 | a is SEQ ID NO: 121 |
| Amylase_50 | 99 | 100 | a is SEQ ID NO: 103 | b is SEQ ID NO: 106 | a is SEQ ID NO: 113 | a is SEQ ID NO: 121 |
| Amylase_51 | 101 | 102 | a is SEQ ID NO: 103 | a is SEQ ID NO: 105 | a is SEQ ID NO: 113 | a is SEQ ID NO: 121 |

Example 2: Amylase Expression and Protein Quantification

Single colonies of the expression strains were picked into 60 μL of LB media containing 2% glucose and kanamycin in a 384-well plate. The cultures were grown at 37 degrees C. for 16 hours, then 15 μL of culture was used to inoculate 600 μL of 2 L media (twice the components of LB media) containing 7.5% maltose and 20 μg/mL kanamycin in a 96-well plate. The cultures were grown at 37 degrees C. for 48 hours, after which the supernatant was harvested by centrifugation at 5000×g for 15 minutes at 4 degrees C. The expression levels (concentration in mg/mL) of variant polypeptide hybrids having alpha-amylase activity were identified by LabChip (LC) analysis and corresponding expression plasmids were sequenced.

The results, which were normalized for expression as provided in the table below, show that many of the hybrid amylase enzymes have an increase in expression when compared to the parent enzyme (Amylase_051). For example, Amylase_01, Amylase_02, Amylase_03, Amylase_04, Amylase_05, Amylase_06, Amylase_07, Amylase_08, Amylase_09, Amylase_11, Amylase_12, Amylase_13, Amylase_14, Amylase_15, Amylase_17, Amylase_18, Amylase_19, Amylase_20, Amylase_21, Amylase_22, Amylase_23, Amylase_25, Amylase_26, Amylase_27, Amylase_28, Amylase_29, Amylase_30, Amylase_31, Amylase_33, Amylase_34, Amylase_36, Amylase_37, Amylase_38, Amylase_39, Amylase_40, Amylase_41, Amylase_42, Amylase_43, Amylase_44, Amylase_45, Amylase_46, Amylase_47, Amylase_48, Amylase_49, Amylase_50, have an increase in expression ranging from 1.01 to 1.27.

| Normalized<br>Expression | Enzyme<br>Name |
|---|---|
| 1.14 | Amylase_01 |
| 1.09 | Amylase_02 |
| 1.19 | Amylase_03 |
| 1.18 | Amylase_04 |
| 1.23 | Amylase_05 |
| 1.24 | Amylase_06 |
| 1.03 | Amylase_07 |
| 1.26 | Amylase_08 |
| 1.21 | Amylase_09 |
| 1.00 | Amylase_10 |
| 1.16 | Amylase_11 |
| 1.18 | Amylase_12 |
| 1.27 | Amylase_13 |
| 1.12 | Amylase_14 |
| 1.16 | Amylase_15 |
| 0.92 | Amylase_16 |
| 1.23 | Amylase_17 |
| 1.22 | Amylase_18 |
| 1.05 | Amylase_19 |
| 1.22 | Amylase_20 |
| 1.16 | Amylase_21 |
| 1.12 | Amylase_22 |
| 1.14 | Amylase_23 |
| 0.95 | Amylase_24 |
| 1.23 | Amylase_25 |
| 1.18 | Amylase_26 |
| 1.11 | Amylase_27 |
| 1.06 | Amylase_28 |
| 1.18 | Amylase_29 |
| 1.04 | Amylase_30 |
| 1.20 | Amylase_31 |
| 1.00 | Amylase_32 |
| 1.12 | Amylase_33 |
| 1.01 | Amylase_34 |

-continued

| Normalized Expression | Enzyme Name |
|---|---|
| 1.00 | Amylase_35 |
| 1.26 | Amylase_36 |
| 1.24 | Amylase_37 |
| 1.09 | Amylase_38 |
| 1.17 | Amylase_39 |
| 1.12 | Amylase_40 |
| 1.26 | Amylase_41 |
| 1.15 | Amylase_42 |
| 1.11 | Amylase_43 |
| 1.04 | Amylase_44 |
| 1.12 | Amylase_45 |
| 1.07 | Amylase_46 |
| 1.14 | Amylase_47 |
| 1.25 | Amylase_48 |
| 1.13 | Amylase_49 |
| 1.09 | Amylase_50 |
| 1.00 | Amylase_51 |

Example 3: Red Starch and Residual Activity Assays

Quantitation of starch hydrolysis for the variant polypeptides containing alpha-amylase activity was measured using the Red Starch method as described by Megazyme, "Assay of Alpha-Amylase using Red-Starch" with the following modifications. 10 μL of 1.33% red starch prepared in 50 mM HEPES, pH 8.0 buffer was reacted with 10 μL enzyme diluted in 50 mM HEPES, pH 8.0 buffer at 25° C. The reaction was terminated after 10 minutes by the addition of 50 μL of 200 proof ethanol. After vigorous mixing the reaction was equilibrated for 10 minutes at room temperature followed by centrifugation at 1,200×g for 10 minutes. 40 μL of the reaction was transferred and the solution absorption (AU) was read at 510 nm in a BioTek plate reader. Residual activity was calculated by comparing the activity of each enzyme as measured using the red starch assay before and after a heat challenge. Heat challenges were conducted on enzyme diluted in 50 mM HEPES, pH 8.0 buffer in two separate instances with different heating regimes. In one instance, the diluted enzyme was heated to 80 degrees C. for 30 minutes, chilled at 8 degrees C. for 20 minutes, and equilibrated to room temperature for 20 minutes before being tested using the red starch assay at 25 degrees C. In a separate instance, the diluted enzyme was heated to 90 degrees C. for 15 minutes, chilled at 4 degrees C. for 10 minutes, then held at 24 degrees C. for 5 minutes before being tested using the red starch assay at 25 degrees C.

The table below shows the remaining activity of the amylase after heat treatment. The results, as provided in the table below, show that all the amylases are more thermostable when compared to the parent enzyme (Amylase_51).

| Amylase Hybrid Residual Activity (90 degrees C.) | |
|---|---|
| Percent Activity Remaining | Enzyme Name |
| 50.2 | Amylase_01 |
| 71.5 | Amylase_02 |
| 96.3 | Amylase_03 |
| 54.1 | Amylase_04 |
| 51.1 | Amylase_05 |
| 65.7 | Amylase_06 |
| 51.9 | Amylase_07 |

-continued

| Amylase Hybrid Residual Activity (90 degrees C.) | |
|---|---|
| Percent Activity Remaining | Enzyme Name |
| 53.0 | Amylase_08 |
| 50.7 | Amylase_09 |
| 50.2 | Amylase_10 |
| 116.1 | Amylase_11 |
| 72.5 | Amylase_12 |
| 60.4 | Amylase_13 |
| 63.5 | Amylase_14 |
| 71.0 | Amylase_15 |
| 65.7 | Amylase_16 |
| 59.2 | Amylase_17 |
| 56.9 | Amylase_18 |
| 61.9 | Amylase_19 |
| 54.0 | Amylase_20 |
| 52.3 | Amylase_21 |
| 51.7 | Amylase_22 |
| 93.5 | Amylase_23 |
| 76.0 | Amylase_24 |
| 51.0 | Amylase_25 |
| 64.5 | Amylase_26 |
| 56.9 | Amylase_27 |
| 82.4 | Amylase_28 |
| 51.9 | Amylase_29 |
| 51.0 | Amylase_30 |
| 51.4 | Amylase_31 |
| 63.4 | Amylase_32 |
| 53.7 | Amylase_33 |
| 65.5 | Amylase_34 |
| 56.6 | Amylase_35 |
| 55.9 | Amylase_36 |
| 50.3 | Amylase_37 |
| 121.0 | Amylase_38 |
| 62.7 | Amylase_39 |
| 61.6 | Amylase_40 |
| 67.3 | Amylase_41 |
| 73.0 | Amylase_42 |
| 70.7 | Amylase_43 |
| 83.9 | Amylase_44 |
| 63.5 | Amylase_45 |
| 65.5 | Amylase_46 |
| 120.4 | Amylase_47 |
| 89.3 | Amylase_48 |
| 59.2 | Amylase_49 |
| 63.4 | Amylase_50 |
| 11.1 | Amylase_51 |

Example 4: Enzyme Stability in Detergent Formulations

The stability of the amylase enzymes in detergent was observed by adding the enzymes of interest into commercial detergent Persil Non-Bio. The detergents containing enzyme were then mixed and stored at 37° C. At day 0, 1, 2, 3, 7, and 14, an aliquot was taken from the detergents containing enzyme and measured for activity.

At each time point (day), amylase activity was measured by analyzing the rate of p-nitrophenol (pNP) released during the enzymatic hydrolysis of Infinity™ Amylase Liquid Stable Reagent. The sample was diluted in 50 mM MOPS, pH 7.0 prior to the assay. 100 μL of the diluted sample was added to 100 μL of Infinity™ Amylase Liquid Stable Reagent. The reaction was observed at room temperature using a BioTek plate reader at 405 nm. The activity remaining was calculated by comparing the MaxV at each time point to the initial value at day 0.

The results, as provided in the table below, show that many of the amylases are more stable (have a higher % activity remaining) in detergent formulations over time when compared to the parent enzyme Amylase_51. For example, Amylase_01, Amylase_02, Amylase_03, Amylase_04, Amylase_06, Amylase_07, Amylase_08, Amylase_10, Amylase_11, Amylase_14, Amylase_16, Amylase_17, Amylase_18, Amylase_21, Amylase_22, Amylase_23, Amylase_24, Amylase_26, Amylase_27, Amylase_28, Amylase_29, Amylase_30, Amylase_32, Amylase_34, Amylase_35, Amylase_36, Amylase_37, Amylase_38, Amylase_39, Amylase_40, Amylase_43, Amylase_44, Amylase_45, Amylase_47, Amylase_48, Amylase_49, and Amylase_50, have 0.8% to 21.6% activity remaining after 14 days in detergent formulations.

| Enzyme stability (% activity remaining) in detergent formulations over time | | | |
| --- | --- | --- | --- |
| 3 Days | 7 Days | 14 Days | Enzyme Name |
| 55.9 | 28.7 | 8.7 | Amylase_01 |
| 23.6 | 14.7 | 4.8 | Amylase_02 |
| 57.4 | 32.7 | 9.1 | Amylase_03 |
| 62.8 | 45.8 | 18.2 | Amylase_04 |
| 15.5 | 4.1 | 0 | Amylase_05 |
| 23.0 | 3.1 | 1.1 | Amylase_06 |
| 40.0 | 14.5 | 2.6 | Amylase_07 |
| 24.5 | 3.3 | 0.9 | Amylase_08 |
| 25.7 | 4.1 | 0 | Amylase_09 |
| 36.6 | 11.3 | 2.3 | Amylase_10 |
| 62.3 | 41.1 | 14.6 | Amylase_11 |
| 23.6 | 5.4 | 0 | Amylase_13 |
| 39.7 | 9.9 | 1.6 | Amylase_14 |
| 14.7 | 1.9 | 0 | Amylase_15 |
| 41.9 | 15.1 | 3.7 | Amylase_16 |
| 24.2 | 3.9 | 1.3 | Amylase_17 |
| 19.4 | 1.8 | 1.2 | Amylase_18 |
| 26.9 | 4.5 | 0 | Amylase_19 |
| 16.9 | 1.7 | 0 | Amylase_20 |
| 25.5 | 4.1 | 1.7 | Amylase_21 |
| 31.2 | 8.2 | 2.4 | Amylase_22 |
| 33.5 | 7.8 | 2.1 | Amylase_23 |
| 21.9 | 3.1 | 0 | Amylase_25 |
| 69.5 | 49.3 | 21.6 | Amylase_26 |
| 46.8 | 16.0 | 3.3 | Amylase_27 |
| 1.8 | 0 | 0 | Amylase_28 |
| 23.2 | 4.8 | 1.1 | Amylase_29 |
| 36.2 | 9.6 | 1.5 | Amylase_30 |
| 18.5 | 2.8 | 0 | Amylase_31 |
| 36.0 | 9.6 | 1.6 | Amylase_32 |
| 3.7 | 0 | 0 | Amylase_33 |
| 39.1 | 13.4 | 2.2 | Amylase_34 |
| 39.4 | 13.6 | 3.3 | Amylase_35 |
| 44.8 | 16.8 | 2.0 | Amylase_36 |
| 39.5 | 9.7 | 1.7 | Amylase_37 |
| 38.6 | 8.9 | 1.2 | Amylase_38 |
| 32.9 | 7.3 | 1.3 | Amylase_39 |
| 22.0 | 3.3 | 1.7 | Amylase_40 |
| 15.1 | 1.5 | 0 | Amylase_41 |
| 23.2 | 4.0 | 0 | Amylase_42 |
| 34.3 | 10.2 | 1.9 | Amylase_43 |
| 29.3 | 6.0 | 0.8 | Amylase_44 |
| 47.4 | 17.3 | 3.0 | Amylase_45 |
| 26.4 | 7.0 | 0 | Amylase_46 |
| 36.5 | 9.8 | 2.9 | Amylase_47 |
| 46.9 | 15.6 | 2.4 | Amylase_48 |
| 35.3 | 9.0 | 1.6 | Amylase_49 |
| 0.9 | 1.7 | 1.4 | Amylase_50 |
| 0.9 | 1.6 | 0 | Amylase_51 |

Example 5: Enzyme Performance in Laundry Applications (Stain Removal)

Wash performance was measured for the hybrid amylases on cotton soiled with starch (EMPA161) purchased from CFT. Amylases were dosed at 0.1, 0.2, or 0.3 ppm in 10 mM HEPES pH 8.0, 2.7 mM hard water plus 5 g/L detergent ES1 (Lutensit A-LBS LAS 5,5% w/w, Edenor coco fatty acid C12-C18 coco fatty acid 2,4% w/w, Lutensol AO7 AEO 5,5% w/w, Texapon N70 FAEO 5,5% w/w, 1,2 propylene glycol 6,0% w/w, ethanol 2,0% w/w, KOH 2,2% w/w) plus 3% citrate, plus 150 mM CaCl2, in individual wells. Wash was conducted by agitating in orbital shakers (500 rpm) for 30 minutes at 40° C. Wash liquor was removed then the fabric was rinsed three times with water. The samples were dried overnight at room temperature. Wash performance was measured using digital image analysis of washed stains; the average RGB intensity was normalized to the parent for each sample; and then average of the three data points (0.1, 0.2, and 0.3 ppm) is provided.

The results, as provided in the table below, show the amylase enzymes that have improved performance (stain removal) when compared to the parent enzyme (Amylase_51). For example, Amylase_01, Amylase_02, Amylase_04, Amylase_05, Amylase_06, Amylase_08, Amylase_12, Amylase_13, Amylase_14, Amylase_18, Amylase_20, Amylase_21, Amylase_22, Amylase_23, Amylase_25, Amylase_26, Amylase_28, Amylase_31, Amylase_33, Amylase_36, Amylase_37, Amylase_38, Amylase_39, Amylase_41, Amylase_46, and Amylase_50, all have an Avg. RGB value from 1.07 to 1.68, which is an increase when compared to the parent enzyme (Amylase_051).

| RGB value for wash performance results (Avg. RGB for all doses) | Enzyme Name |
| --- | --- |
| 1.29 | Amylase_01 |
| 1.26 | Amylase_02 |
| 0.87 | Amylase_03 |
| 1.06 | Amylase_04 |
| 1.34 | Amylase_05 |
| 1.52 | Amylase_06 |
| 0.49 | Amylase_07 |
| 1.41 | Amylase_08 |
| 1.04 | Amylase_09 |
| 0.95 | Amylase_10 |
| 0.87 | Amylase_11 |
| 1.09 | Amylase_12 |
| 1.32 | Amylase_13 |
| 1.40 | Amylase_14 |
| 0.97 | Amylase_15 |
| 0.38 | Amylase_16 |
| 1.02 | Amylase_17 |
| 1.23 | Amylase_18 |
| 0.96 | Amylase_19 |
| 1.43 | Amylase_20 |
| 1.68 | Amylase_21 |
| 1.44 | Amylase_22 |
| 1.39 | Amylase_23 |
| 0.50 | Amylase_24 |
| 1.24 | Amylase_25 |
| 1.08 | Amylase_26 |
| 1.02 | Amylase_27 |
| 1.33 | Amylase_28 |
| 0.88 | Amylase_29 |
| 1.14 | Amylase_31 |
| 0.87 | Amylase_32 |
| 1.07 | Amylase_33 |
| 0.66 | Amylase_34 |
| 1.04 | Amylase_35 |
| 1.09 | Amylase_36 |
| 1.39 | Amylase_37 |
| 1.57 | Amylase_38 |
| 1.37 | Amylase_39 |
| 1.05 | Amylase_40 |
| 1.62 | Amylase_41 |
| 1.02 | Amylase_42 |
| 0.67 | Amylase_43 |
| 0.74 | Amylase_44 |
| 0.89 | Amylase_45 |

-continued

| RGB value for wash performance results (Avg. RGB for all doses) | Enzyme Name |
|---|---|
| 1.15 | Amylase_46 |
| 0.75 | Amylase_47 |
| 0.87 | Amylase_48 |
| 1.02 | Amylase_49 |
| 1.11 | Amylase_50 |
| 1.06 | Amylase_51 |

Example 6: Enzyme Stability in Detergent Formulations

The stability of the amylase enzymes in detergent was observed by mixing the enzymes of interest into a defined laundry formulation (Maranil DBS/LC (LAS) 5,5% w/w, Edenor coco fatty acid C12-C18 2.4% w/w, Lutensol AO7 (AEO) 5,5% w/w, Texapon N70 (AES) 5,5% w/w, 1,2 propylene glycol 6,0% w/w, ethanol 2,0% w/w, NaOH 2,2% w/w, 3% Sodium citrate, 150 ppm CaCl2, adjusted to pH 8). The detergents containing enzyme were then stored at 37° C. After several days of storage an aliquot was taken from the detergents containing enzyme and measured for residual activity.

The residual amylase activity was measured by analyzing the rate of p-nitrophenol (pNP) released during the enzymatic hydrolysis of Infinity™ Amylase Liquid Stable Reagent. The sample was diluted in 50 mM MOPS, pH 7.0 prior to the assay. 100 µL of the diluted sample was added to 100 µL of Infinity™ Amylase Liquid Stable Reagent. The reaction was observed at room temperature using a BioTek plate reader at 405 nm. The activity remaining was calculated by comparing the MaxV at each time point to the initial value at day 0.

The results, as provided in the table below, show that the amylases (a variant of Amylase_1 (SEQ ID NO: 146), a variant of Amylase_1 (SEQ ID NO: 148), a variant of Amylase_1 (SEQ ID NO: 152), a variant of Amylase_1 (SEQ ID NO: 170) and Amylase_8 (SEQ ID NO: 15), and a variant of Amylase_8 (SEQ ID NO: 171)) are more stable (have a higher % activity remaining) in detergent formulations over time when compared to the parent enzyme Amylase_51 (SEQ ID NO: 101).

| Enzyme stability (% activity remaining) in defined laundry formulations over time | | |
|---|---|---|
| 2 Days | 6 Days | Enzyme Name |
| 95% | 89% | Amylase_51 (Seq ID 101) |
| 97% | 99% | Amylase_1 (Seq ID 1) |
| 95% | 95% | variant of Amylase_1 (Seq ID 146) |
| 97% | 97% | variant of Amylase_1 (Seq ID 148) |
| 96% | 94% | variant of Amylase_1 (Seq ID 152) |
| 98% | 97% | variant of Amylase_1 (Seq ID 170) |
| 98% | 97% | Amylase_08 (Seq ID 15) |
| 98% | 98% | variant of Amylase_08 (Seq ID 171) |

Additionally, the same set of sequences were tested in Persil Non-Bio. The enzymes were mixed into the detergents and stored at 37° C. After 0 h, 24, and 48 hours an aliquot was taken from the detergents containing enzyme and measured for activity.

The residual amylase activity was measured by analyzing the rate of p-nitrophenol (pNP) released during the enzymatic hydrolysis of Infinity™ Amylase Liquid Stable Reagent. The sample was diluted in 50 mM MOPS, pH 7.0 prior to the assay. 100 µL of the diluted sample was added to 100 µL of Infinity™ Amylase Liquid Stable Reagent. The reaction was observed at room temperature using a BioTek plate reader at 405 nm. The activity remaining was calculated by comparing the MaxV at each time point to the initial value at day 0.

The results, as provided in the table below, show that the amylases (a variant of Amylase_1 (SEQ ID NO: 146), a variant of Amylase_1 (SEQ ID NO: 148), a variant of Amylase_1 (SEQ ID NO: 152), a variant of Amylase_1 (SED IQ NO: 170), Amylase_8 (SEQ ID NO: 15), and a variant of Amylase_8 (SEQ ID NO: 171)) are more stable (have a higher % activity remaining) in detergent formulations over time when compared to the parent enzyme Amylase_51 (SEQ ID NO: 101).

| Enzyme stability (% activity remaining) in detergent formulations over time | | | |
|---|---|---|---|
| 0 hours | 24 hours | 48 hours | Enzyme Name |
| 100% | 75% | 53% | Amylase_51 (Seq ID 101) |
| 100% | 100% | 98% | Amylase_1 (Seq ID 1) |
| 100% | 82% | 83% | variant of Amy_1 (Seq ID 146) |
| 100% | 95% | 94% | variant of Amylase_1 (Seq ID 148) |
| 100% | 88% | 87% | variant of Amylase_1 (Seq ID 152) |
| 100% | 92% | 91% | variant of Amylase_1 (Seq ID 170) |
| 100% | 103% | 102% | Amylase_08 (Seq ID 15) |
| 100% | 99% | 100% | variant of Amylase_08 (Seq ID 171) |

Example 7: Enzyme Performance in Laundry Applications (Stain Removal)

Wash performance was measured for the different concentrations of the hybrid amylases on the stain types CS-28 (colored rice starch) and CS-127 (Potato starch).

Amylases were dosed at 0,004 ppm and 0.02 ppm in a wash solution of 2.7 mM hard water plus 5 g/L model detergent (Maranil DBS/LC (LAS) 5,5% w/w, Edenor coco fatty acid C12-C18 2.4% w/w, Lutensol AO7 (AEO) 5,5% w/w, Texapon N70 (AES) 5,5% w/w, 1,2 propylene glycol 6,0% w/w, ethanol 2,0% w/w, NaOH 2,2% w/w, 3% Sodium citrate, 150 ppm CaCl2, adjusted to pH 8). Wash was conducted in 500 mL wash solution in launder-O-meter for 40 minutes at 40° C. Hereafter, the wash liquor was removed and the fabric was rinsed three times with water. The samples were dried overnight at room temperature. Wash performance was measured using digital image analysis of washed stains. The average RGB intensity was normalized to the parent for each sample or to the value in absence of any amylolytic activity.

The results, as provided in the table below, show that the amylase enzymes being more stable than the parent Amylase_51 have at least similar or improved performance (starch removal) when compared to the parent enzyme (Amylase_51).

| Wash performance results | CS28 0.004 ppm (in reference to control Amylase_51) | CS28 0.02 ppm (in reference to control Amylase_51) |
|---|---|---|
| Amylase_51 (SEQ ID NO: 101) | 100% | 100% |
| Amylase_1 (SEQ ID NO: 1) | 102% | 101% |
| variant of Amylase_1 (SEQ ID NO: 146) | 108% | 102% |
| variant of Amylase_51 (SEQ ID NO: 154) | 105% | 102% |
| variant of Amylase_08 (SEQ ID NO: 171) | 113% | 102% |
| variant of Amylase_1 (SEQ ID NO: 148) | 109% | 103% |
| variant of Amylase_1 (SEQ ID NO: 152) | 110% | 103% |
| Amylase_08 (SEQ ID NO: 15) | 102% | 101% |
| variant of Amylase_1 (SEQ ID NO: 170) | 104% | 103% |

| Wash performance results | CS-127 0.004 ppm (in reference to control Amylase_51) | CS-127 0.02 ppm (in reference to control Amylase_51) |
|---|---|---|
| Amylase_51 (SEQ ID NO: 101) | 100% | 100% |
| Amylase_1 (SEQ ID NO: 1) | 102% | 103% |
| variant of Amylase_1 (SEQ ID NO: 146) | 102% | 105% |
| variant of Amylase_51 (SEQ ID NO: 154) | 102% | 105% |
| variant of Amylase_08 (S SEQ ID NO: 171) | 100% | 102% |
| variant of Amylase_1 (SEQ ID NO: 148) | 103% | 105% |
| variant of Amylase_1 (SEQ ID NO: 152) | 103% | 105% |
| Amylase_08 (SEQ ID NO: 15) | 99% | 102% |
| variant of Amylase_1 (SEQ ID NO: 170) | 106% | 106% |

The invention claimed is:

1. An amylase comprising an amino acid sequence that is at least 95%, at least 96%, at least 97%, at least 98%, at least 98.5%, at least 99%, at least 99.5%, or 100% identical to the full length amino acid sequence of: SEQ ID NO:1, SEQ ID NO:3, SEQ ID NO:5, SEQ ID NO:7, SEQ ID NO:9, SEQ ID NO:11, SEQ ID NO: 12, SEQ ID NO:13, SEQ ID NO:15, or SEQ ID NO:17.

2. The amylase of claim 1, wherein the amino acid sequence is at least 96% identical to the full length amino acid sequence of: SEQ ID NO:1, SEQ ID NO:3, SEQ ID NO: 5, SEQ ID NO:7, SEQ ID NO:9, SEQ ID NO: 11, SEQ ID NO: 12, SEQ ID NO: 13, SEQ ID NO: 15, or SEQ ID NO: 17.

3. The amylase of claim 1, wherein the amino acid sequence is at least 97% identical to the full length amino acid sequence of: SEQ ID NO:1, SEQ ID NO:3, SEQ ID NO: 5, SEQ ID NO:7, SEQ ID NO:9, SEQ ID NO: 11, SEQ ID NO: 12, SEQ ID NO: 13, SEQ ID NO: 15, or SEQ ID NO: 17.

4. The amylase of claim 1, wherein the amino acid sequence is at least 98% identical to the full length amino acid sequence of: SEQ ID NO:1, SEQ ID NO:3, SEQ ID NO: 5, SEQ ID NO:7, SEQ ID NO:9, SEQ ID NO:11, SEQ ID NO: 12, SEQ ID NO: 13, SEQ ID NO: 15, or SEQ ID NO: 17.

5. The amylase of claim 1, wherein the amino acid sequence is at least 99% identical to the full length amino acid sequence of: SEQ ID NO:1, SEQ ID NO:3, SEQ ID NO: 5, SEQ ID NO:7, SEQ ID NO:9, SEQ ID NO: 11, SEQ ID NO: 12, SEQ ID NO: 13, SEQ ID NO: 15, or SEQ ID NO: 17.

6. The amylase of claim 1, wherein the amino acid sequence is at least 99.5% identical to the full length amino acid sequence of: SEQ ID NO:1, SEQ ID NO:3, SEQ ID NO: 5, or SEQ ID NO:7, SEQ ID NO:9, SEQ ID NO:11, SEQ ID NO:12, SEQ ID NO:13, SEQ ID NO:15, SEQ ID NO:17.

7. The amylase of claim 1, wherein the amino acid sequence is 100% identical to the full length amino acid sequence of: SEQ ID NO:1, SEQ ID NO:3, SEQ ID NO:5, SEQ ID NO:7, SEQ ID NO:9, SEQ ID NO: 11, SEQ ID NO:12, SEQ ID NO:13, SEQ ID NO:15, or SEQ ID NO: 17.

8. An amylase comprising an amino acid sequence that is at least 96% identical to the full length amino acid sequence of SEQ ID NO:19.

9. The amylase of claim 8, wherein the amino acid sequence is at least 97% identical to the full length amino acid sequence of SEQ ID NO:19.

10. The amylase of claim 8, wherein the amino acid sequence is at least 98% identical to the full length amino acid sequence of SEQ ID NO:19.

11. The amylase of claim 8, wherein the amino acid sequence is at least 99% identical to the full length amino acid sequence of SEQ ID NO:19.

12. The amylase of claim 8, wherein the amino acid sequence is 100% identical to the full length amino acid sequence of SEQ ID NO:19.

* * * * *